(12) United States Patent
Tang et al.

(10) Patent No.: US 10,935,552 B2
(45) Date of Patent: Mar. 2, 2021

(54) AIE LUMINOGENS FOR VISUALIZATION AND TREATMENT OF CANCER

(71) Applicant: THE HONG KONG UNIVERSITY OF SCIENCE AND TECHNOLOGY, Hong Kong (CN)

(72) Inventors: Benzhong Tang, Hong Kong (CN); Engui Zhao, Hong Kong (CN); Chen Gui, Hong Kong (CN); Meijuan Jiang, Hong Kong (CN); Haiqin Deng, Hong Kong (CN); Wai Tung Leung, Hong Kong (CN); Zhiming Wang, Liaoning (CN); Yueyue Zhao, Hong Kong (CN); Tsz Kin Kwok, Hong Kong (CN); Lucia Viglianti, Sicily (IT); Ni Xie, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 220 days.

(21) Appl. No.: 15/737,187

(22) PCT Filed: Jun. 24, 2016

(86) PCT No.: PCT/CN2016/086980
§ 371 (c)(1),
(2) Date: Dec. 15, 2017

(87) PCT Pub. No.: WO2016/206615
PCT Pub. Date: Dec. 29, 2016

(65) Prior Publication Data
US 2018/0156811 A1   Jun. 7, 2018

Related U.S. Application Data

(60) Provisional application No. 62/231,069, filed on Jun. 24, 2015, provisional application No. 62/231,932, filed on Jul. 20, 2015, provisional application No. 62/284,162, filed on Sep. 22, 2015, provisional application No. 62/386,380, filed on Nov. 30, 2015.

(51) Int. Cl.
| | | |
|---|---|---|
| C09K 11/06 | (2006.01) |
| G01N 33/58 | (2006.01) |
| C08G 65/00 | (2006.01) |
| A61K 49/00 | (2006.01) |
| A61K 41/00 | (2020.01) |
| A61K 31/4706 | (2006.01) |
| A61K 31/47 | (2006.01) |
| A61K 33/22 | (2006.01) |
| A61K 31/5375 | (2006.01) |
| A61K 31/695 | (2006.01) |
| C09B 23/04 | (2006.01) |
| C09B 26/02 | (2006.01) |
| C09B 57/00 | (2006.01) |

(52) U.S. Cl.
CPC .......... *G01N 33/582* (2013.01); *A61K 31/47* (2013.01); *A61K 31/4706* (2013.01); *A61K 31/5375* (2013.01); *A61K 31/695* (2013.01); *A61K 33/22* (2013.01); *A61K 41/0057* (2013.01); *A61K 49/0021* (2013.01); *C08G 65/00* (2013.01); *C09B 23/04* (2013.01); *C09B 26/02* (2013.01); *C09B 57/00* (2013.01); *C09B 57/008* (2013.01); *C09K 11/06* (2013.01); *C09K 2211/1007* (2013.01); *C09K 2211/1011* (2013.01); *C09K 2211/1014* (2013.01); *C09K 2211/1018* (2013.01); *C09K 2211/1029* (2013.01)

(58) Field of Classification Search
None
See application file for complete search history.

(56) References Cited

U.S. PATENT DOCUMENTS

2014/0212359 A1   7/2014   Tang et al.

FOREIGN PATENT DOCUMENTS

CN   104974745 A   10/2015

OTHER PUBLICATIONS

Zhao, E. et al., Chem Comm. 2014, vol. 50, pp. 14451-14454.*
International Search Report dated Sep. 29, 2016 issued in corresponding International Application No. PCT/CN2016/086980.
Fischer, et al., "Synthesis of New Sulfur Heteroaromatics Isoelectronic with Dibenzo[g.p] chrysene by Photocyclization of Thienyl-and Phenyl-Substituted Ethenes", Journal of Organic Chemistry, vol. 61, No. 20, pp. 6997-7005; Dec. 1996.

* cited by examiner

*Primary Examiner* — Heidi Reese
(74) *Attorney, Agent, or Firm* — Nath, Goldberg & Meyer; Joshua B. Goldberg

(57) ABSTRACT

The present subject matter relates to ATE luminogens for visualization and treatment of cancer, particularly AIE luminogenic probes for cancer cell visualization and discrimination, lysosome-targeting AIEgens for imaging and autophagy visualization, highly fluorescent AIE-active theranostic agents for monitoring drug distribution and having anti-tumor activity to specific cancer cells, probes comprising AIE luminogens for cancer cell imaging and staining, AIE luminogens having clusteroluminogenic features and applications thereof, and methods of preparing thereof.

11 Claims, 25 Drawing Sheets
(20 of 25 Drawing Sheet(s) Filed in Color)

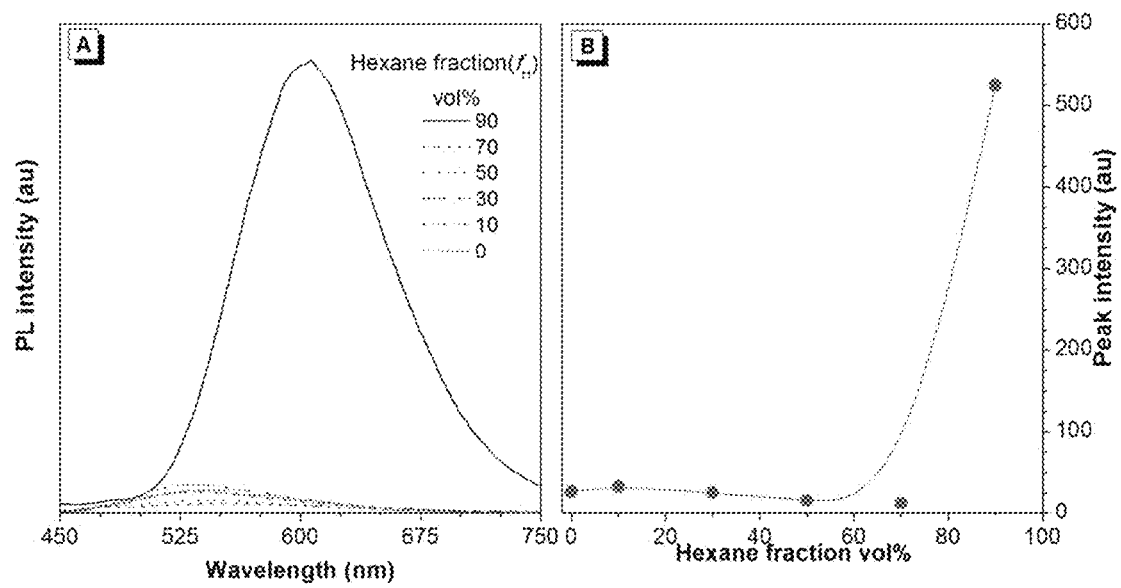
FIG. 3A-B
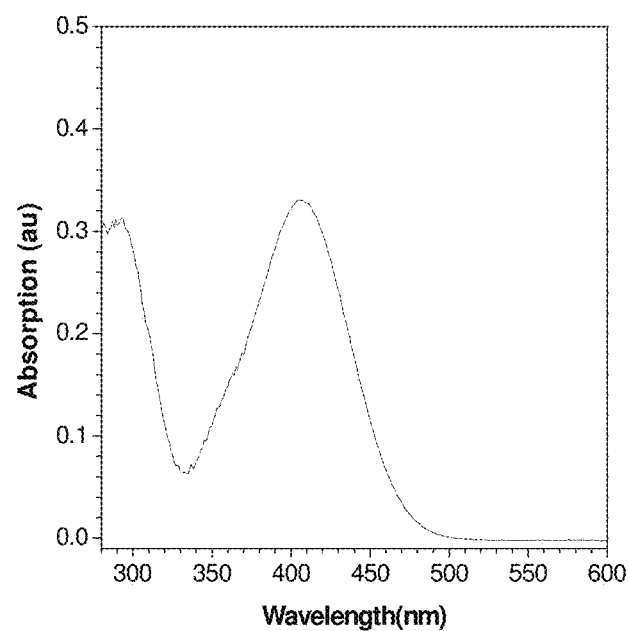
FIG. 4

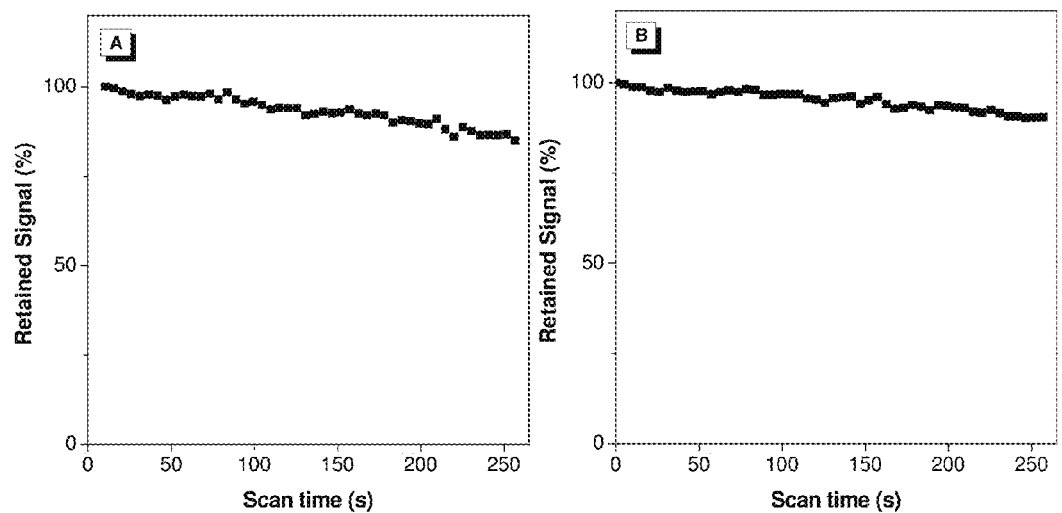
FIG. 9A-B
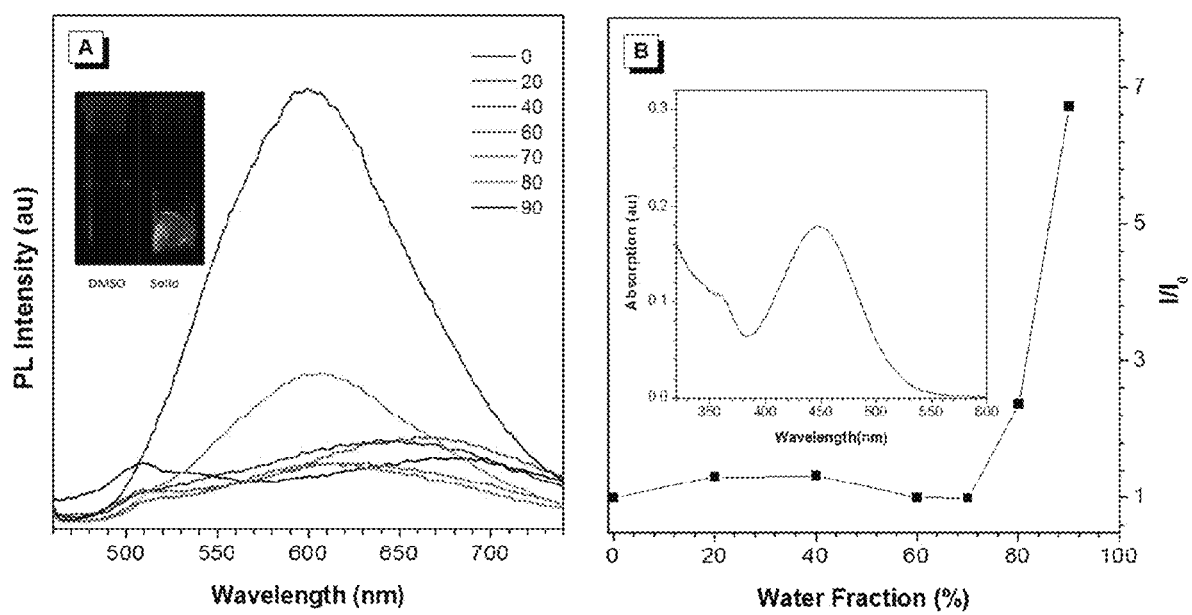
FIG. 10A-B

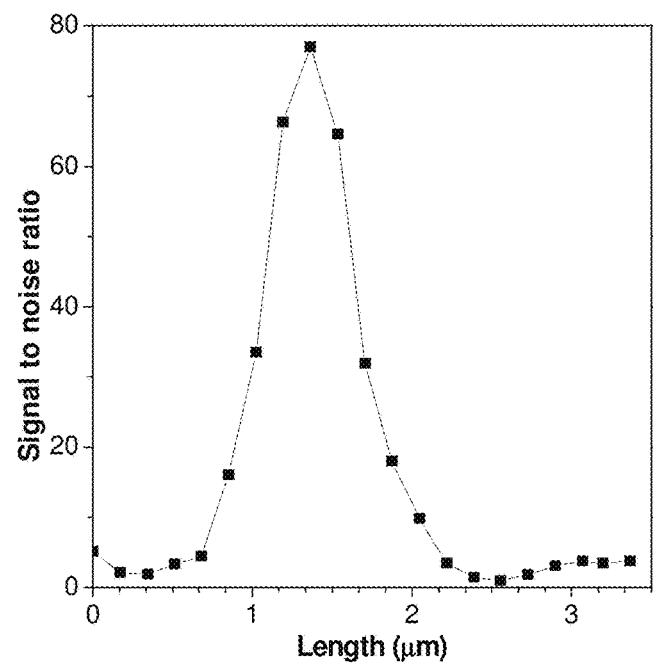
FIG. 13
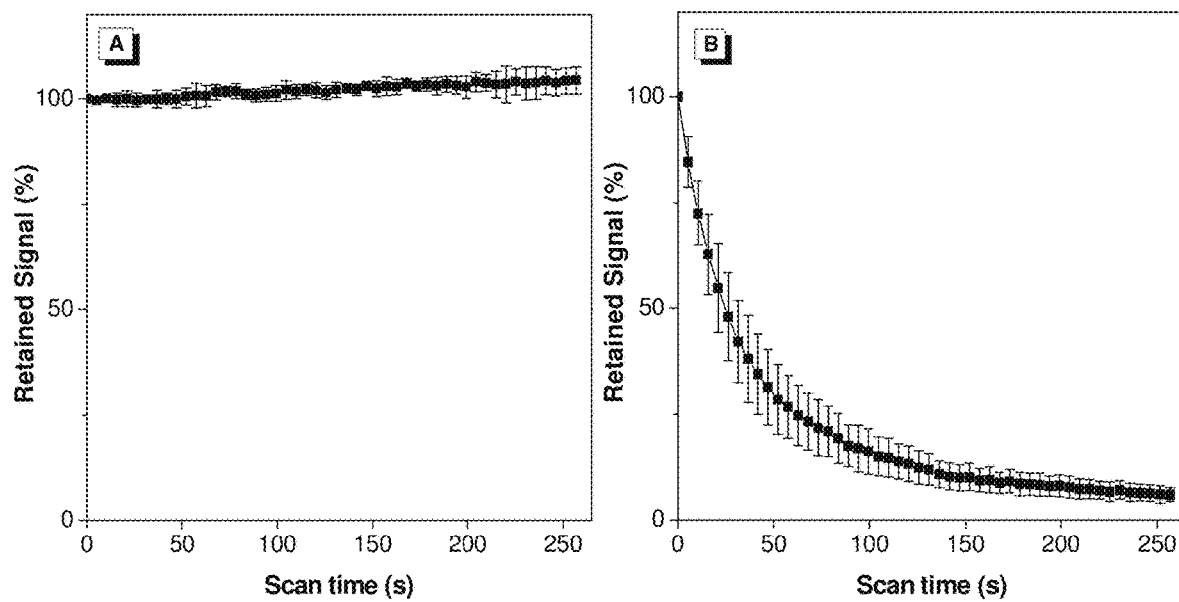
FIG. 14A-B

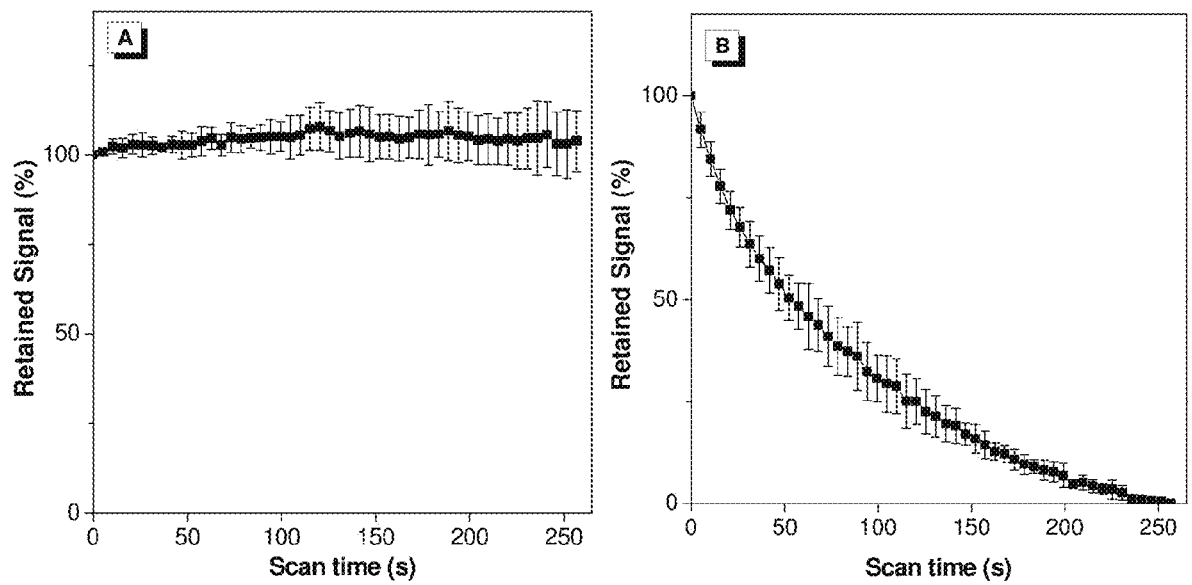
FIG. 19A-B
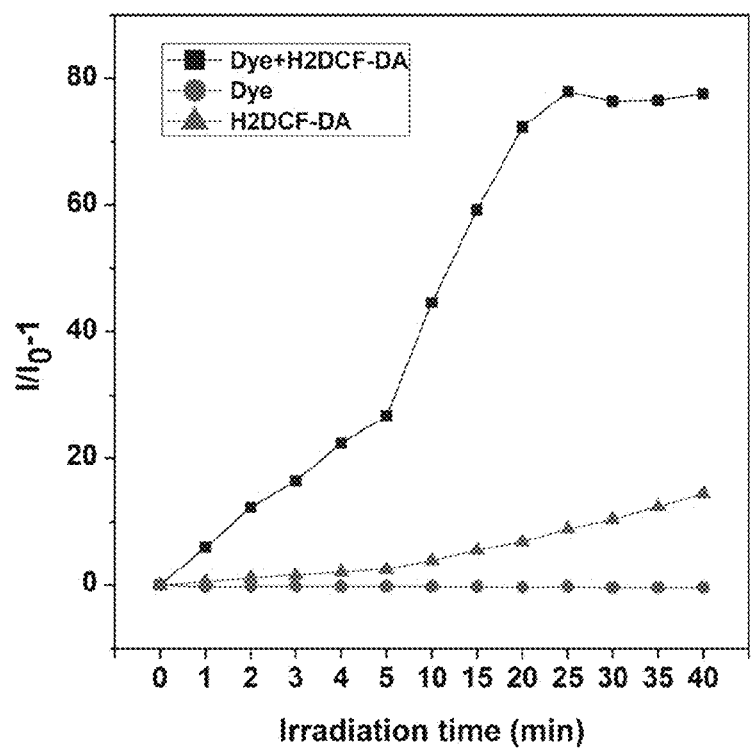
FIG. 20

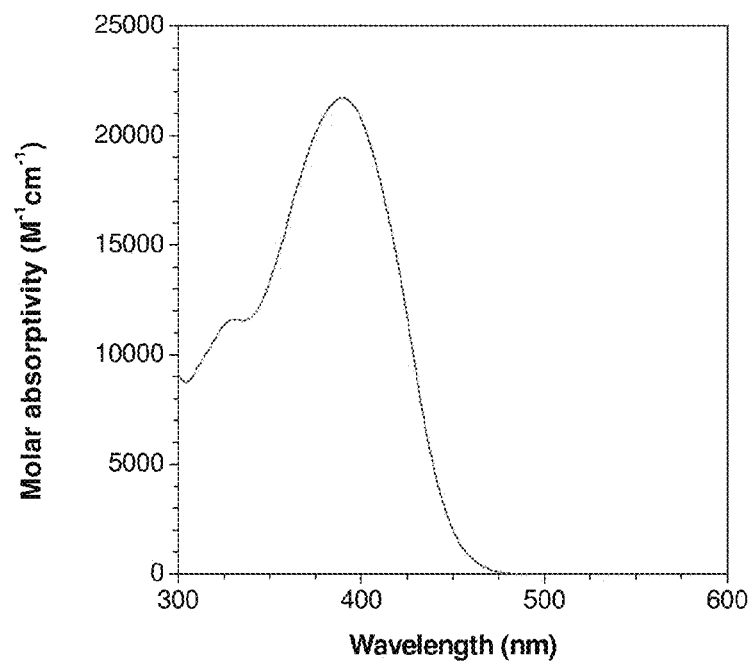
FIG. 23
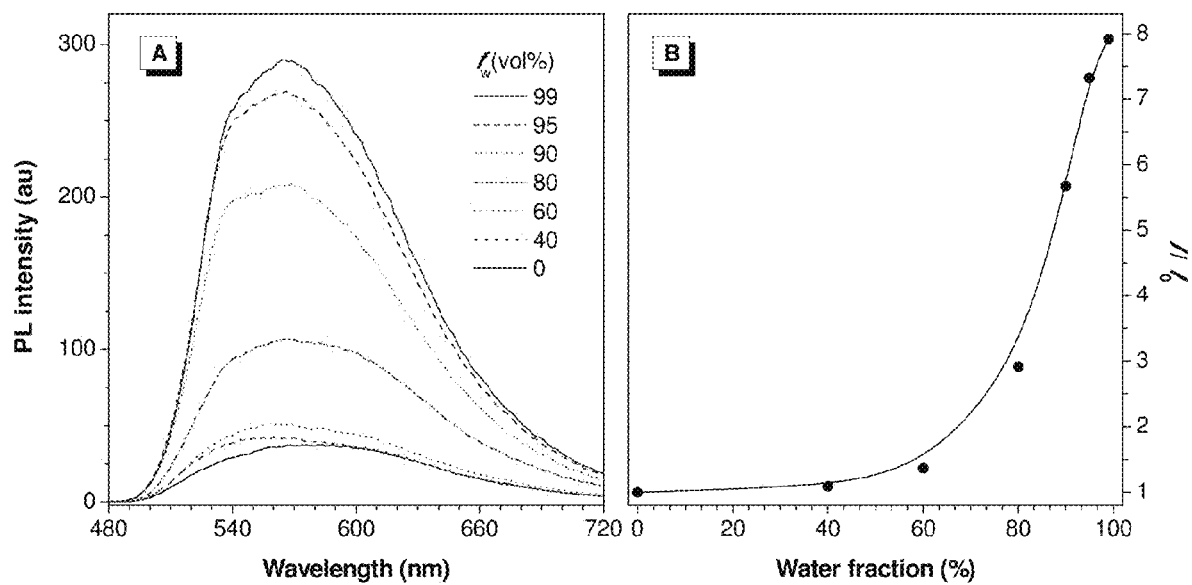
FIG. 24A-B

FIG. 32A-B

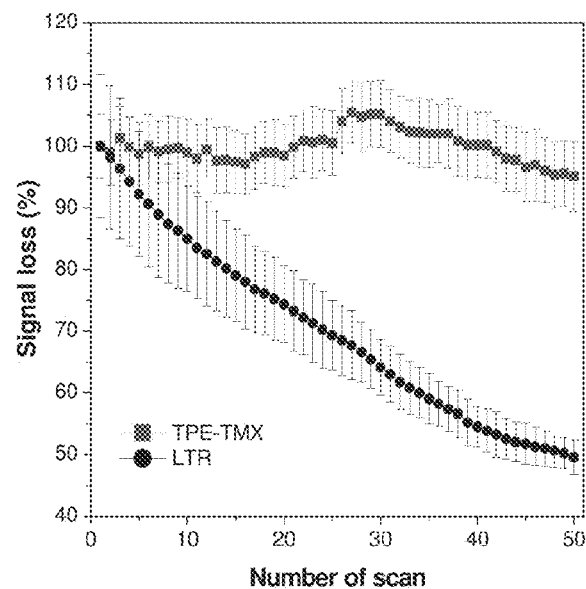
FIG. 34
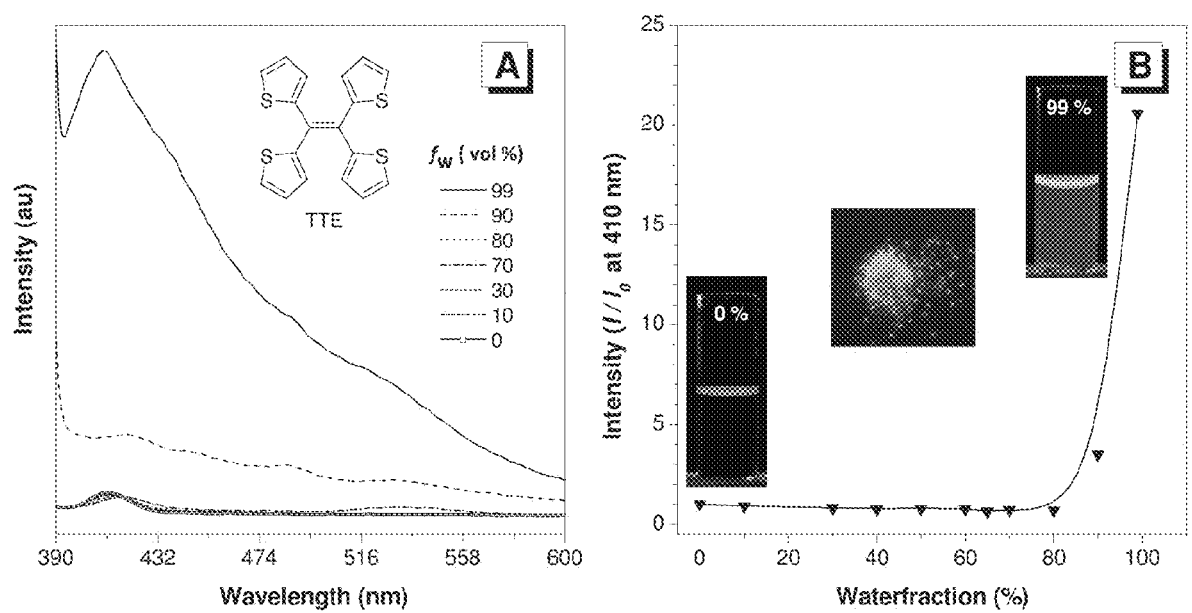
FIG. 35A-B

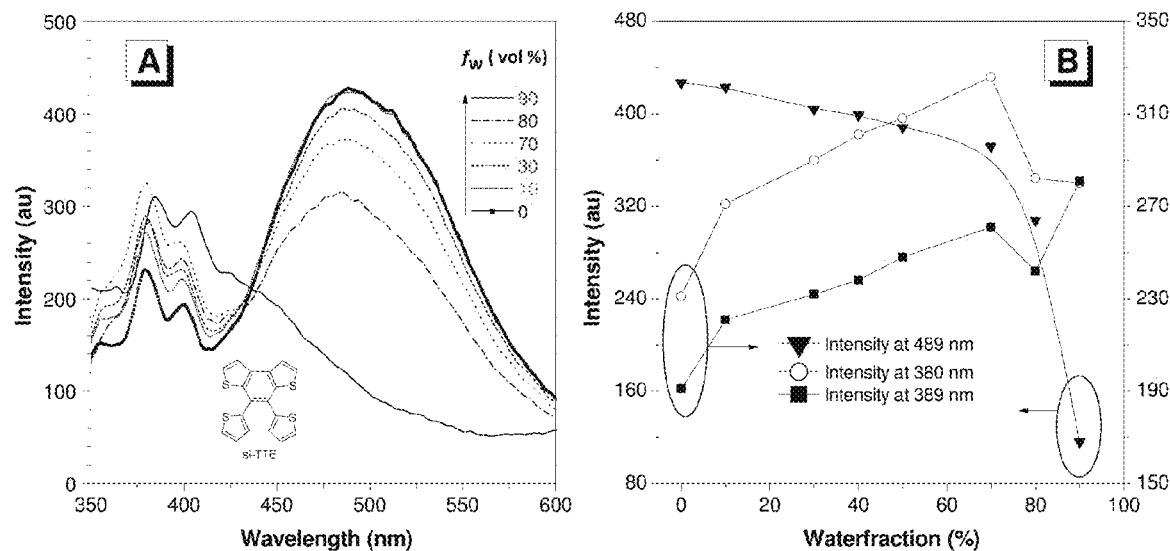
FIG. 37A-B
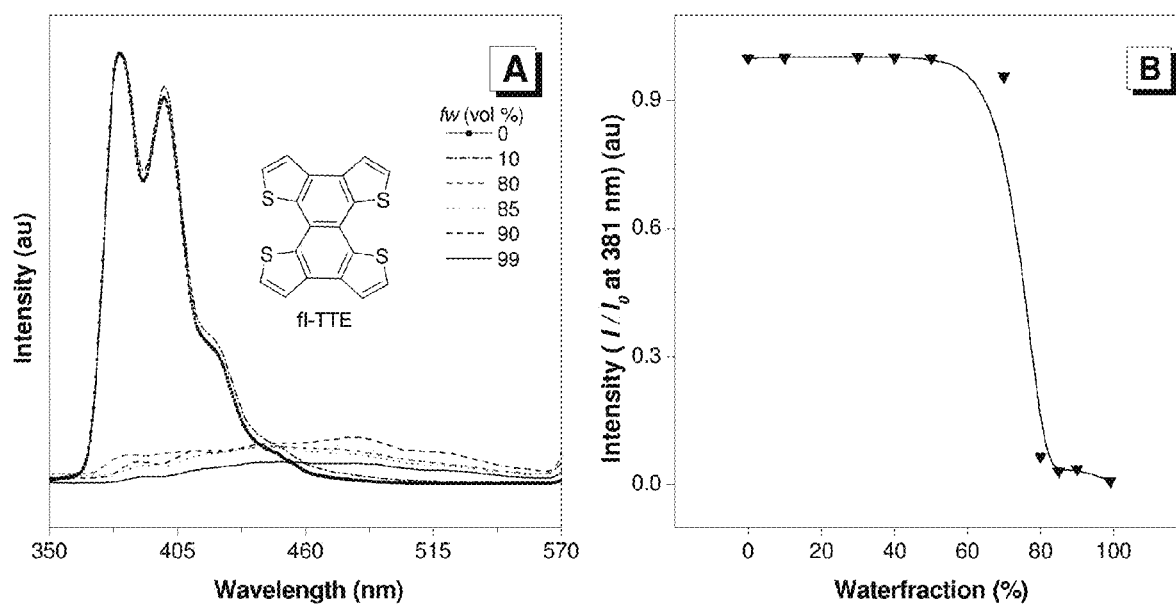
FIG. 38A-B

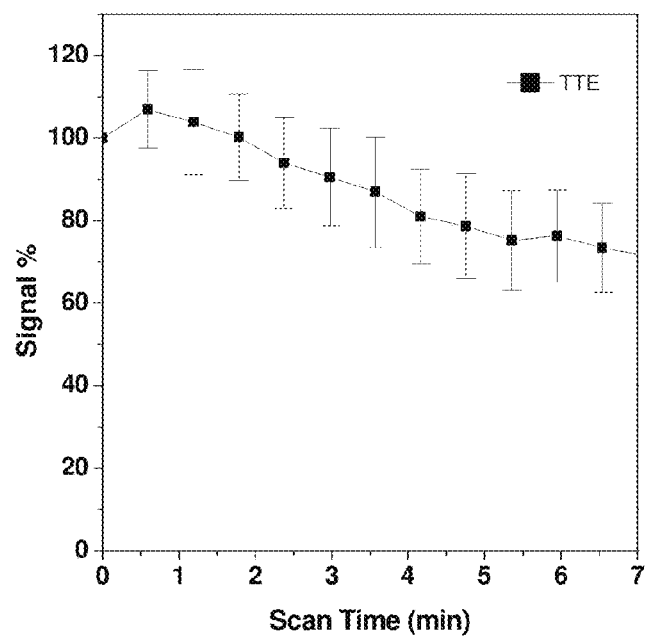
FIG. 41
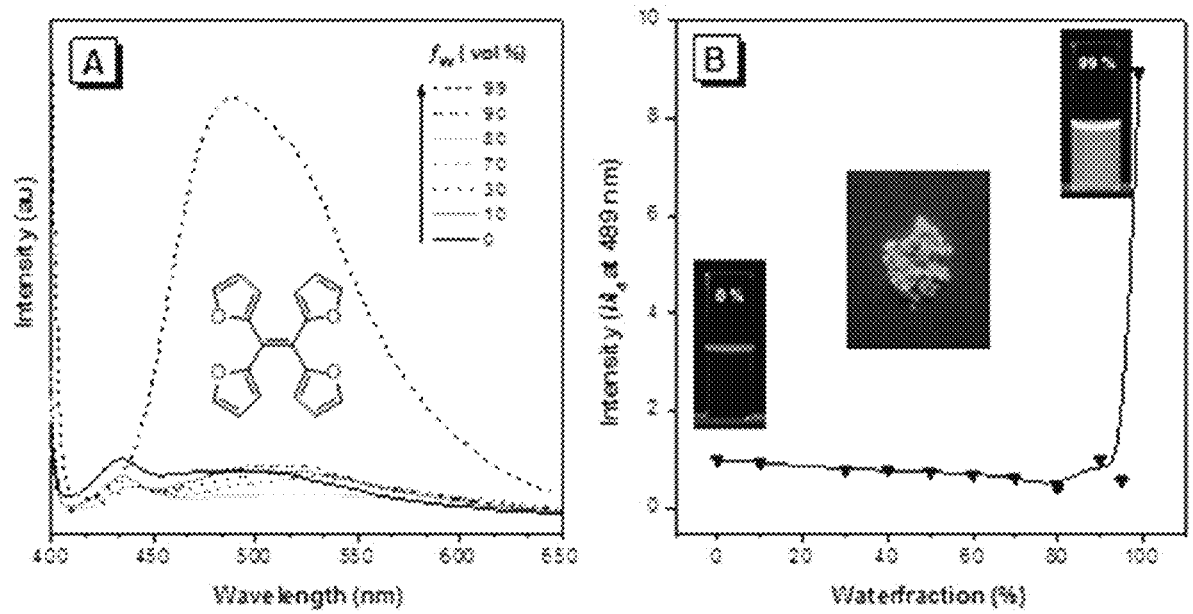
FIG. 42A-B

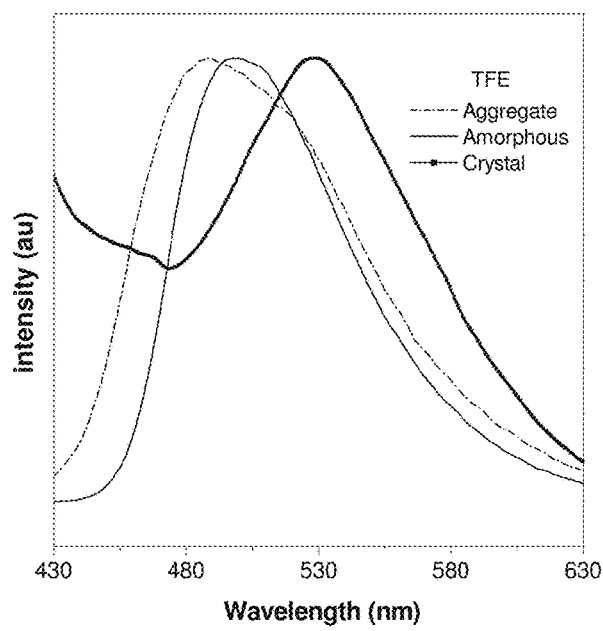
FIG. 43
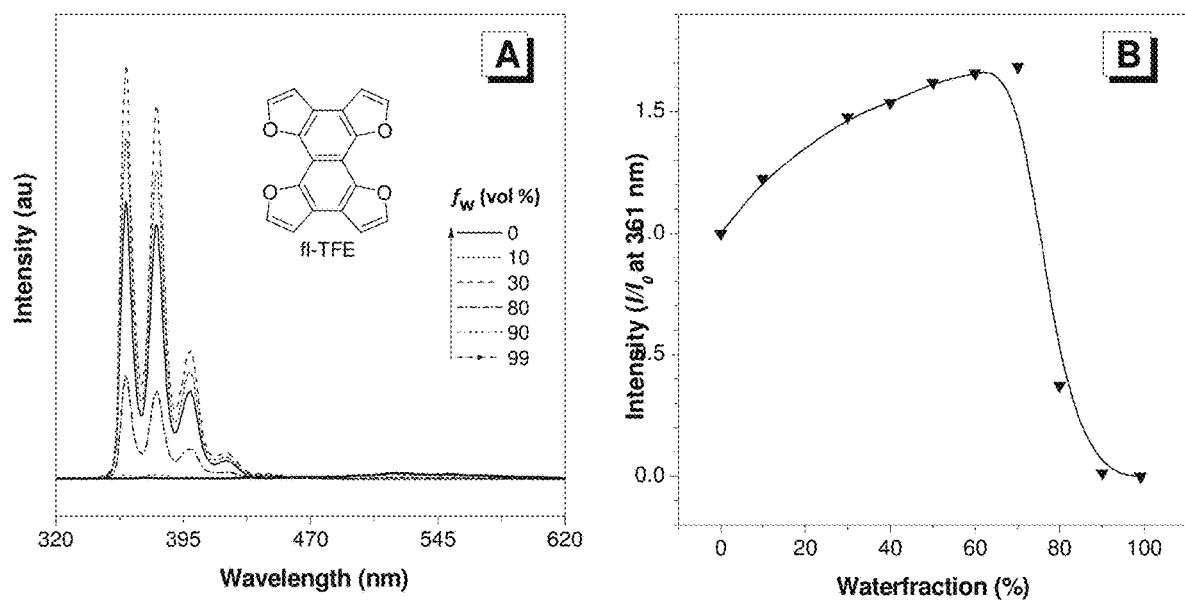
FIG. 44A-B

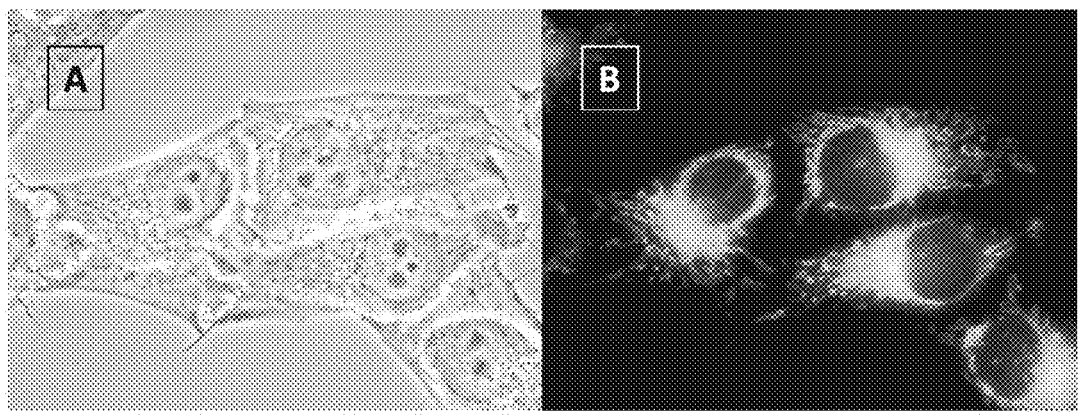
FIG. 45A-B

AIE LUMINOGENS FOR VISUALIZATION AND TREATMENT OF CANCER

RELATED APPLICATIONS

This is a National Phase Application filed under 35 U.S.C. 371 as a national stage of PCT/CN2016/086980, filed Jun. 24, 2016, an application claiming the benefit of U.S. Provisional Application No. 62/231,069, filed Jun. 24, 2015, U.S. Provisional Application No. 62/231,932, filed Jul. 20, 2015, U.S. Provisional Application No. 62/284,162, filed Sep. 22, 2015, and U.S. Provisional Application No. 62/386,380, filed Nov. 30, 2015, the content of each of which is hereby incorporated by reference in its entirety.

TECHNICAL FIELD

The present subject matter relates to aggregation-induced emission (AIE) luminogens for visualization and treatment of cancer. In particular, the present subject matter is directed to AIE luminogenic probes for cancer cell visualization and discrimination, lysosome-targeting AIEgens for imaging and autophagy visualization, highly fluorescent AIE-active theranostic agents for monitoring drug distribution and having anti-tumor activity to specific cancer cells, probes comprising AIE luminogens for cancer cell imaging and staining, AIE luminogens having clusteroluminogenic features and applications thereof, and methods of preparing thereof.

BACKGROUND

With approximately 14 million new cases per year worldwide, cancer remains a difficult disease to treat and a leading cause of morbidity and mortality. The task of discovering and developing safe and effective drugs is more promising as knowledge of the disease increases. However, anticancer drug development is a lengthy, high-risk, and costly endeavor that differs from drug development processes for any other indication. For instance, small molecule drugs usually exert their effects through binding to one or more protein targets. This critical interaction is often poorly understood and generally cannot be visualized in live cells or entire organisms due to the lack of methods to directly measure drug-target engagement in a biological system.

Tamoxifen (TMX) (U.S. Pat. No. 5,192,525 A), for example, is a triphenylethylene derivative pharmacologically classified as a selective ER modulator (SERM) that is used to treat breast cancer. TMX is the most commonly used chemotherapeutic agent for patients with ER+ breast cancer, which represents almost 70% of all cases. Yet, little data exists on how TMX is actually distributed and works at the cellular level. It is postulated that TMX acts as an "estrogen competitor" that binds to estrogen receptors on tumors, producing a nuclear complex that prevents genes from being switched on by estrogen and leads to inhibition of estrogenic effects. However, a major clinical challenge is that about 50% ER+ breast cancers, which are initially sensitive to TMX, can eventually develop TMX resistance. Although several plausible reasons for such resistance have been suggested, the mechanism of resistance to TMX therapy is still waiting for verification. Recently, TMX was shown to induce autophagy in breast cancer cells, but the role of autophagy in the treatment response is still unknown. Thus, to develop anti-breast tumor agents that can be visualized accurately and can be informatively followed during administration will play an essential role to formulate effective treatment plans as well as elucidate their mechanism of action.

Differentiating cancer cells and normal cells is one of the biggest challenges in this century. Conventional technologies, such as computerized tomography (CT), X-Ray, and ultrasonic, among others, are low resolution. Due to the threat of cancer cell migration, which may occur in the late stage of general cancer diseases, the surgical operation of removing cancer cells is normally performed by cutting off a large area of tumor along with extensive normal tissue and skin. Thus, a new material or product that can solve the problem of tracking the cancer cells embedded in normal cells is urgently needed.

Autophagy, which is responsible for maintaining cytoplasmic metabolite equilibrium, has become a hot research topic, owing to its close relationship with cancers, aging, longevity and neurodegenerative diseases, such as Danon disease, Pompe disease, etc. Proper autophagic flux is necessary for controlling the health of an individual. For example, in neurodegenerative diseases, upregulated autophagy has been demonstrated to enhance the clearance of several aggregate-prone proteins, such as mutant tau, α-synuclein, and Huntingtin and reduces symptoms, while down-regulated or impaired induction of autophagy may lead to the accumulation of protein aggregates and exaggerate symptoms. In another neurodegenerative disease, Alzheimer's disease, active autophagy is observed in the brain of patients and mouse models, but autophagy-lysosomal degradation is disrupted, leading to a boost of autophagic compartment accumulation containing the amyloid protein and β-amyloid precursor.

A typical autophagy process is depicted in FIG. 22, a schematic presentation of the autophagy process and rapamycin treatment. At the early stage of autophagy, a membrane cistern called phagophore expands and wraps a portion of cytoplasm until it is sealed. A double-membrane cargo, which is known as an autophagosome, will eventually be formed and will deliver the damaged pieces to the lysosomes. The formation of an autolysosome is accomplished by the fusion of an autophagosome with a lysosome. The encapsulated materials will then be degraded by lysosomal hydrolases. Lysosomes are reformed after the completion of digestion and are able to fuse with the next autophagosome. As a result, a lysosome is the determining subcellular organelle in autophagy execution. Owing to the association of lysosomes with autophagy, visualizing and tracking lysosomal activities will enrich the insight of the autophagic process. Diversity of lysosome-targeting probes are developed for exploring lysosomal-linked cellular activities. For example, with rapamycin, treatment is testified to increase the number of lysosomes through autophagy induction.

A proper lysosome-targeting probe not only facilitates the investigation of autophagy, but also broadens the mechanistic vision of corresponding drugs. In addition to utilizing small organic molecules, lysosome labelling can be done by utilizing a variety of lysosome-associated membrane glycoproteins and metal complexes. Series of commercial fluorescent lysosome-targeting probes are also available with different emission colors. However, they may suffer from nonspecific background signals, inadequate specificity, lengthy incubation and low photostability.

As such, a variety of lysosome-targeting probes have been developed for exploring lysosomal-linked cellular activities, among which LysoTracker® Red DND-99 (LTR) is a good representative. The emission of LTR lights up due to the removal of the photo-induced electron transfer (PET) effect by protonation of its weak base unit in the lysosome. Unfortunately, the fluorescence quenching process by PET is not efficient outside the lysosome, thus accurate localization of the lysosome is difficult. On the other hand, the working concentration of LTR is normally low to prevent the aggregation-caused quenching (ACQ) effect. As a result, LTR has low photostability. Furthermore, LTR exhibits a small Stokes shift with absorption and fluorescence maxima at 577 nm and 590 nm, respectively. Thus, high-resolution images can only be obtained by choosing appropriate excitation and emission ranges. Lysosome labelling can also be done by utilizing metal complexes. However, they may suffer from high background noise, inadequate specificity, lengthy incubation, and low photostability.

Lysosome targeting probes with different functions have been reported in the prior art, examples of which have been reported by Cong Li (CN 103122154 A), Zhen Shen (CN 103242355 A), Baoxiang Zhao (CN 103320120 A), Praveen Pande (U.S. Pat. No. 8,715,944 B2) and Yasuteru Urano (US 20140248654 A1). Generally, these face several problems, such as possessing small Stokes shifts and low photostability and suffering from aggregation-caused quenching or complicated synthetic routes.

Fluorescence-based methods enjoy advantages such as high sensitivity, high selectivity, easy operation and rapid response over other methods. Some fluorescent dyes are commercially available for cancer cell staining, but do not have characteristics to differentiate cancer cells from normal cells. Thus, specifically identifying cancer cells at the microlevel is very difficult, and the fluorescent probe technology is important in solving this problem. However, some fluorescent tracers suffer from no selectivity, or even emission quenching problems when used to stain cancer cells.

SUMMARY

In an embodiment, the present subject matter is directed to a probe for cancer cell imaging and staining comprising AIE luminogens having a chemical structure selected from the group consisting of:

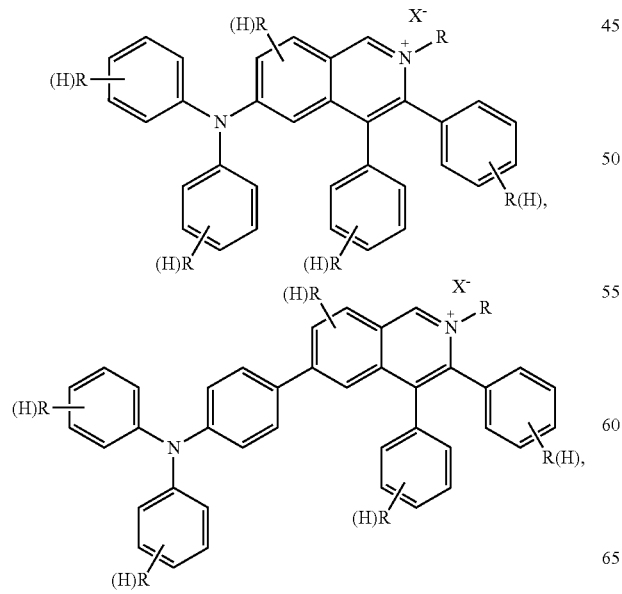

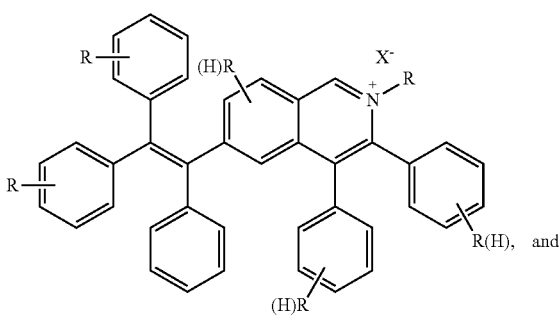

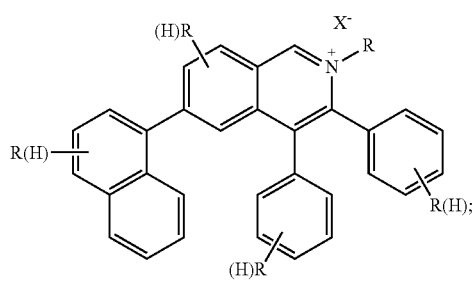

wherein the counteranion X− is selected from anions with single or more charges; and wherein each R is independently selected from the group consisting of alkyl, unsaturated alkyl, heteroalkyl, cycloalkyl, heterocycloalkyl, aryl, and heteroaryl. An embodiment of the present subject matter is directed to an AIEgen for lysosome imaging comprising: a morpholine-functionalized AIE Derivative comprising a backbone structure selected from the group consisting of

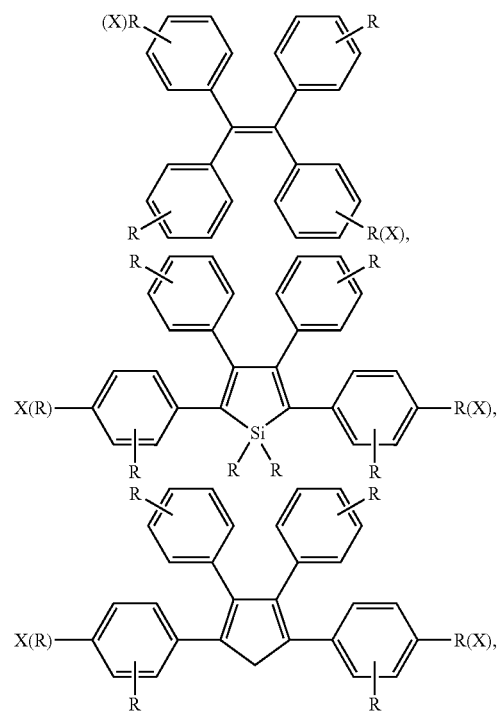

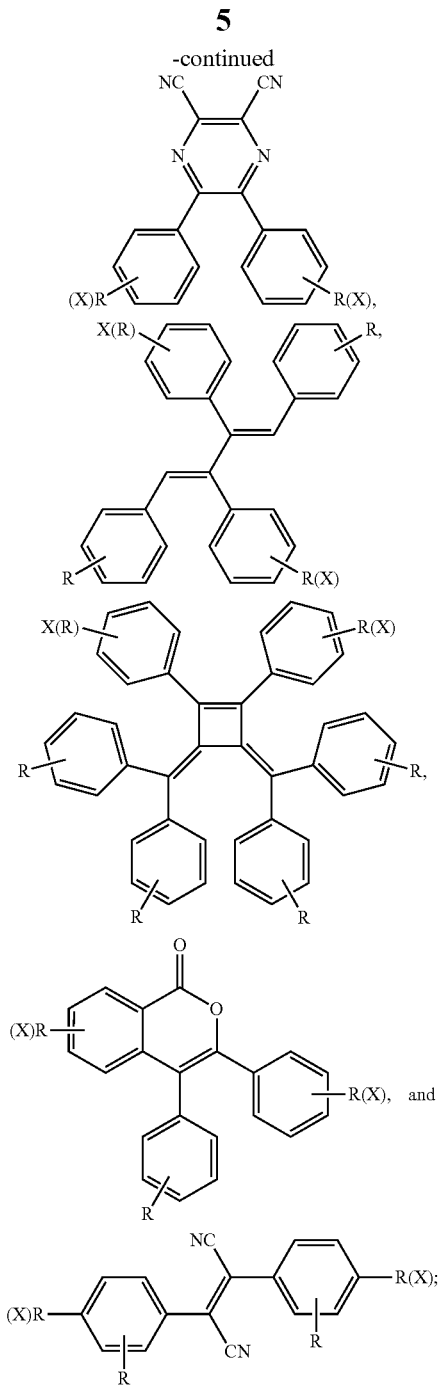

wherein at least one of R, R', R", and R'" is

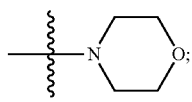 [SMILES: *N1CCOCC1]

and wherein R, R', R", and R'" are independently selected from the group consisting of

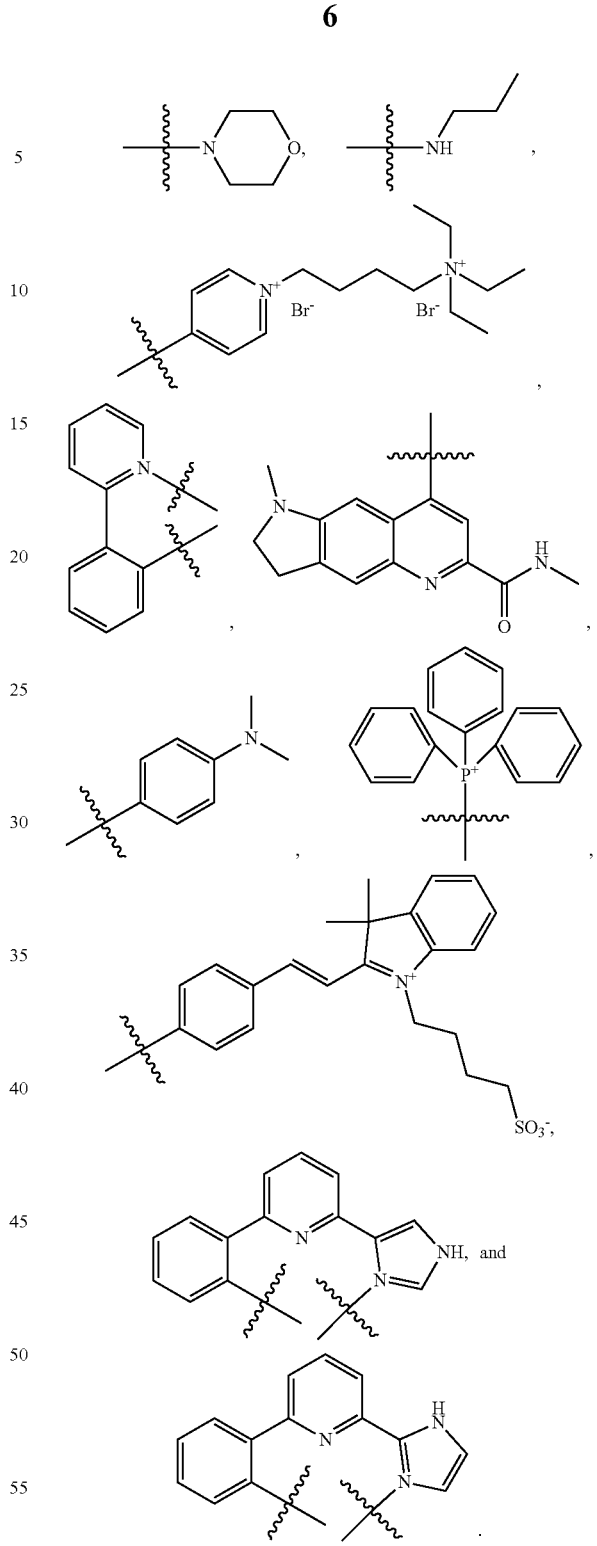

An embodiment of the present subject matter is directed to a method of lysosome imaging and autophagy process visualization comprising: introducing the AIEgen of the present subject matter to a sample; and imaging lysosomes and visualizing the autophagy process by observing fluorescence of the AIEgen, activated by the AIEgen entering and accumulating lysosomes through protonation and alternation of permeability.

In an embodiment, the present subject matter is directed to an AIEgen for lysosome imaging comprising: a morpholine-functionalized AIE Derivative having the chemical structure of

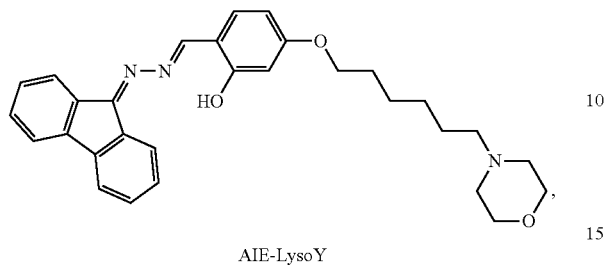

AIE-LysoY

In an embodiment, the present subject matter is directed to a fluorescent bioprobe for treating and imaging anti-tumor activity comprising: AIE fluorogens comprising amino functional groups and having a chemical structure selected from the group consisting of:

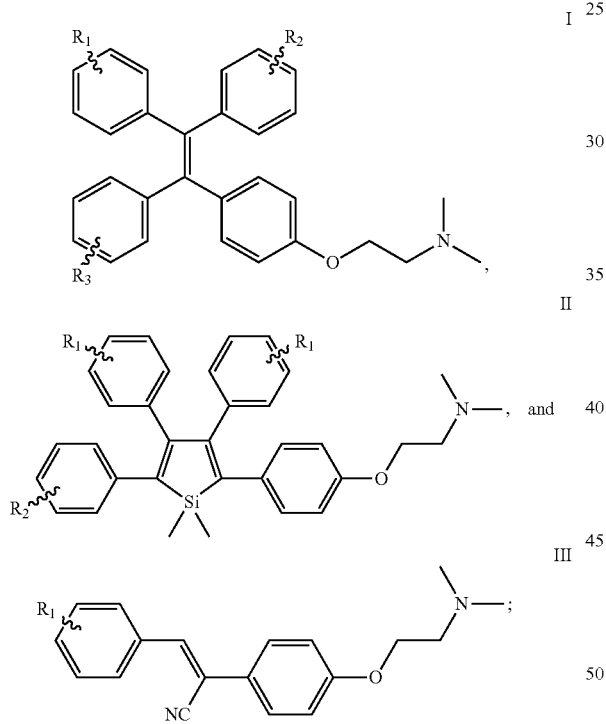

wherein $R_1$, $R_2$, and $R_3$ are independently selected from the group consisting of H, alkyl, unsaturated alkyl, heteroalkyl, cycloalkyl, heterocycloalkyl, aryl, and heteroaryl.

An embodiment of the present subject matter is directed to a method of treating and imaging anti-tumor activity comprising: introducing the bioprobe of the present subject matter to a sample containing cells; and detecting cellular imaging by fluorescent microscopy or confocal laser scanning microscopy wherein fluorescence is emitted by probes uptaken by cells and accumulated in mitochondria.

In an embodiment, the present subject matter is directed to a probe for cancer cell imaging and staining comprising AIE luminogens having a chemical backbone structure selected from the group consisting of:

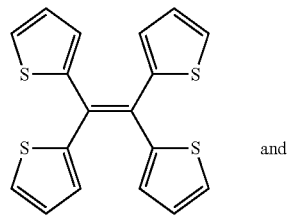

TTE and

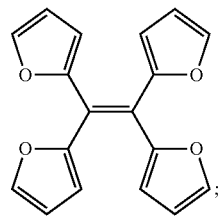

TFE

;

wherein the AIE luminogens are clusteroluminogens; and wherein TTE serves as a dye for cancer cell imaging.

In an embodiment, the present subject matter is directed to luminophores having a chemical structure consisting of:

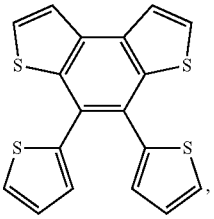

sl-TTE

,

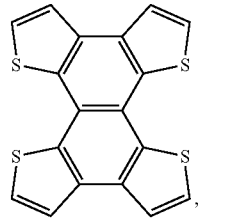

fl-TTE and

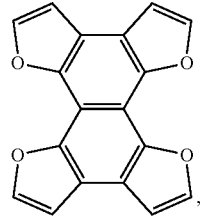

fl-TFE

,

In an embodiment, the present subject matter is directed to a probe for cancer cell imaging and staining comprising AIE luminogens having a chemical structure of:

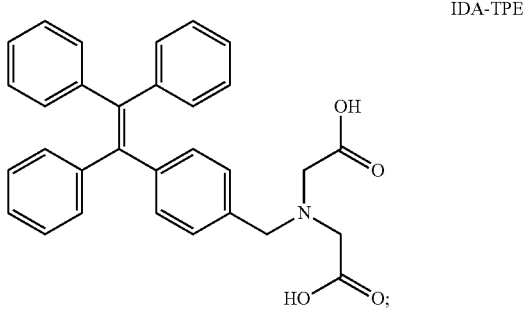 [SMILES: O=C(O)CN(CC(=O)O)Cc1ccc(C(=C(c2ccccc2)c2ccccc2)c2ccccc2)cc1]
IDA-TPE wherein the AIE luminogens are uptaken by cancer cells and images show organelles inside the cancer cells are stained.

The patent of application file contains at least one drawing executed in color. Copies of this patent or patent application publication with color drawing(s) will be provided by the office upon request and payment of the necessary fee.

BRIEF DESCRIPTION OF DRAWINGS

FIG. 3A-B shows (A) PL spectra of TPE-IQ-2O in Hexane/THF mixtures with different hexane fractions ($f_H$) and (B) a plot of relative PL intensity with different hexane fraction. Excitation Wavelength: 420 nm.

FIG. 4 shows absorption spectra of DPA-IQ in DMSO (10 μM).

FIG. 9A-B shows plots of retained signal of DPA-IQ in Hela cells versus scan time: a total of 50 frames were taken consecutively in the experiment and scan time of each frame is 5.24 s. (A) One photon excited with 442 nm laser, and (B) two photon excited with 860 nm laser. Hela cells were stained with 50 nM DPA-IQ in PBS for 10 min.

FIG. 10A-B shows A) emission spectra of TPA-IQ in DMSO/water mixture with different water fraction and B) a plot of relative emission peak intensity (I/I$_0$) of TPA-IQ versus the water fraction. Concentration: 10 μM, excitation: 440 nm (Right insert panel) Absorption spectra of TPA-IQ in DMSO (10 μM) and (Left insert panel) photos of TPA-IQ in DMSO (10 μM) and solid state under 365 nm irradiation.

FIG. 13 shows S/N ratio of Naph-IQ in the Hela cells. Hela cells were stained with 400 nM TPA-IQ in PBS for 10 min. Excited with 442 nm laser.

FIG. 14A-B shows plots of retained signal of TPA-IQ in Hela cells versus scan time: a total of 50 frames were taken consecutively in the experiment and scan time of each frame is 5.24 s. (A) One photon excited with 442 nm laser and (B) two photon excited with 860 nm laser. Hela cells were stained with 50 nM TPA-IQ in PBS for 10 min.

FIG. 19A-B shows plots of retained signal of Naph-IQ in Hela cells versus scan time: a total of 50 frames were taken consecutively in the experiment and scan time of each frame is 5.24 s. (A) One photon excited with 442 nm laser and (B) two photon excited with 820 nm laser. Hela cells were stained with 200 nM Naph-IQ in PBS for 10 min.

FIG. 20 shows the fluorescence change of TPE-IQ-2O, H2DCF-DA and the mixture with different irradiation time of light. The mixture display increased intensity, which indicates the continuous ROS generation. Dye (TPE-IQ-2O): 10 mM; H2DCF-DA: 5 mM. Excitation wavelength: 488 nm.

FIG. 23 shows UV spectrum of AIE-LysoY in THF. [AIE-LysoY]=10 μM.

FIG. 24A-B shows (A) PL spectra of AIE-LysoY in THF/water mixtures with different water fractions ($f_w$) and (B) a plot of I/I$_0$ versus the composition of the THF/water mixture of AIE-LysoY. Concentration=10 μM; I$_0$=PL intensity in pure THF solution; $\lambda_{ex/em}$=390/565 nm.

FIG. 34 shows loss in TPE-TMX and LTR emission of stained MCF-7 cells with the number of scans. Excitation wavelength: 405 nm (TPE-TMX) and 561 nm (LTR); emission filter: 450-750 nm (TPE-TMX), 580-750 nm (LTR). Irradiation time: 3.58 sec/scan. Laser power: 0.1 mW.

FIG. 35A-B shows (A) the PL spectra of TTE in THF and THF/water mixtures with increasing water fractions ($f_w$) to 99% and (B) change in PL intensity of TTE at 410 nm versus water fraction in THF/water mixtures. Excitation at 368 nm.

FIG. 37A-B shows (A) the PL spectra of sl-TTE in THF and THF/water mixtures with increasing water fractions ($f_w$) to 90%. (B) Change in PL intensity of sl-TTE at: 489, 389, and 380 nm versus water fraction in THF/water mixtures. Excitation at 323 nm.

FIG. 38A-B shows (A) the PL spectra of fl-TTE in THF and THF/water mixtures with increasing water fractions (fw) to 90% and (B) change in PL intensity of fl-TTE at 381 nm versus water fraction in THF/water mixtures. Excitation at 299 nm.

FIG. 41 shows photostability of TTE in lung cancer cell A549.

FIG. 42A-B shows (A) the PL spectra of TFE in THF and THF/water mixtures with increasing water fractions (fw) to 99% and (B) change in PL intensity of TFE at 489 nm versus water fraction in THF/water mixtures. Excitation at 387 nm.

FIG. 43 shows the PL spectrum of TFE in aggregate, amorphous, and crystal state. Excitation at 387 nm.

FIG. 44A-B shows (A) the PL spectra of fl-TFE in THF and THF/water mixtures with increasing water fractions (fw) to 99% and (B) change in PL intensity of fl-TFE at 361 nm versus water fraction in THF/water mixtures. Excitation at 274 nm.

FIG. 45A-B shows images of Hela cell staining by IDA-TPE. Staining time: 30 min. Concentration: 10 μM.

DETAILED DESCRIPTION

Definitions

Figure 1:
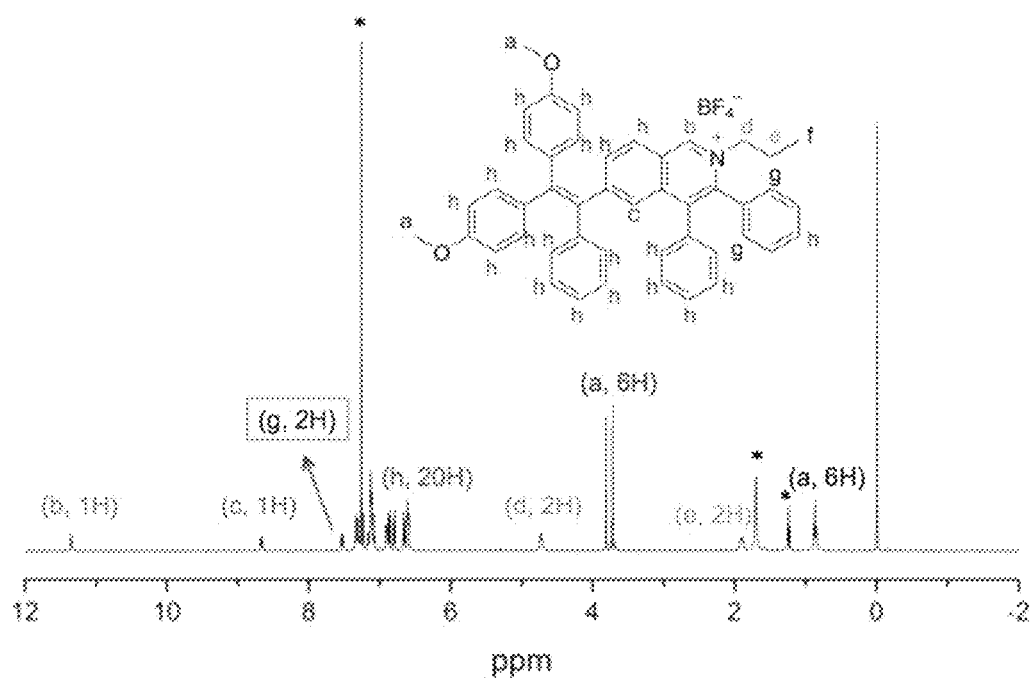
FIG. 1 shows $^1$H-NMR spectrum of TPE-IQ-2O in CDCl$_3$.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

"Aggregation-induced emission" means the fluorescence/phosphorescence is turned on upon aggregation formation or in the solid state. When molecularly dissolved, the material is nonemissive. However, the emission is turned on when the intramolecular rotation is restricted.

"Emission intensity" means the magnitude of fluorescence/phosphorescence normally obtained from a fluorescence spectrometer or fluorescence microscopy measurement.

"Fluorophore" or "fluorogen" means a molecule which exhibits fluorescence.

"Luminogen" or "luminophore" means a molecule which exhibits luminescence.

"AIEgen" means a molecule exhibiting ATE characteristics.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Abbreviations
A549 A549 cell line
ACQ aggregation-caused quenching
AIE aggregation-induced emission
AIE-LysoY (E)-2-(((9H-fluoren-9-ylidene)hydrazono)methyl)-5-((6-morpholinohexyl)oxy)phenol
BODIPY boron-dipyrromethene
COS-7 COS-7 cell line, where "COS" is derived from cells being CV-1 (simian) in Origin, and carrying the SV40 genetic material
CT computerized tomography
DCM dichloromethane
DMEM Dulbecco's Modified Eagle Medium
DMSO dimethylsulfoxide
ESIPT excited-state intramolecular proton transfer
FAS-Br (E)-2-(((9H-fluoren-9-ylidene)hydrazono)methyl)-5-((6-bromohexyl)oxy)phenol
FBS Fetal Bovine Serum
fl-TFE fully locked-TFE
fl-TTE fully-locked TTE
H2DCF-DA 2',7'-dichlorodihydrofluoroscein diacetate
HCC827 HCC827 cell line, a non-small cell lung cancer cell line Hela human cervical carcinoma cell line
HepG2 human hepatocarcinoma cell line
HPLC high pressure liquid chromatography
HPS HexaPhenylSilole
HRMS high-resolution mass spectroscopy
IDA-TPE iminodiacetic acid tetraphenylethene
LDH lactate dehydrogenase
LTR LysoTracker Red DND-99
LX2 normal cell, human hapatic stellate cell line
MALDI-TOF matrix assisted laser desorption ionization time-of-flight
MCF-7 MCF-7 cell line, a breast cancer cell line
MDA-MB-231 MDA-MB-231 cell line, a breast adenocarcinoma cell line
MDCK-II MDCK-II cell line, where "MDCK" is derived from Madin-Darby Canine Kidney
MEM Minimum Essential Medium
MTT 3-(4,5-dimethyl-2-thiazolyl)-2,5-diphenyltetrazolium bromide
mTOR mammalian target of rapamycin
NMR nuclear magnetic resonance
OPE oligo-(p-phenylene ethynylene)
PBS phosphate buffer saline
PC-9 human lung adenocarcinoma cell line
PDT photodynamic therapy
PET photo-induced electron transfer
PL photoluminescence
RIM restriction of intramolecular motions
RIR restriction of intramolecular rotations
ROIs Cell Regions of Interest
ROS reactive oxygen species
SERM selective ER modulator
sl-TTE semi-locked TTE
S/N signal to noise ratio
THF tetrahydrafuran
TFA trifluoroacetic acid
TFE TetraFurylEthene
TLC thin layer chromatography
TMX Tamoxifen
TPE TetraPhenylEthene
TPE-IQ-2O 6-(2,2-bis(4-methoxyphenyl)-1-phenylvinyl)-3,4-diphenyl-2-propylisoquinolin-2-ium
TTE TetraThienylEthene
UV ultraviolet
AIE Luminogenic Probes for Cancer Cell Visualization and Discrimination In an embodiment, the present subject matter is directed to an organic probe that has AIE properties to selectively stain cancer cells and the method of preparing thereof. When applying the probe to a mixture of healthy normal cells selected from COS-7 or MDCK-II, and cancer cells selected from HeLa, MDA-MB-231 and MCF-7, a bright luminescence is observed from the cancer cells while only a faint emission is observed from the normal cells. Other cancer cells, such as PC-9, HepG2, and HCC827, emit strong fluorescence after being stained by the organic probe. However, normal cells LX2 have no obvious emission. Upon facilitating the AIE probe, cancer cells may be visualized in situ by a spraying technique for surgery operations. Furthermore, the organic probe can generate ROS upon light irradiation, thus making it a promising candidate for cancer therapy.

In the present subject matter, a fluorescent probe with AIE characteristics is designed and synthesized. Multiple aldehyde functionalized aromatic conjugated polyarylene derivatives are further synthesized via three-component reaction with internal alkynes and primary amines to yield several cancer cell visualizing probes with ATE characteristics. The AIE active molecules are applied to cancer cell visualization and differentiation from co-staining a mixture of cancer and normal cells.

An embodiment of the present subject matter relates to a probe for cancer cell imaging and staining comprising AIE luminogens having a chemical formula selected from the group consisting of:

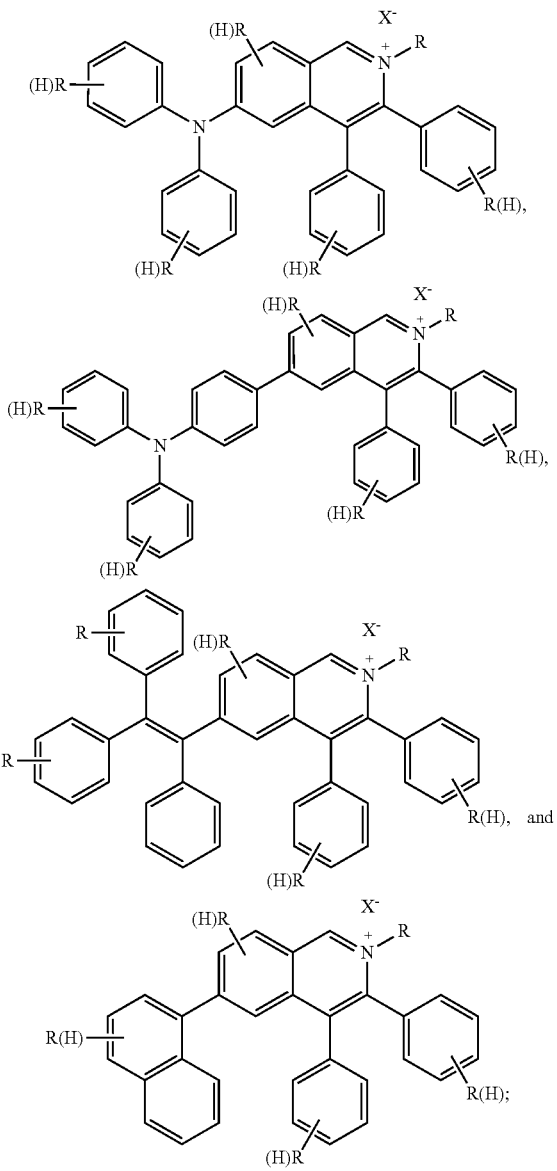

wherein the counteranion $X^-$ is selected from anions with single or more charges; and wherein each R is independently selected from the group consisting of alkyl, unsaturated alkyl, heteroalkyl, cycloalkyl, heterocycloalkyl, aryl, and heteroaryl.

In an embodiment, the AIE luminogens of the present subject matter are selected from the group consisting of:

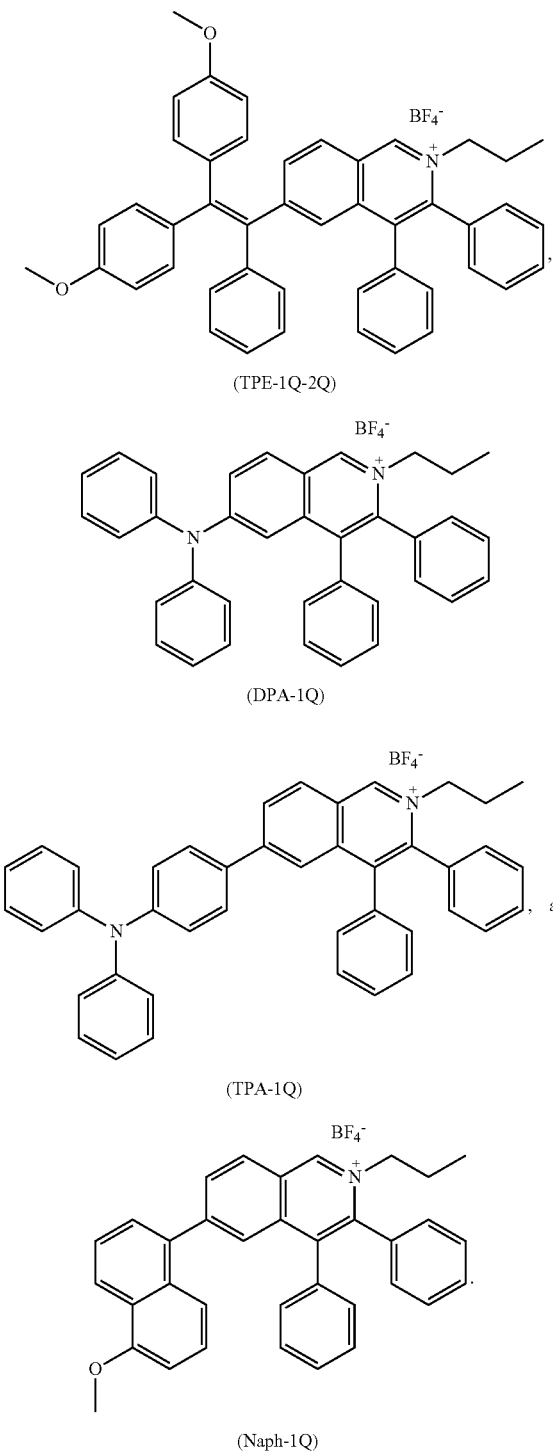

(TPE-1Q-2Q)

(DPA-1Q)

(TPA-1Q)

(Naph-1Q)

Two photon absorption (TPA) is the simultaneous absorption of two photons of identical or different frequencies in order to excite a molecule from one state (usually the ground state) to a higher energy electronic state. Further, the energy difference between the involved lower and upper states of the molecule is equal to the sum of the energies of the two photons, and this ability enables the molecule to be excited by light of longer wavelengths. In an embodiment, the probe of the present subject matter has two-photon absorption ability and can be excited by longer wavelengths. In an embodiment, the probe of the present subject matter exhibits mitochondria selectivity for staining. In an embodiment, the probe of the present subject matter is used for mitochondria imaging, as the AIE luminogens have electrostatic interaction with mitochondria. In an embodiment, imaging is possible due to fluorescence emitted by mitochondria from cell uptake of the probe. In an embodiment, an imaging sample may comprise any kind of cells. In an embodiment, the imaging sample comprises any cancer cells. For example, the cancer cells may be selected from the group consisting of HeLa cells, MCF-7 cells, MDA-MB-231 cells, PC-9 cells, HepG2 cells, and HCC827 cells.

In an embodiment, the probe of the present subject matter can distinguish normal cells from cancer cells by a difference in fluorescence intensity, wherein the cancer cells and the normal cells are stained separately or in a mixture. In an embodiment, the cancer cells have a higher fluorescence intensity and the normal cells have a lower fluorescence intensity, due to the cancer cells uptaking and accumulating more probes of the present subject matter.

In an embodiment, the present subject matter is directed to a method of imaging cells comprising: introducing a probe as described herein to a sample containing cells, wherein the AIE luminogens have electrostatic interaction with mitochondria; and imaging the cells by monitoring fluorescence emitted by probes uptaken by the cells and accumulated in mitochondria.

In an embodiment, the probe of the present subject matter is used with an imaging sample comprising any kind of cell, for example, those identified above.

In an embodiment, the probe of the present subject matter is subject to light irradiation, which generates ROS.

A Lysosome-Targeting AIEgen for Autophagy Visualization

Furthermore, the autophagy process is responsible for degrading and recycling cytoplasmic materials, where lysosomes play a determining role in autophagy execution. To obtain more insight of autophagy, lysosome-targeting probes with high contrast and photostability are desirable.

AIEgens have been utilized in numerous fluorescent biosensing systems, including organelle targeting, protein probing, DNA differentiation, etc. To obtain better signal-to-noise ratio, hydrophilic groups, charged moieties or peptide chains, can be incorporated into typical AIE cores (TPE and silole) to enhance water solubility and weaken emission in aqueous media.

As such, an embodiment of the present subject matter is directed to the design and synthesis of a fluorescent AIE probe, namely AIE-LysoY, a morpholine-functionalized aggregation-induced emission luminogen. To attain outstanding imaging contrast, AIE-LysoY was equipped with excited-state intramolecular proton transfer (ESIPT) characteristics. AIE-LysoY provides a new platform for lysosome visualization with good biocompatibility, large Stokes shift, superior signal-to-noise ratio, and high photostability, with ESIPT characteristics, and its utility in visualization of lysosomes and the lysosome-involved autophagy process. The chemical structure of AIE-LysoY is:

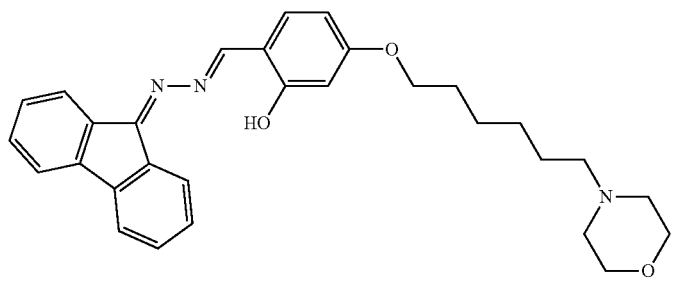

AIE-LysoY                    Morpholine.

Guided by its morpholine functionality, AIE-LysoY selectively accumulates in and lights up the lysosome of cells. Thanks to the collective effect of AIE and ESIPT properties, AIE-LysoY can visualize the lysosome in HeLa cells with superior resolution and contrast. AIE-LysoY also enjoys the advantages of a large Stokes shift, simple operation, varied incubation concentration and time, excellent photostability and high affinity towards lysosome, which enables it to locate lysosomes accurately and provide more insight on lysosomal-related intracellular activities such as autophagy.

An embodiment of the present subject matter is directed to an AIEgen for lysosome imaging comprising: a morpholine-functionalized AIE Derivative comprising a backbone structure selected from the group consisting of

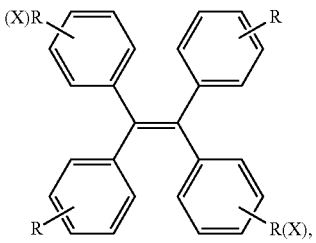

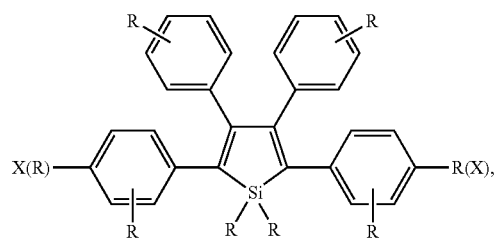

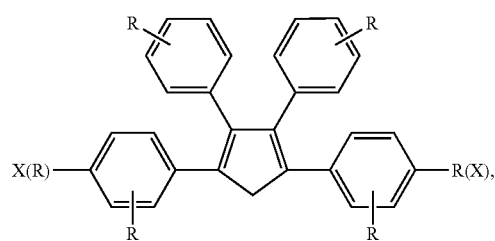

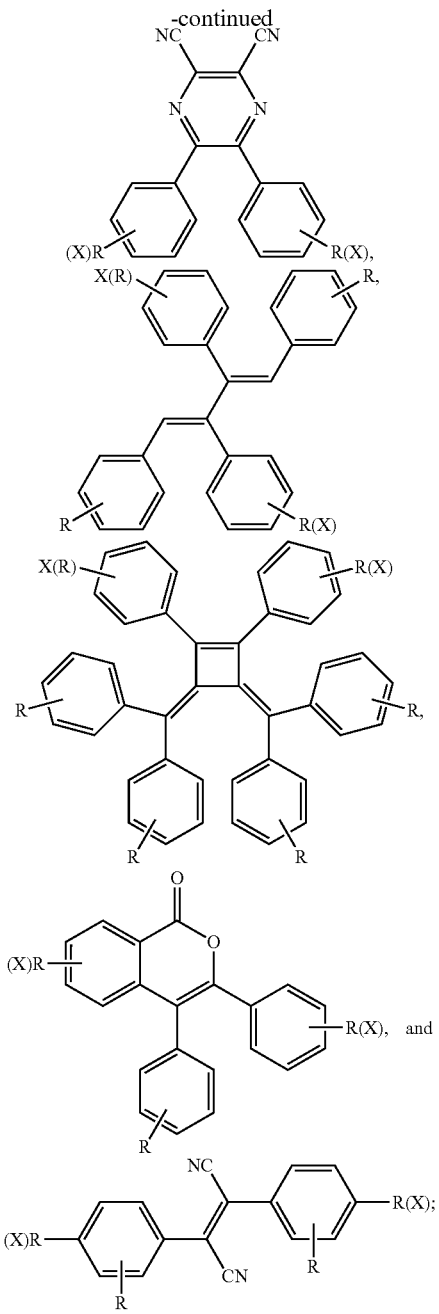

wherein at least one of R, R', R", and R'" is

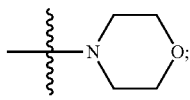

and wherein R, R', R", and R'" are independently selected from the group consisting of

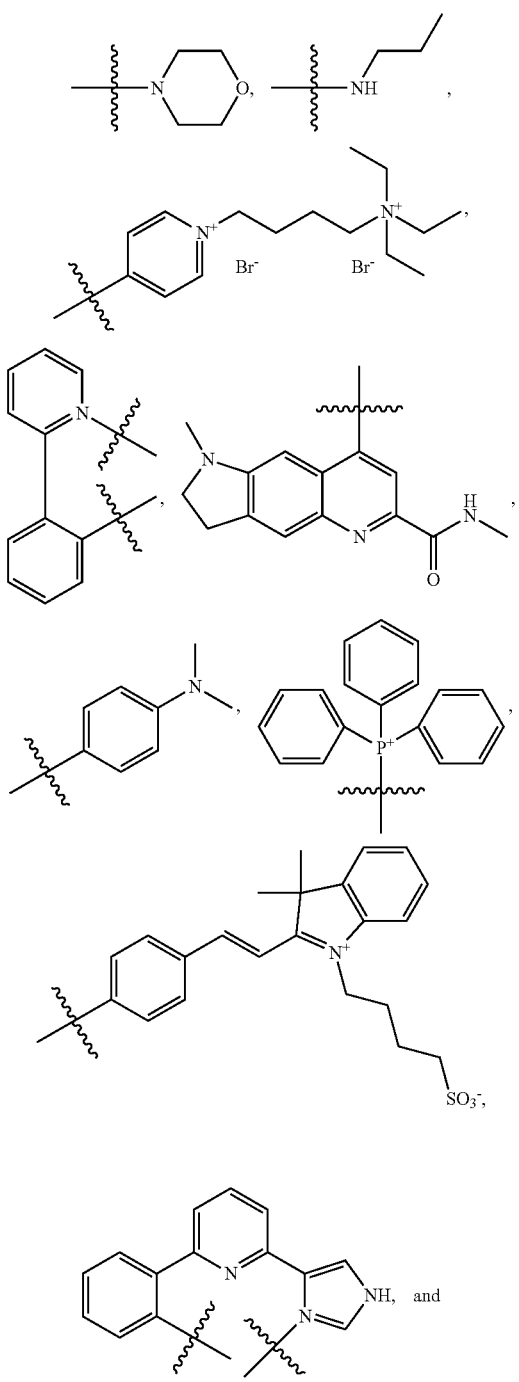

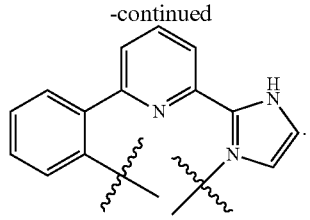

An embodiment of the present subject matter is directed to a method of lysosome imaging and autophagy process visualization comprising: introducing the AIEgen of the present subject matter to a sample; and imaging lysosomes and visualizing the autophagy process by observing fluorescence of the AIEgen, activated by the AIEgen entering and accumulating lysosomes through protonation and alternation of permeability.

In an embodiment, the lysosomes are lysosomes of living mammalian cells. In an embodiment, the AIEgen is incubated with living mammalian cells. In an embodiment, fluorescence images of the AIEgen incubated with living mammalian cells are visualized by at least one of a fluorescence microscope and a confocal microscope.

In an embodiment, the present subject matter is directed to an AIEgen for lysosome imaging comprising: a morpholine-functionalized AIE Derivative having the chemical structure of

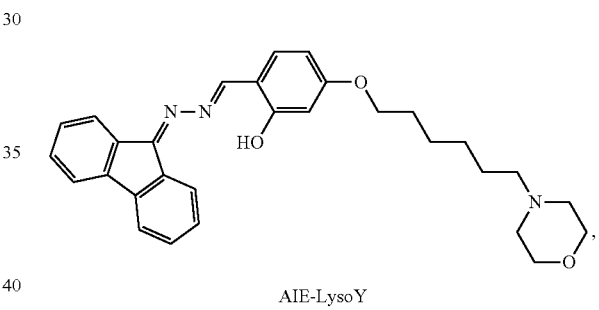

AIE-LysoY

A Highly Fluorescent ATE-Active Theranostic Agent with Anti-Tumor Activity

The challenges of meeting the expectations of desired target products complicate drug discovery efforts. However, in an embodiment of the present subject matter, after examining the chemical structure of TMX, a structural analog (TPE-TMX) of TPE has drawn interest due to its fluorogenic features.

In an embodiment of the present subject matter, TPE-TMX, bearing a phenyl group in place of the ethyl group, has been designed and synthesized for cell imaging and anti-tumor therapy. Due to its novel fluorogenic features, the drug distribution can be accurately visualized in biological settings. Moreover, excellent photostability and long-term tracing allow its working mechanism to be monitored successfully. Its similar chemical structure to TMX gives it the ability of effectively treating specific breast cancer cells, such as MCF-7 cells. Unlike the commonly accepted mechanism of TMX, TPE-TMX shows a new possible pathway of treating breast cancer cells, providing new insights of drug development.

Unlike conventional fluorogens, TPE molecules are non-emissive when molecularly dissolved, but highly emissive when aggregated, i.e., exhibit AIE behavior. The restriction of intramolecular rotations is the main cause for this. Phenyl rings in TPE undergo active intramolecular rotations in dilute solutions, causing fast, non-radiative decay of the excited states and quenching the fluorescence. In the aggregates, these motions are blocked by intermolecular steric interaction, opening the radiative pathway that leads to strong fluorescent emission. By taking advantage of these features, a series of TPE derivatives was developed and applied in many biological applications.

Thus, in an embodiment of the present subject matter, by having a phenyl substituent in place of the ethyl group without any other modification in TMX, TPE-TMX is a theranostic agent for the treatment of ER+ breast cancer. In this regard, theranostics, an integrated therapeutic system, combines diagnostic and therapeutic modalities into one system. This integration of diagnostic imaging capability with therapeutic interventions allows the drug to be targeted and monitored together with other advantages such as assessing drug distribution, release, and evaluation of drug response and efficacy, all in a non-invasive and real-time fashion.

As such, the TPE-TMX dye possesses high specificity for DNA synthesis, superior photostability, and high resistance to photobleaching. Because of the aforementioned advantages, the dye may monitor the process of DNA synthesis.

TPE-TMX was synthesized according to the synthetic route shown below:

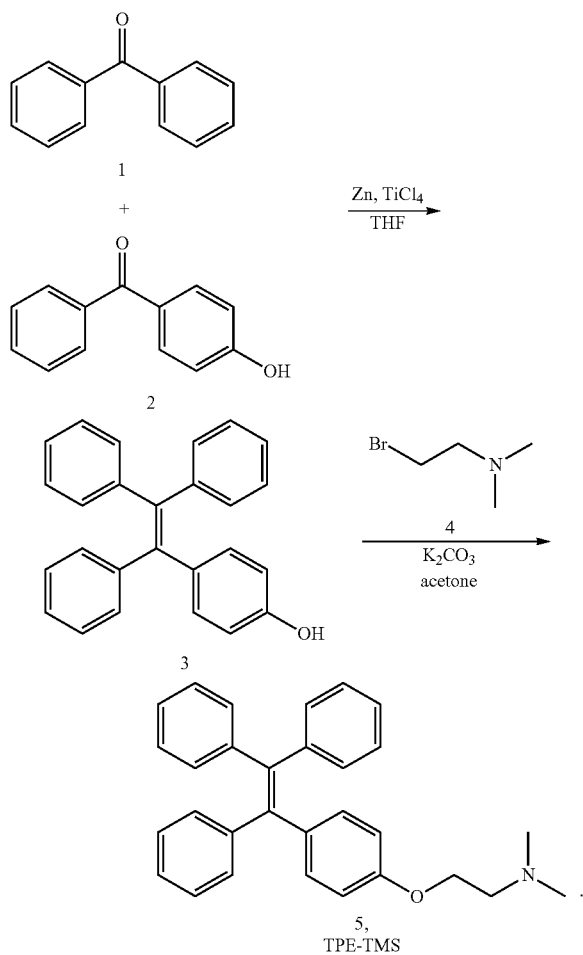

Figure 29:
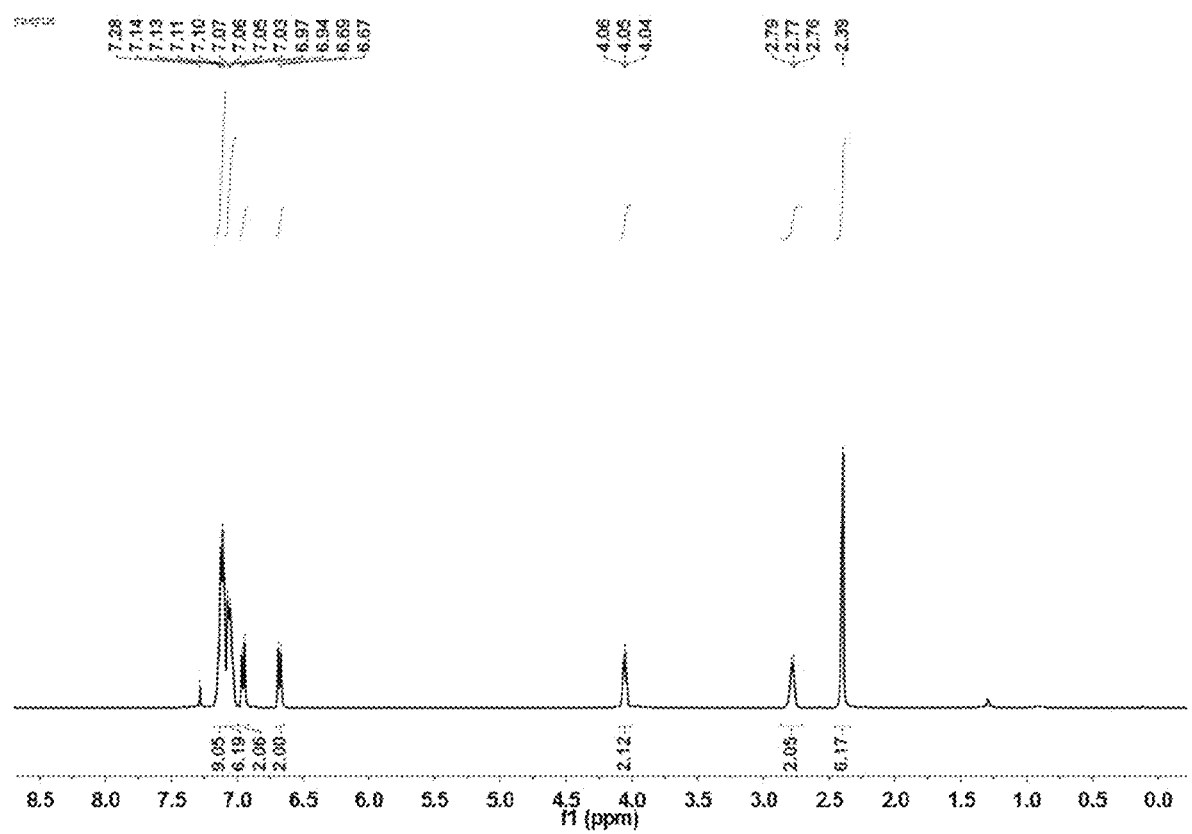
FIG. 29 shows $^1$H-NMR spectrum of TPE-TMX in CDCl$_3$-d$_6$.
Figure 30:
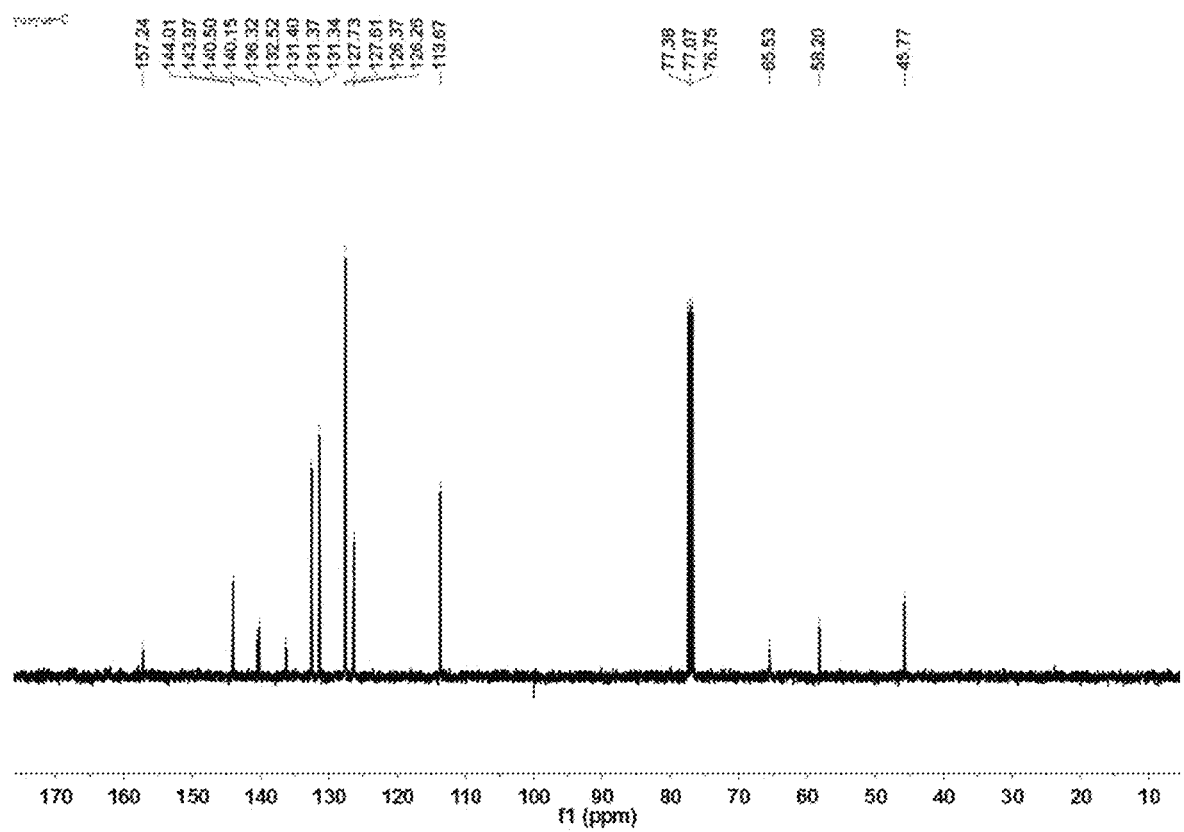
FIG. 30 shows $^{13}$C-NMR spectrum of TPE-TMX in CDCl$_3$-d$_6$.
Figure 31:
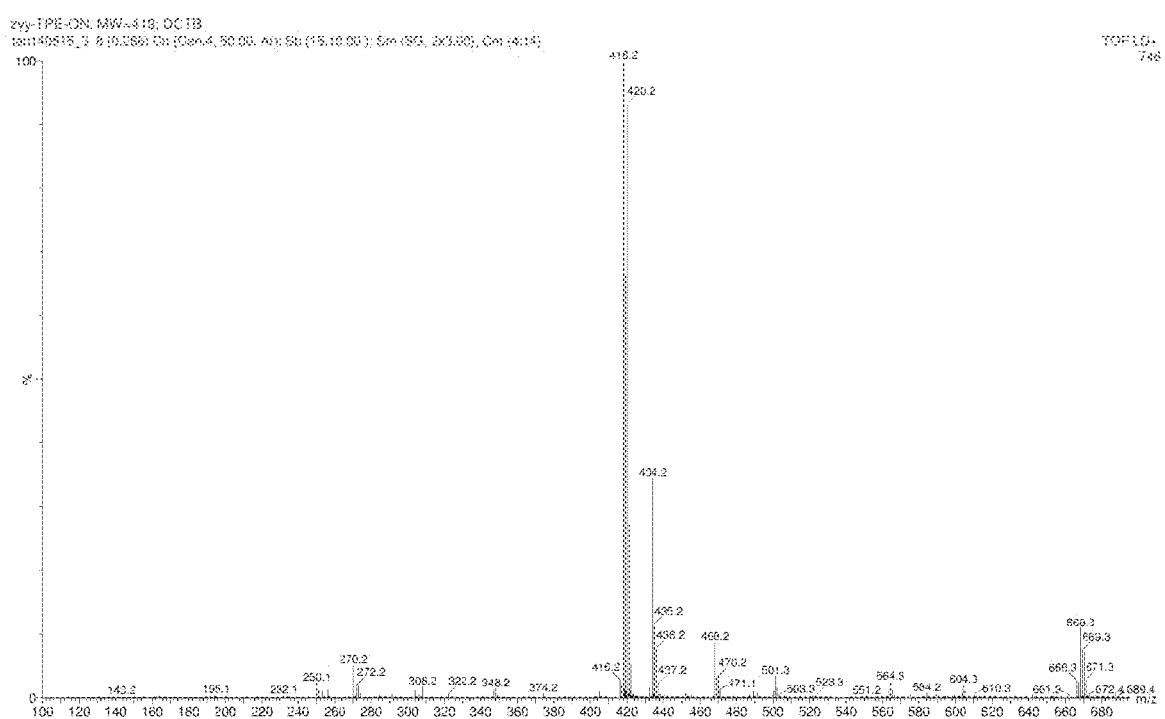
FIG. 31 shows mass spectrum of Cy-Py-N$_3$.
Figure 32:
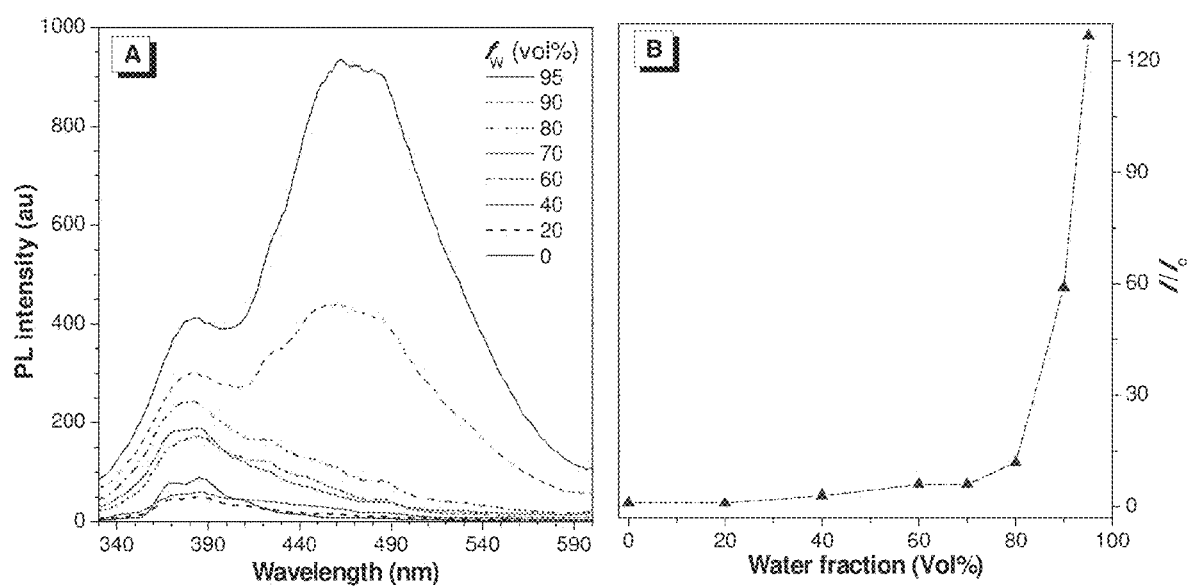
FIG. 32A-B shows (A) PL spectra of TPE-TMX in THF/water mixtures with different water fractions ($f_w$) and (B) a plot of (I/I$_0$) values versus the compositions of the aqueous mixtures of TPE-TMX. $I_0$=PL intensity in pure THF solution. [TPE-TMX]=10 μM; excitation wavelength=320 nm.

The final product was fully characterized by HRMS, $^1$H NMR, $^{13}$C NMR spectroscopies, from which satisfactory results corresponding to its structure were obtained (FIG. 29-31). The optical properties of TPE-TMX were studied, and the photoluminescence (PL) spectra of TPE-TMX in THF solutions is shown in FIG. 32A-B. The emission maxima of TPE-TMX in THF solution is located at 478 nm.

In an embodiment, other fluorescent bioprobes with ATE characteristics can be used for treating as well as imaging anti-tumor activity of specific breast cancers. In some embodiments of the bioprobes, the fluorescence of imaging comes from the lysosomes in cells that uptake AIE fluorogens. In other embodiments of the bioprobes, AIE fluorogens are composed of amino functional groups. In another embodiment, the cells are selected from any kind of cell. In another embodiment, only specific breast cancer cells are affected by treating with the bioprobes. Furthermore, the imaging samples can be cancer cells such as HeLa cells, MCF-7, Cos 7, and MDA-MB-231. In some embodiments, the ATE fluorogens comprises a backbone structure of a formula selected from the group consisting of:

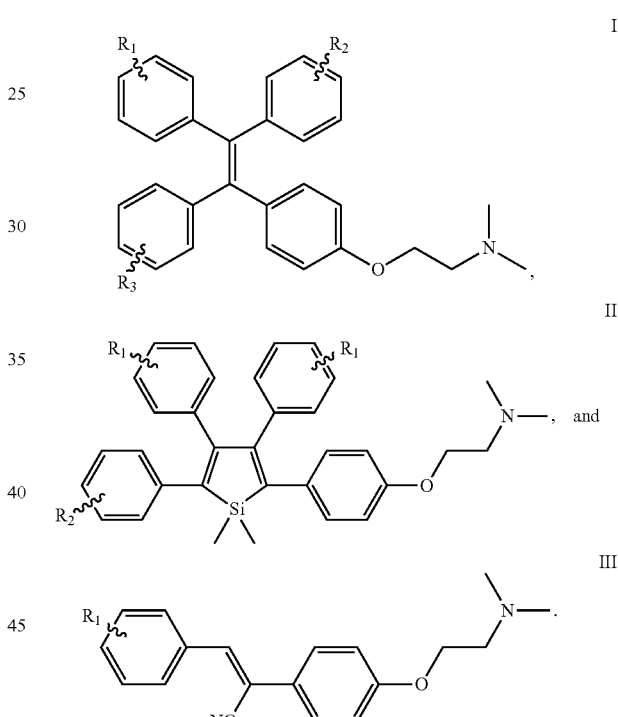

wherein $R_1$, $R_2$ and $R_3$ are substituents independently selected from the group consisting of H, alkyl, unsaturated alkyl, heteroalkyl, cycloalkyl, heterocycloalkyl, aryl, and heteroaryl.

An embodiment of the present subject matter relates to a method of anti-tumor activity in vitro comprising steps of treating cells with AIE theranostic probes and detecting cellular imaging by fluorescent microscopy or confocal laser scanning microscopy. In some embodiments of the method of imaging cells in vitro, fluorescent microscopy or confocal laser scanning microscopy techniques can be utilized for living cell tracking.

In some embodiments, amino-functionalized fluorescent probes with AIE characteristics are used for anti-tumor activity. In some embodiments of the theranostic bioprobes, AIE fluorogens are composed of amino functional groups that can be applied in treating specific breast cancer cells.

In an embodiment, the present subject matter is directed to a fluorescent bioprobe for treating and imaging anti-tumor activity comprising: AIE fluorogens comprising amino functional groups and having a chemical structure selected from the group consisting of:

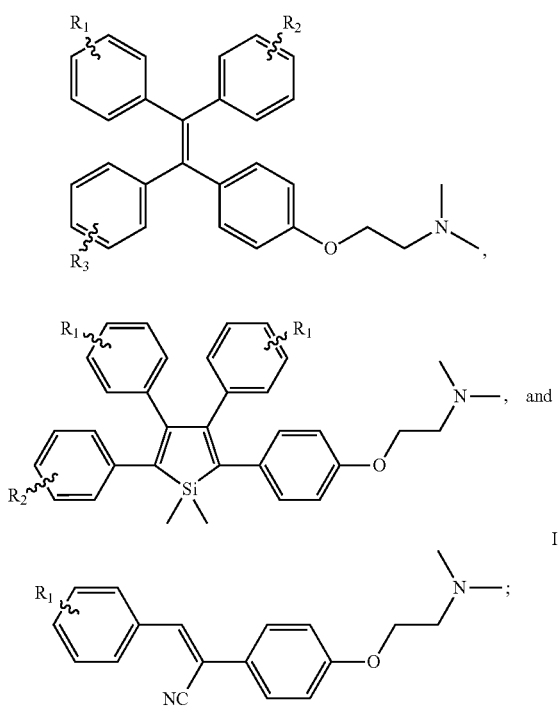

wherein $R_1$, $R_2$, and $R_3$ are independently selected from the group consisting of H, alkyl, unsaturated alkyl, heteroalkyl, cycloalkyl, heterocycloalkyl, aryl, and heteroaryl.

In an embodiment, the bioprobe of the present subject matter is used for treating as well as imaging anti-tumor activity of specific breast cancers. In an embodiment, fluorescence of imaging comes from lysosomes in cells that uptake the AIE fluorogens. In an embodiment, the cells are selected from any kind of cell. In an embodiment, breast cancer cells are affected by treatment with the fluorescent bioprobe.

An embodiment of the present subject matter is directed to a method of treating and imaging anti-tumor activity comprising: introducing the bioprobe of the present subject matter to a sample containing cells; and detecting cellular imaging by fluorescent microscopy or confocal laser scanning microscopy wherein fluorescence is emitted by probes uptaken by cells and accumulated in mitochondria.

In an embodiment, the sample comprises cancer cells selected from the group consisting of HeLa, MCF-7, Cos 7, and MDA-MB-231. In an embodiment, the sample contains living cells and fluorescent microscopy or confocal laser scanning microscopy is used for tracking the living cells.

AIE Luminogens for Biosensor Applications

An embodiment of the present subject matter is directed to the investigation of two fluorescent dyes TetraThienylEthene (TTE) and TetraFurylEthene (TFE) having AIE features. A new mechanism responsible for the enhancement of the photoluminescence that occurs when going from the aggregation condition to the crystal state was discovered, known as the cluesteroluminogenic effect. Analyzing the crystal structures of the molecules, heteroatom to heteroatom (Sulfur to Sulfur and Oxygen to Oxygen) interactions have been found. These interactions are responsible for formation of clusters, creating a more conjugated network where an emission red shift when going from the aggregation to the crystal is observed. The mechanism behind the AIE phenomenon of TTE and TFE is due to the Restriction of Intramolecular Rotations (RIR), which has been proven by synthesizing fully locked TTE (fl-TTE) and fully locked TFE (fl-TFE).

Thus, an embodiment of the present subject matter is directed to the synthesis of the locked structures of fully locked TTE (fl-TTE) and fully locked TFE (fl-TFE). These molecules display interesting behavior. Although both are ACQ dyes, they are able to emit in powder. For this reason, they may be defined as "non-conventional ACQ luminophores". In order to fully understand this effect, crystal structure analysis is needed. Since these molecules, like their unlocked parent compounds TTE and TFE, own the heteroatoms, the cluesteroluminogenic effect could also be involved in their solid state luminescence.

TTE, TFE, and fl-TFE have been tested as bioprobes for cancer cell visualization. In particular TTE has been tested in HeLa and lung cancer cells A549, and TFE and fl-TFE have been tested only in HeLa cells. Only TTE has revealed to be useful for this purpose, since it has been the only one able to enter inside the cells even though it does not have any functional group attached to its backbone. TTE is a molecule described in an embodiment of the present subject matter, and the semi locked-TTE (sl-TTE) is the intermediate product of the photo-oxidative reaction of TTE. This molecule has shown reversible photochromic properties in the solid state, the phenomenon has been described by photographs taken at different times.

In an embodiment, the present subject matter is directed to a probe for cancer cell imaging and staining comprising AIE luminogens having a chemical backbone structure selected from the group consisting of:

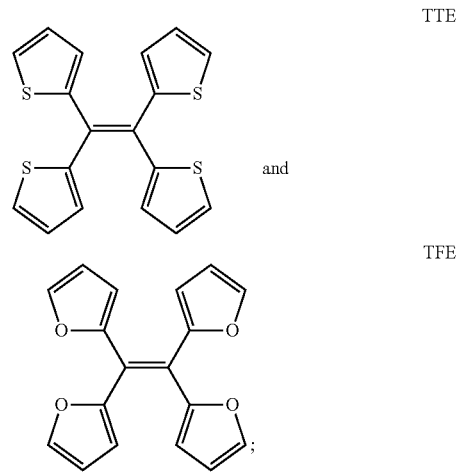

wherein the AIE luminogens are clusteroluminogens; and wherein TTE serves as a dye for cancer cell imaging. In an embodiment, TTE enters the cancer cell, selectively stains lipid droplets, and has a blue-green emission.

In an embodiment, the present subject matter is directed to luminophores having a chemical structure consisting of:

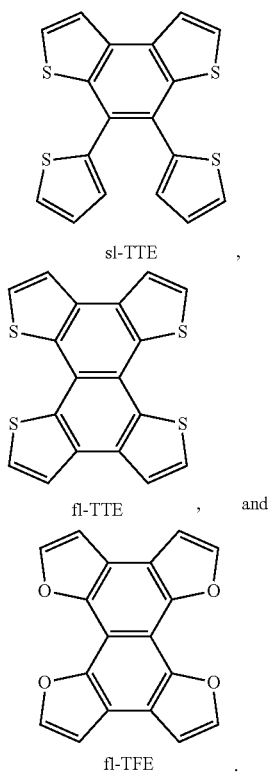

sl-TTE , fl-TTE , and fl-TFE .

In an embodiment, the luminophores are non-conventional ACQ luminophores and emit luminescence in a powder state. In an embodiment, fl-TTE is the non-conventional ACQ luminophore. In an embodiment, fl-TTE has a red shift emission from a solution of pure THF to an aggregation condition in a solution of 1 vol % THF 99 vol % water. In an embodiment, sl-TTE has AIE and ACQ properties. In an embodiment, sl-TTE displays solid state photochromic ability.

In an embodiment, the present subject matter is directed to a probe for cancer cell imaging and staining comprising AIE luminogens having a chemical structure of:

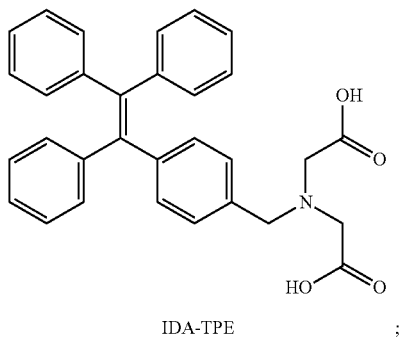 [SMILES: O=C(O)CN(CC(=O)O)Cc1ccc(C(=C(c2ccccc2)c2ccccc2)c2ccccc2)cc1]

IDA-TPE ;

wherein the AIE luminogens are uptaken by cancer cells and images show organelles inside the cancer cells are stained. In an embodiment, the organelles stained are mitochondria.

EXAMPLES

The following examples are given to illustrate specific applications of the present subject matter. The examples are not intended to limit the scope of the present subject matter described in this application.

Example 1

Characterization: Steady-state fluorescence spectra were recorded on a Perkin Elmer LS 55 spectrometer. Fluorescent images were collected on Olympus BX 41 fluorescence microscope.

Cell culture: HeLa cells were cultured in the MEM containing 10% FBS and 1% antibiotics (100 units/mL penicillin and 100 g/mL streptomycin) in a 5% $CO_2$ humidity incubator at 37° C. COS-7, MDA-MB-231, MCF-7, and MDCK-II cells were culture in the DMEM containing 10% FBS and antibiotics (100 units/mL penicillin and 100 g/mL streptomycin) in a 5% $CO_2$ humidity incubator at 37° C.

Cell imaging: two different kind of cells were grown overnight on a 35 mm petri dish with a cover slip. The live cells were incubated with 200 nM of TPE-IQ-2O for 1, 5, 10, and 20 mins. In a typical experiment, 2 µL of a 10 mM stock solution of TPE-IQ-2O in DMSO was diluted to 2 mL with cell culture medium, followed by further dilution to desired concentration. The cells were imaged under a fluorescent microscope (BX41 Microscope) using the same excitation and emission filters: excitation filter=400-440 nm, dichroic mirror=455 nm, and emission filter=465 nm long pass.

The PC-9, HepG2, and HCC827 cells were grown overnight on a 35 mm petri dish with a cover slip. The live cells were incubated with 200 nM of TPE-IQ-2O for 20 and 10 mins. In all the experiments, the cancer cells are fluorescent in solely staining.

The LX2 cells were grown overnight on a 35 mm petri dish with a cover slip. The live cells were incubated with 200 nM of TPE-IQ-2O for 20 and 10 mins. In all the experiments, the normal cells have no obvious fluorescence.

The HeLa cells were grown overnight on a 35 mm petri dish with a cover slip. Then the HeLa cells were stained with 200 nM TPE-IQ-2O and Mito-tracker red (50 nM)/Lyso-tracker red (50 nM)/DAPI (500 nM) for 20 mins. It indicates TPE-IQ-2O can selectively target the mitochondria of cells.

Synthetic Routes for Structure I, II, III, and IV:

A sealed tube containing 2.0 mol %[RhCp*$Cl_2$]$_2$, 0.30 mmol $AgBF_4$, 0.30 mmol $Cu(OAc)_2$, 0.36 mmol different benzaldehydes and internal 0.30 mmol alkyne was evacuated and purged with nitrogen gas three times. Then, 0.45 mmol propylamine and 2.5 mL t-amyl alcohol were sequentially added to the system via syringe under a nitrogen atmosphere and the reaction mixture was allowed to stir at 110° C. for 3 hrs. When the reaction was complete, the mixture was cooled and diluted with 10 mL $CH_2Cl_2$. The mixture was filtered through a Celite pad and further washed with 30 mL $CH_2Cl_2$ and 20 mL MeOH. The combined filtrate was concentrated in rota-evaporator and the residue was purified by $Al_2O_3$ column chromatography using $CH_2Cl_2$/MeOH (100:1 v/v) as eluent to give pure product structure of I, II, III, and IV as an orange solid in yield from 50% to 80%.

Preparation of 6-(2,2-bis(4-methoxyphenyl)-1-phenylvinyl)-3,4-diphenyl-2-propylisoquinolin-2-ium (Structure I, TPE-IQ-2O)

A sealed tube containing 2.0 mol %[RhCp*$Cl_2$]$_2$, 0.30 mmol $AgBF_4$, 0.30 mmol $Cu(OAc)_2$, 0.36 mmol 4-(2,2-bis (4-methoxyphenyl)-1-phenylvinyl)benzaldehyde and internal 0.30 mmol alkyne was evacuated and purged with nitrogen gas three times. Then, 0.45 mmol propylamine and 2.5 mL t-amyl alcohol were sequentially added to the system via syringe under a nitrogen atmosphere and the reaction mixture was allowed to stir at 110° C. for 3 hrs. When the reaction was complete, the mixture was cooled and diluted with 10 mL $CH_2Cl_2$. The mixture was filtered through a Celite pad and further washed with 30 mL $CH_2Cl_2$ and 20 mL MeOH. The combined filtrate was concentrated in rota-evaporator and the residue was purified by $Al_2O_3$ column chromatography using $CH_2Cl_2$/MeOH (100:1 v/v) as eluent to give pure product TPE-IQ-2O as an orange solid in 79.10% yield.

Figure 2:
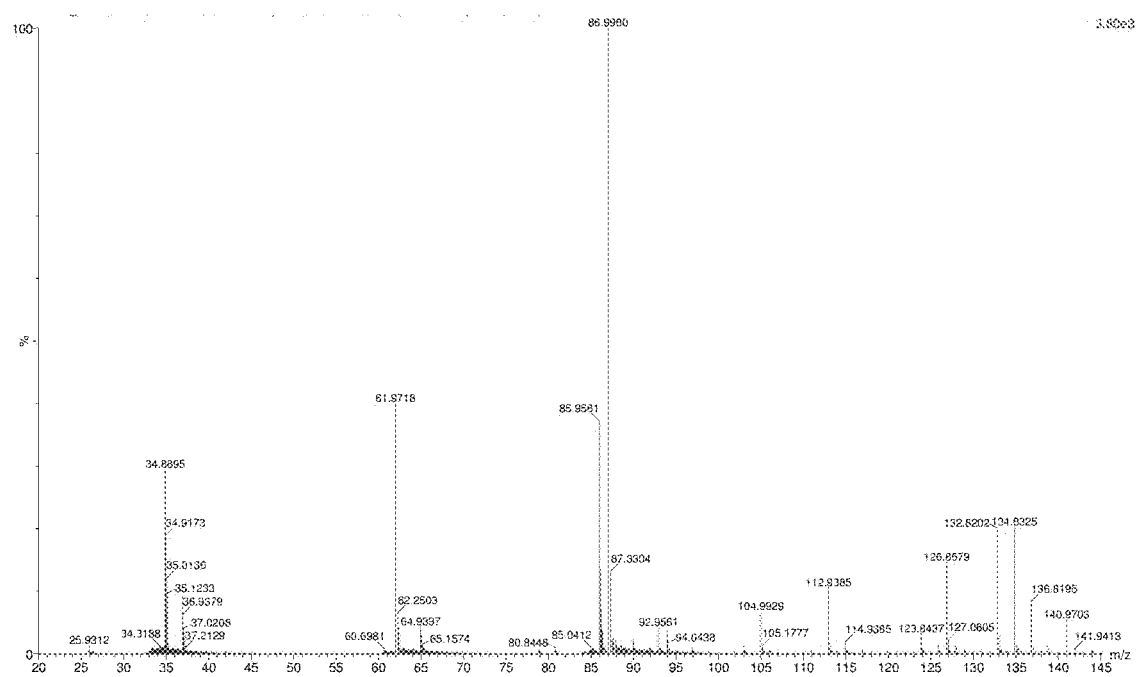
FIG. 2 shows mass spectrum of TPE-IQ-2O's negative ion.

$^1$H NMR (400 MHz, $CDCl_3$), δ (TMS, ppm): 11.35 (s, 1H), 8.66 (d, 1H), 7.53 (d, 2H), 6.58-7.31 (m, 21H), 4.73 (m, 4H), 3.72 (s, 3H), 3.81 (s, 3H), 1.90 (d, 2H), 0.87 (m, 3H). $^{13}$C NMR (100 MHz, $CDCl_3$), δ (TMS, ppm): 159.12, 159.06, 154.64, 151.12, 145.46, 143.42, 142.73, 138.23, 137.40, 137.04, 135.07, 134.98, 134.60, 133.09, 133.03, 132.89, 131.61, 131.54, 131.10, 130.46, 130.21, 130.16, 128.88, 128.46, 128.44, 128.36, 127.26, 125.96, 114.03, 113.25, 60.27, 55.55, 55.31, 25.59, 10.97. MALDI-TOF: m/z (cation): 638.3088 (M+, calcd: 638.3059), m/z (anion): 86.9980 (M+, calcd: 87.0035). Characterization data, proton and carbon NMR (FIG. 1), MALDI-TOF for Cation (exact mass: 638.3054) and MALDI-TOF for Anion (FIG. 2).

TPE-IQ-2O shows typical ATE features, as shown in FIG. 3. The THF solution of TPE-IQ-2O was almost non-emissive, while the aggregation state of 90% hexane fraction emits strong luminescence at about 620 nm upon the UV excitation.

Hela Cell and COS-7 Normal Cell:

Two different kinds of cells were grown overnight on a 35 mm petri dish with a cover slip. The live cells were incubated with 200 nM of TPE-IQ-2O for 20, 10, 5, and 1 mins. The Hela cells were stained by TPE-IQ-2O; the COS-7 cells were stained by TPE-IQ-2O; the Hela cells and COS-7 cells were co-cultured and stained together by TPE-IQ-2O. Condition: 200 nM (Filter: both close; Channel 5; EX: 400-440 nm; Exposure time: bright field: 1000 ms Fluorescence: 1000 ms.

In all the experiments, the Hela cancer cell is fluorescent in solely staining. There is no emission, and the normal cells COS-7 are not stained by TPE-IQ-2O. However, when both cells are grown in the same environment and followed by the staining process, there is fluorescence only from the Hela cancer cell.

MCF-7 Cell and COS-7 Normal Cell:

Two different kinds of cells were grown overnight on a 35 mm petri dish with a cover slip. The live cells were incubated with 200 nM of TPE-IQ-2O for 20, 10, and 5 mins. The MCF-7 cells were stained by TPE-IQ-2O; the COS-7 cells were stained by TPE-IQ-2O; the MCF-7 cells and COS-7 cells were co-cultured and stained together by TPE-IQ-2O. Condition: 200 nM (Filter: both close; Channel 5; EX: 400-440 nm; Exposure time: bright field: 1000 ms Fluorescence: 1000 ms.

In all the experiments, the MCF-7 cancer cell is fluorescent in solely staining. There is no emission and the normal cell COS-7 is not stained by TPE-IQ-2O. However, when both cells are grown in the same environment and followed by the staining process, there is fluorescence only from the MCF-7 cancer cell.

MDA-MB-231 Cell and COS-7 Normal Cell:

Two different kinds of cells were grown overnight on a 35 mm petri dish with a cover slip. The live cells were incubated with 200 nM of TPE-IQ-2O for 20, 10, 5, and 1 mins. The MDA-MB-231 cells were stained by TPE-IQ-2O; the COS-7 cells were stained by TPE-IQ-2O; the MDA-MB-231 cells and COS-7 cells were co-cultured and stained together by TPE-IQ-2O. Condition: 200 nM (Filter: both close; Channel 5; EX: 400-440 nm; Exposure time: bright field: 1000 ms Fluorescence: 1000 ms.

In all the experiments, the MDA-MB-231 cancer cell is fluorescent in solely staining. There is no emission and the normal cell COS-7 is not stained by TPE-IQ-2O. However, when both cells are grown in the same environment and followed by the staining process, there is fluorescence only from the MDA-MB-231 cancer cell.

Hela Cell and MDCK-II Normal Cell:

Two different kinds of cells were grown overnight on a 35 mm petri dish with a cover slip. The live cells were incubated with 200 nM of TPE-IQ-2O for 10 mins. The Hela cells were stained by TPE-IQ-2O; the MDCKII cells were stained by TPE-IQ-2O; the MDA-MB-231 cells and COS-7 cells were co-cultured and stained together by TPE-IQ-2O. Condition: 200 nM 10 mins (Filter: both close; Channel 5; EX: 400-440 nm; Exposure time: bright field: 1000 ms Fluorescence: 1000 ms.

In all the experiments, the Hela cancer cell is fluorescent in solely staining. There is no emission and the normal cell MDCK-II is not stained by TPE-IQ-2O. However, when both cells are grown in the same environment and followed by the staining process, there is fluorescence only from the Hela cancer cell.

ROS Generation:

Fluorescence change of TPE-IQ-2O, H2DCF-DA (ROS indicator) and the mixture with different irradiation time of white light. The mixture of TPE-IQ-2O and H2DCA display increased intensity which was detected by PL machine, which indicates the continuous ROS generation (FIG. 20). Dye (TPE-IQ-2O): 10 mM; H2DCF-DA: 5 mM. Excitation wavelength: 488 nm.

Figure 21:
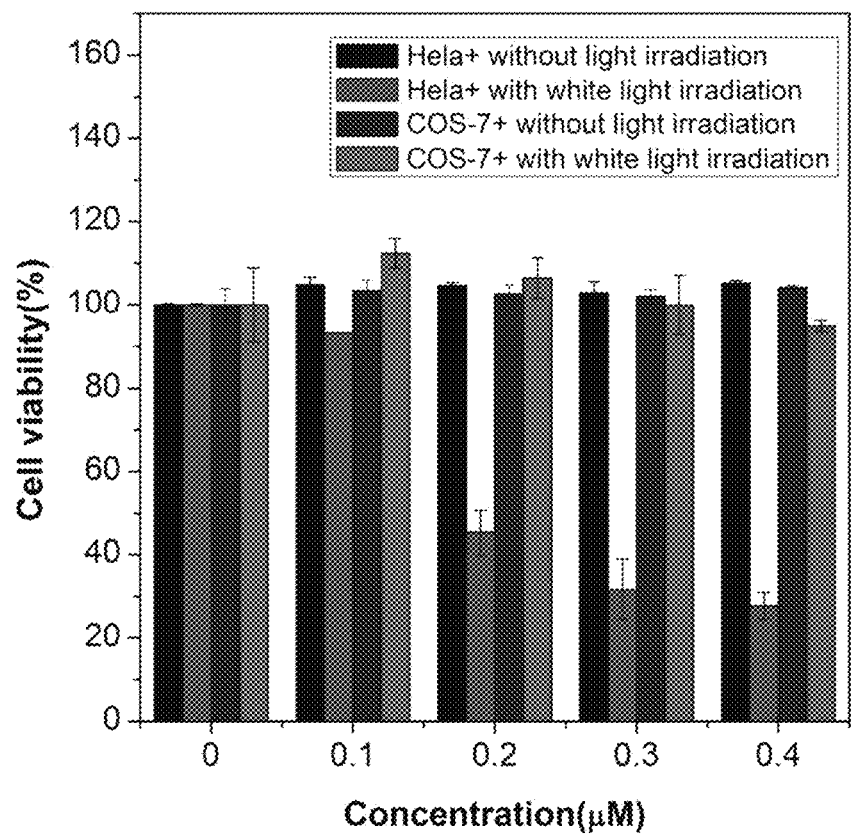
FIG. 21 shows the LDH assay of TPE-IQ-2O. With white light irradiation for 90 mins, HeLa cells decreased as the concentration of TPE-IQ-2O increased, while no obvious cytotoxicity was observed in HeLa cells without white light irradiation, COS-7 cells with or without white light irradiation.
Figure 22:
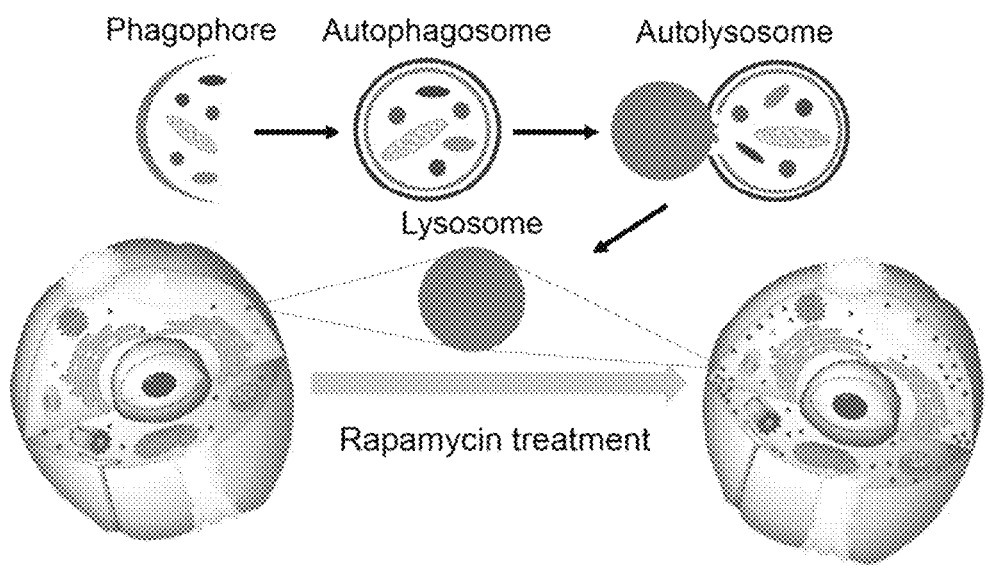
FIG. 22 shows a schematic presentation of an autophagy process and rapamycin treatment.

LDH Cytotoxicity Assay of Cancer and Normal Cells:

The HeLa and COS-7 cells were seeded in 96-well plate for 24 hrs. Then a different concentration of TPE-IQ-2O was added into each well. After 30 mins TPE-IQ-2O treatment in the dark, the dye was removed. Half of the cells were treated with white light irradiation for 90 mins and the rest of cells were kept in the dark. After another 24 hrs of incubation, 10 μL of 10× lysis buffer bromide was added to untreated cells as Maximum LDH Activity, while 10 μL ultrapure water was added to other wells. After incubation at 37° C. 5% $CO_2$ for 45 mins, 50 μL of each well sample medium was transferred to a new 96-well plate, followed by addition of 50 μL reaction mixture. 50 μL stop solution were added into each well after 30 mins incubation protected from light. Then the absorbance was achieved by plate reader. With white light irradiation for 90 mins, HeLa cells decreased as the concentration of TPE-IQ-2O increased, while no obvious cytotoxicity was observed in HeLa cells without white light irradiation, COS-7 cells with or without white light irradiation (FIG. 21).

Example 2

Preparation of Structure II (DPA-IQ):

Briefly, a reaction mixture of [RhCp*$Cl_2$]$_2$ (2.0 mol %), $AgBF_4$ (0.30 mmol), Cu(OAc)$_2$ (0.30 mmol), 4-(diphenylamino)benzaldehyde (0.36 mmol), diphenylacetylene (0.30 mmol), propylamine (0.45 mmol) in 2.5 ml t-amylalcohol were heated and stirred under nitrogen at 110° C. for 3 hrs. After removal of the solvent, the resident were purified by alumina column chromatography using CH$_2$Cl$_2$/MeOH (100:1 v/v) as eluent to give pure product as a yellow solid in 60% yield.

$^1$H-NMR (400 MHz; d$_6$-DMSO) δ$_H$ 9.77 (s, 1H), 8.29 (d, 2H, J=9.6 Hz), 7.44-7.36 (m, 10H), 7.30-7.24 (m, 6H), 7.11-7.10 (m, 3H), 7.04-7.02 (m, 2H), 6.43 (s, 1H), 4.18 (t, 2H, J=7.2 Hz), 1.75-1.69 (m, 2H), 0.73 (t, 2H, J=7.2 Hz) ppm. $^{13}$C-NMR (400 MHz; CDCl$_3$) δ$_C$ 155.0, 149.1, 144.4, 143.3, 139.7, 135.4, 133.7, 133.6, 131.5, 130.4, 130.2, 130.0, 128.8, 128.2, 128.1, 127.0, 126.8, 123.5, 122.1, 109.5, 59.3, 25.3, 10.9 ppm. $^{11}$B-NMR −1.327 ppm. $^{19}$F-NMR −148.3 ppm. MALDI-MS calculated for cation of DPA-IQ (C$_{36}$H$_{31}$N$_2^+$): 491.2482, found: 491.2494.

Figure 5:
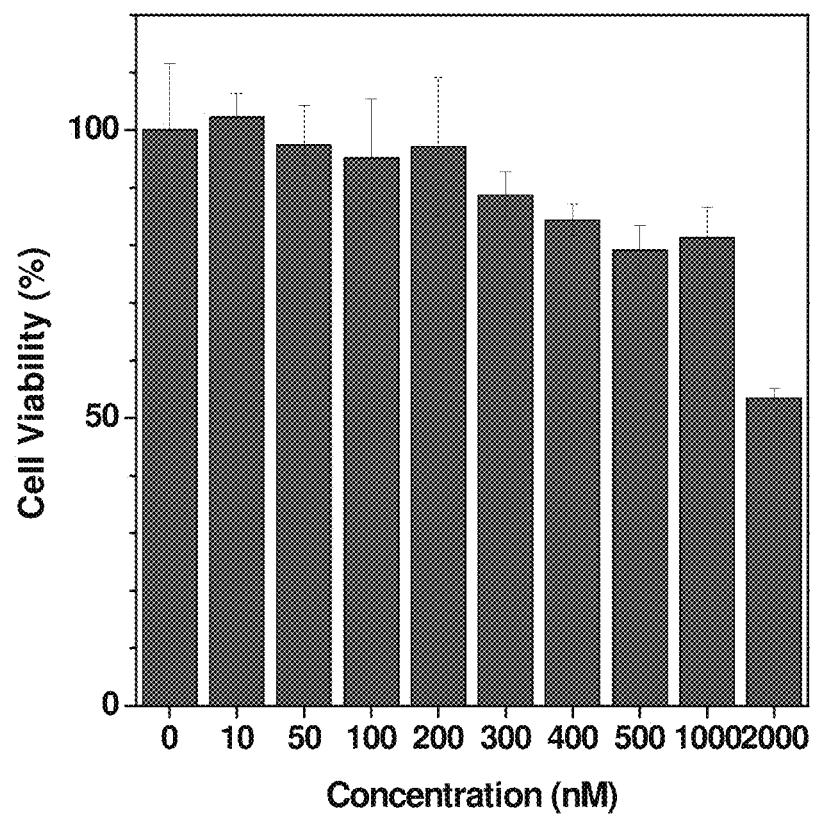
FIG. 5 shows cell viability tested by MTT assay: Hela cells were incubated with different concentrations of DPA-IQ in culture medium for 24 hrs.

DPA-IQ shows typical AIE features. The DMSO solution of DPA-IQ was almost non-emissive while the aggregation state powder of this material emits strong green luminescence upon the UV excitation. The UV absorption is shown in FIG. 4. Results show DPA-IQ can stain the mitochondrial organelle as good as the commercially available MitoTracker Red FM with low cytotoxicity confirmed by MTT assay (FIG. 5). With different working concentrations, DPA-IQ can work from 50 nM to 500 nM, as all of the tested concentrations have demonstrated a high resolution staining for mitochondria.

Figure 6:
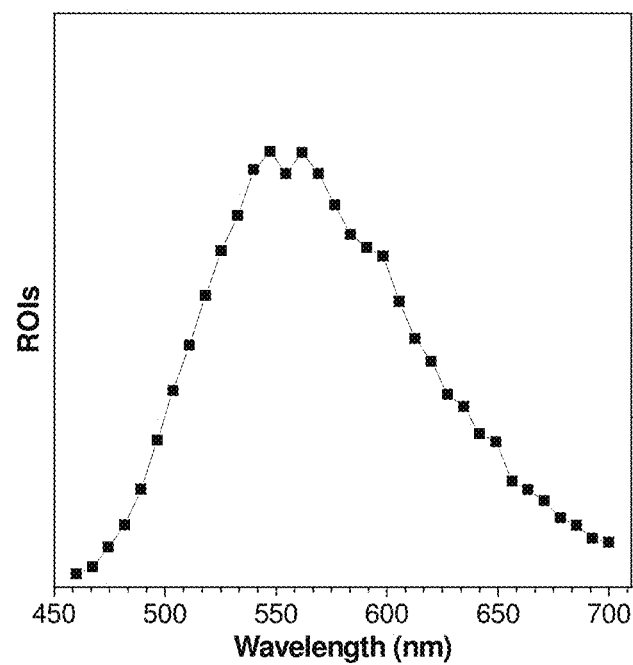
FIG. 6 shows a plot of emission wavelength scanning from 460 nm to 700 nm with a bandwidth of 15 nm. Excited with 442 nm laser.

DPA-IQ has the ability to absorb two-photon and the results show a high resolution of the staining part of a cancer cell. FIG. 6 shows plot of emission wavelength scanning from 460 nm to 700 nm with a bandwidth of 15 nm. Excited with 442 nm laser.

Figure 7:
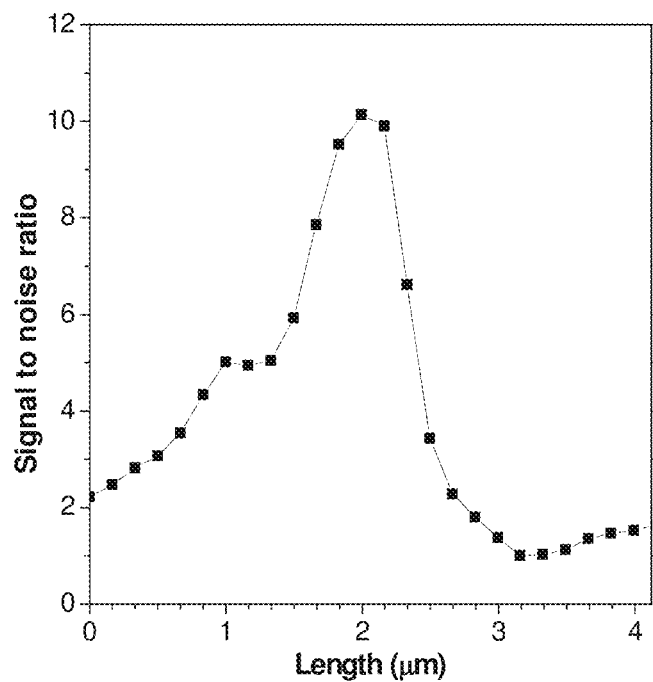
FIG. 7 shows S/N ratio of DPA-IQ in the Hela cells. Hela cells were stained with 50 nM DPA-IQ in PBS for 10 min. Excited with 442 nm laser.
Figure 8:
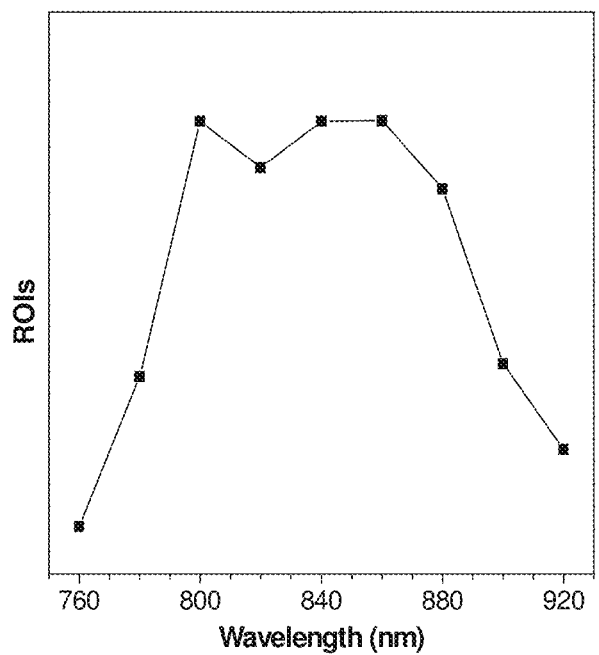
FIG. 8 shows a plot of ROIs versus excitation wavelengths. Hela cells were stained with 50 nM DPA-IQ in PBS for 10 min.

The Signal to noise ratio (S/N) is acceptable, as shown in FIG. 7, which is the S/N ratio of DPA-IQ in the Hela cells. Hela cells were stained with 50 nM DPA-IQ in PBS for 10 min. Excited with 442 nm laser) and different two-photon excitations are tested in FIG. 8, which shows a plot of ROIs versus excitation wavelengths. Hela cells were stained with 50 nM DPA-IQ in PBS for 10 min.

A clear image can be yielded when the two-photon excitation wavelength is chosen by 780, 800, 840, 860, 880, and 900 nm. As compared with the single photon excitation, the S/N ratio between two technique and the results show that there are almost no differences between both excitation methods, which indicate that due to the high quality of the two-photon excitable dye, it may be used for in vivo imaging, as shown in FIG. 9.

Hela/HepG2/PC-9 Cell and LX2 Normal Cell:

HepG2 cells (human hepatocarcinoma cell line), PC-9 cells (human lung adenocarcinoma cell line), Hela cells (human cervical carcinoma cell line), and LX2 cells (normal cell, human hepatic stellate cell line) were stained with 200 nM DPA-IQ for 10 min. Images were taken under the same equipment settings. Scale bar: 30 μm. Excitation wavelength: 400-440 nm. Results show that the cancer cells show strong emission and the normal healthy cell LX2 shows faint emission.

Example 3

Preparation of Structure III (TPA-IQ):

Synthetic procedures are similar to DPA-IQ.

$^1$H-NMR (400 MHz; d$_6$-DMSO) δ$_H$ 10.29 (s, 1H), 8.66 (d, 1H, J=8.8 Hz), 8.43 (d, 1H, J=8.4 Hz), 7.60-7.58 (m, 3H), 7.49 (s, 2H), 7.40-7.28 (m, 12H), 7.15-7.08 (m, 6H), 7.00 (d, 2H, J=8.4 Hz), 4.36 (t, 2H, J=7.2 Hz), 1.85-1.80 (m, 2H), 0.79 (t, 3H, J=7.2 Hz) ppm. $^{13}$C-NMR (400 MHz; d$_6$-DMSO) δ$_C$ 149.3, 149.1, 147.7, 146.3, 144.3, 137.9, 137.7, 133.5, 131.4, 131.1, 130.4, 130.3, 130.1, 130.0, 129.8, 128.7, 128.5, 128.3, 125.5, 125.2, 124.3, 121.6, 120.8, 60.0, 23.7, 10.5 ppm. $^{11}$B-NMR (128 MHz; d$_6$-DMSO) −1.32 ppm. $^{19}$F-NMR (376 MHz; d$_6$-DMSO) −148.3 ppm. MALDI-MS calculated for cation of TPA-IQ (C$_{42}$H$_{35}$N$_2^+$): 567.2795, found: 567.2771.

TPA-IQ shows typical AIE features, as shown in FIG. 10. The DMSO solution of TPA-IQ was almost non-emissive while the aggregation state powder of this material emits yellowish orange luminescence upon the UV excitation. The UV absorption is shown in FIG. 10.

Figure 11:
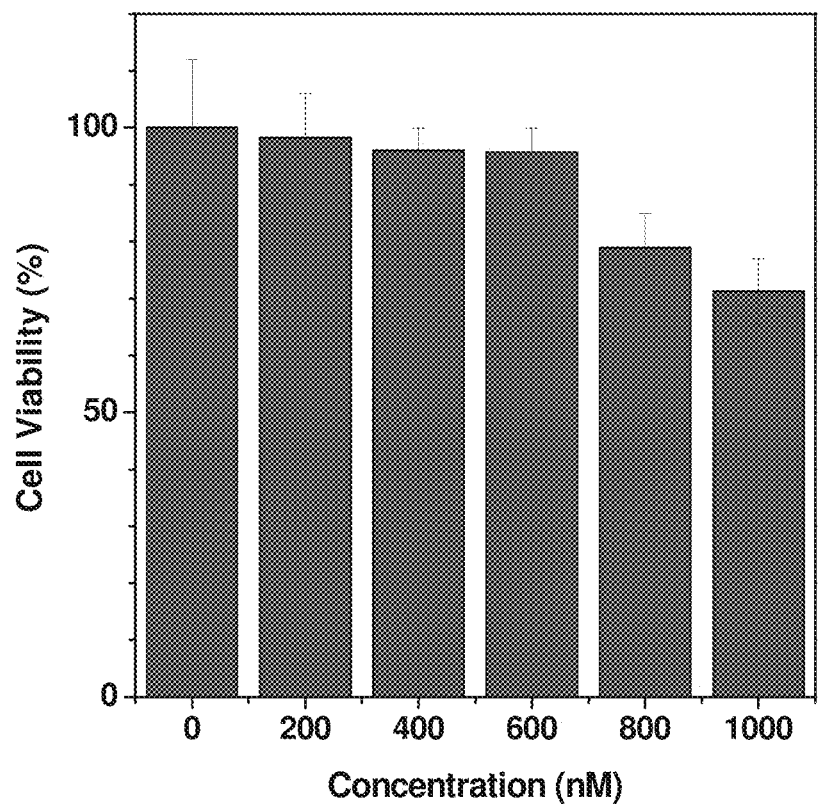
FIG. 11 shows cell viability tested by MTT assay of Hela cells incubated with different concentrations of TPA-IQ in culture medium for 24 hrs.

TPA-IQ can stain the mitochondrial organelle as well as the commercially available MitoTracker Red FM with higher resolution and low cytotoxicity, as confirmed by MTT assay (FIG. 11).

With different working concentrations, TPA-IQ can work from 200 nM to 1000 nM, as all of the tested concentrations demonstrated a high resolution staining for mitochondria.

Figure 12:
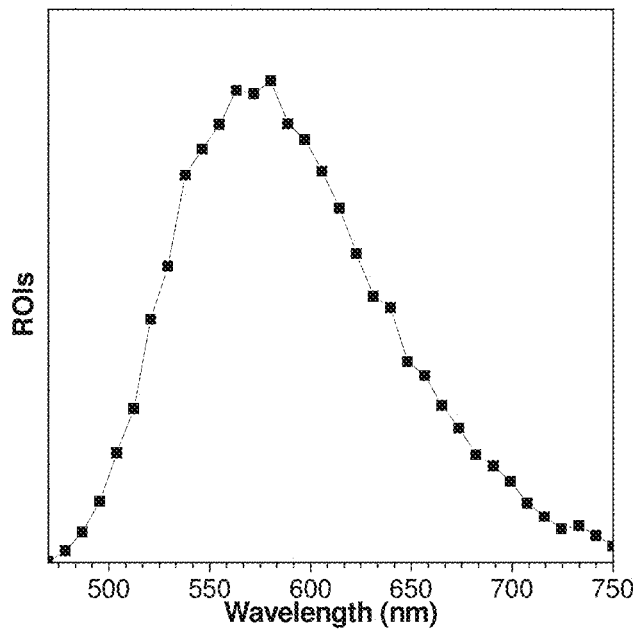
FIG. 12 shows a plot of emission wavelength scanning from 470 nm to 750 nm with a bandwidth of 15 nm. Excited with 442 nm laser.

To utilize the non-linear photon absorption property of the triphenylamine group of TPA-IQ, TPA-IQ has the ability to absorb two-photon and results can show a high resolution of the staining part of a cancer cell. FIG. 12 shows a plot of emission wavelength scanning from 470 nm to 750 nm with a bandwidth of 15 nm (Excited with 442 nm laser). The Signal to noise ratio (S/N) is acceptable, as FIG. 13 shows the S/N ratio of Naph-IQ in the Hela cells. Hela cells were stained with 400 nM TPA-IQ in PBS for 10 min. Excited with 442 nm laser. The S/N ratio between two techniques and the results show that the two photon absorptivity is decreased as the scanning time is increased, shown in FIG. 14.

Example 4

Preparation of Structure IV (Naph-IQ):

Synthetic procedures are similar to DPA-IQ.

$^1$H-NMR (400 MHz; d$_6$-DMSO) δ$_H$ 10.35 (s, 1H), 8.75 (d, 1H, J=8.8 Hz), 8.30-8.26 (m, 2H), 7.73 (d, 1H, J=8.0 Hz), 7.60-7.42 (m, 9H), 7.30-7.24 (m, 5H), 7.10 (d, 1H, J=8.0 Hz), 4.43 (t, 2H, J=7.2 Hz), 4.01 (s, 3H) 1.89-1.84 (m, 2H), 0.82 (t, 3H, J=7.2 Hz) ppm. $^{13}$C-NMR (400 MHz; d$_6$-DMSO) δ$_C$ 155.8, 149.7, 148.9, 144.4, 138.2, 137.4, 133.5, 133.3, 130.8, 130.4, 130.1, 129.3, 128.8, 128.4, 128.2, 127.7, 126.0, 125.7, 124.1, 122.3, 104.4, 60.3, 55.9, 23.8, 10.5 ppm. $^{11}$B-NMR (128 MHz; d$_6$-DMSO) −1.33 ppm. $^{19}$F-NMR (376 MHz; d$_6$-DMSO) −148.3 ppm. MALDI-MS calculated for cation of Naph-IQ (C35H30NO+): 480.2322, found: 480.2334.

Figure 15:
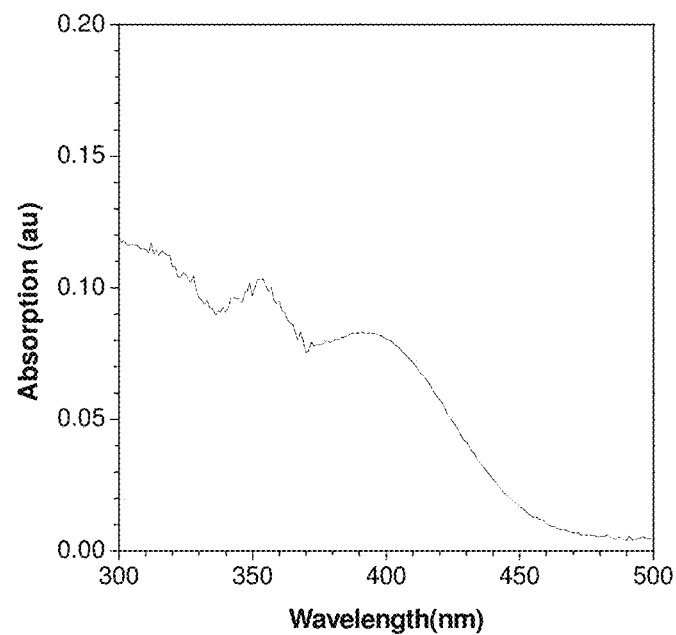
FIG. 15 shows absorption spectra of Naph-IQ in DMSO (10 μM).

Naph-IQ shows typical AIE features. The DMSO solution of TPA-IQ was almost non-emissive while the aggregation state powder of this material emits blue luminescence upon the UV excitation. The UV absorption is shown in FIG. 15.

Figure 16:
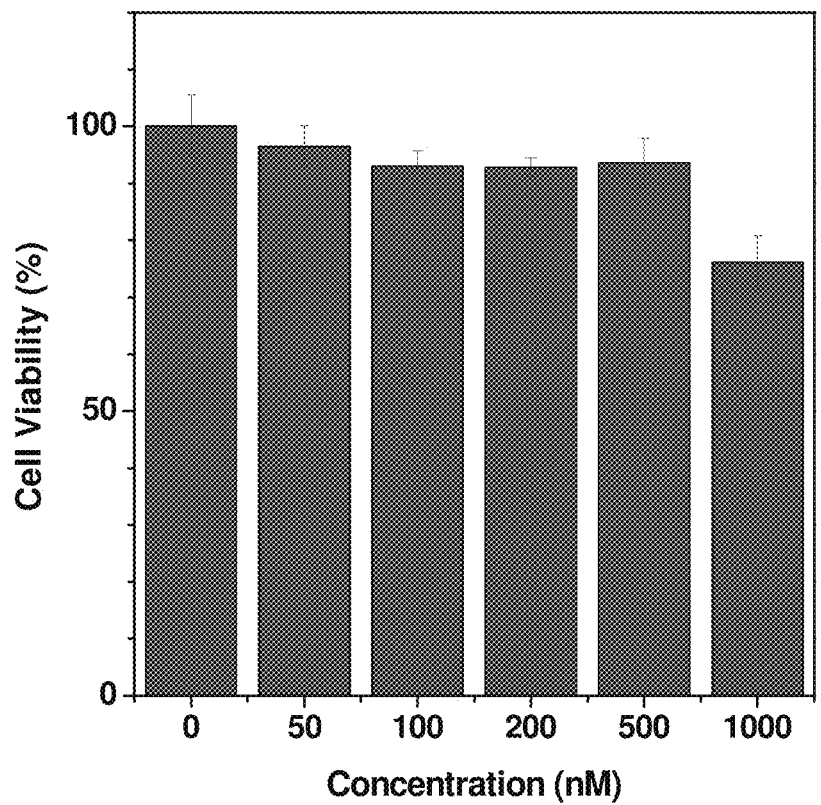
FIG. 16 shows cell viability tested by MTT assay. Hela cells were incubated with different concentrations of Naph-IQ in culture medium for 24 hours.

The commercially available MitoTracker Red FM is co-stained as a control together with Naph-IQ. The result shows Naph-IQ can stain the mitochondrial organelle as good as MitoTracker Red FM with higher resolution and low cytotoxicity confirmed by MTT assay (FIG. 16). With different working concentrations, Naph-IQ can work from 50 nM to 500 nM, as all of the tested concentrations have demonstrated a high resolution staining for mitochondria.

Figure 17:
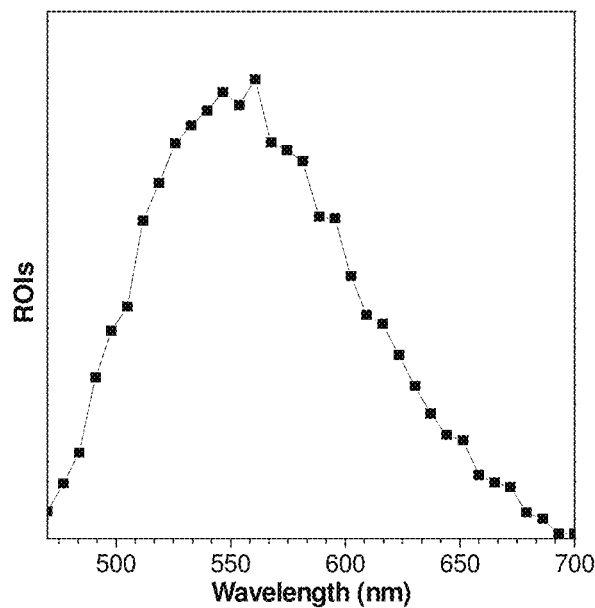
FIG. 17 shows a plot of emission wavelength scanning from 460 nm to 700 nm with a bandwidth of 15 nm. Excited with 442 nm laser.
Figure 18:
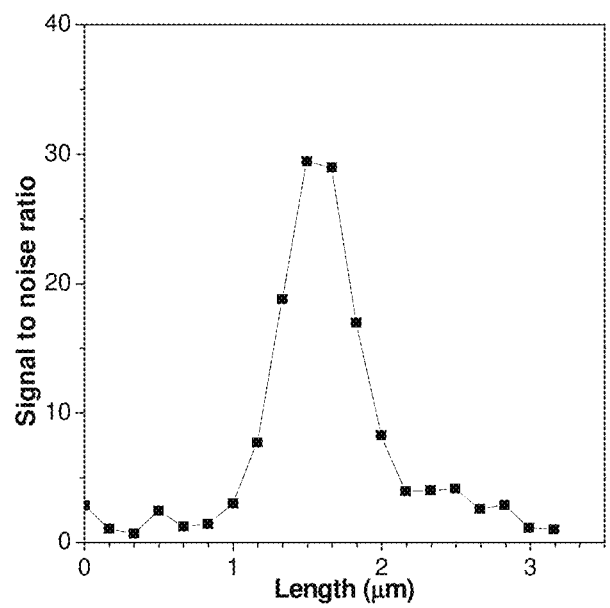
FIG. 18 shows S/N ratio of Naph-IQ in the Hela cells. Hela cells were stained with 200 nM Naph-IQ in PBS for 10 min. Excited with 442 nm laser.

Naph-IQ has the ability of two-photon absorption and the results can show a high resolution of the staining part of a cancer cell. FIG. 17 shows a plot of emission wavelength scanning from 460 nm to 700 nm with a bandwidth of 15 nm (Excited with 442 nm laser). The Signal to noise ratio (S/N) is acceptable, as FIG. 18 shows the S/N ratio of Naph-IQ in the Hela cells. Hela cells were stained with 200 nM Naph-IQ in PBS for 10 min. Excited with 442 nm laser. Also, the S/N ratio between two techniques and the results show that the two photon absorptivity is decreased as the scanning time is increased, shown in FIG. 19.

Example 5

The synthetic route to AIE-LysoY is shown below:

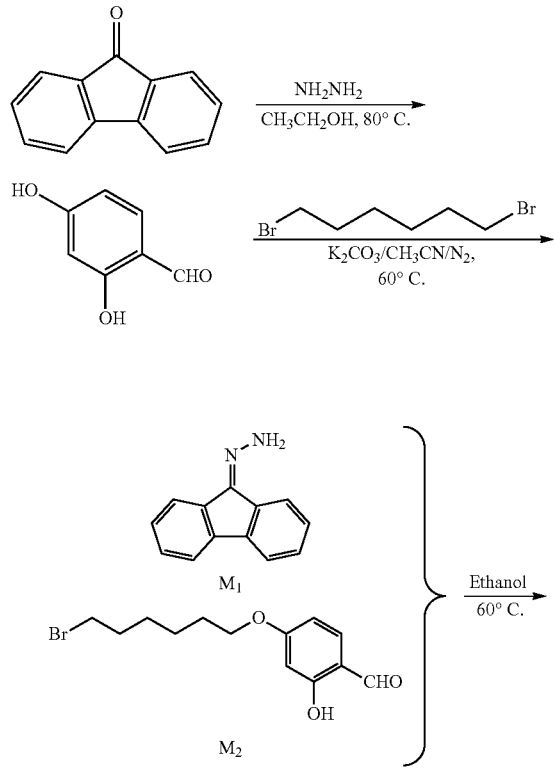

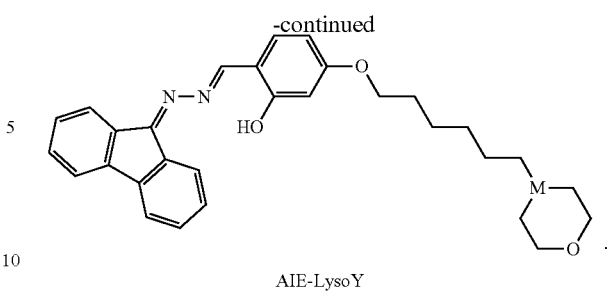

AIE-LysoY

M1 and M2 were prepared by one-step modification of commercially available precursors, which then underwent condensation under mild reaction conditions to yield FAS-Br. AIE-LysoY was obtained by conjugating FAS-Br with a morpholine group. The morpholine group with moderate alkalinity is employed for lysosome-targeting. Once entering the lysosome, the morpholine will be protonated, due to the high acidity of lysosome, which endows AIE-LysoY with higher hydrophilicity and lysosomal retention. In this way, lysosome is selectively lighted up by AIE-LysoY.

AIE-LysoY exhibits an absorption band peaked at 390 nm in THF (FIG. 23). It emits faintly when molecularly dissolved in THF with a small emission band centered at 565 nm. With an increase in water fraction of the THF/water mixtures (FIG. 24A, PL spectra of AIE-LysoY in THF/water mixtures with different water fractions ($f_w$)), AIE-LysoY becomes highly emissive (FIG. 24B), demonstrating a novel phenomenon of AIE. The AIE effect of AIE-LysoY can be rationalized by the activation of RIM and ESIPT upon formation of nanoaggregates. In pure THF solution, AIE-LysoY can undergo dynamic intramolecular motions, thus excitons nonradiatively decay in these solutions. In a solvent mixture with low solvating power, AIE-LysoY form nanoaggregates, and thus its intramolecular motion is prohibited. As a result, the excitons of AIE-LysoY decay through the radiative pathway of fluorescence and emission is enhanced.

AIE-LysoY also possess the characteristics of ESIPT. It demonstrates two kinds of emission:

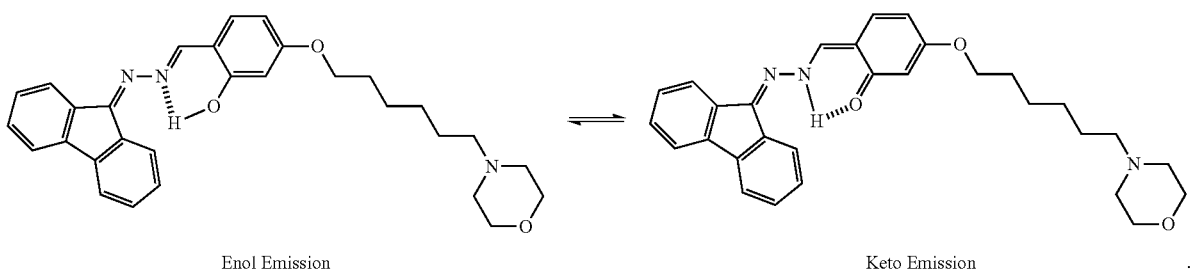

Enol Emission                                    Keto Emission

-continued

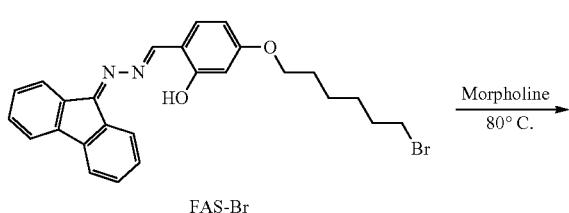

FAS-Br

Figure 25:
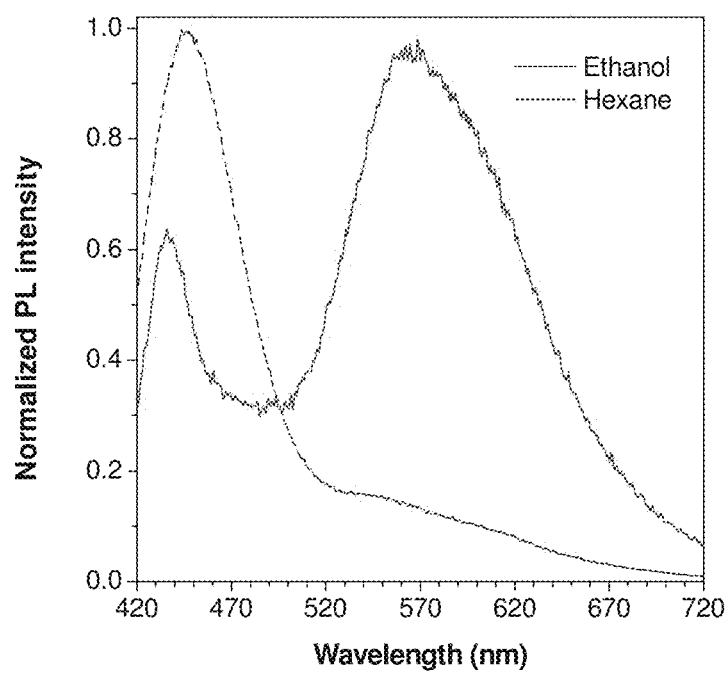
FIG. 25 shows normalized PL spectra of AIE-LysoY in ethanol and hexane. Concentration=10 μM; $\lambda_{ex}$=390 nm.
Figure 26:
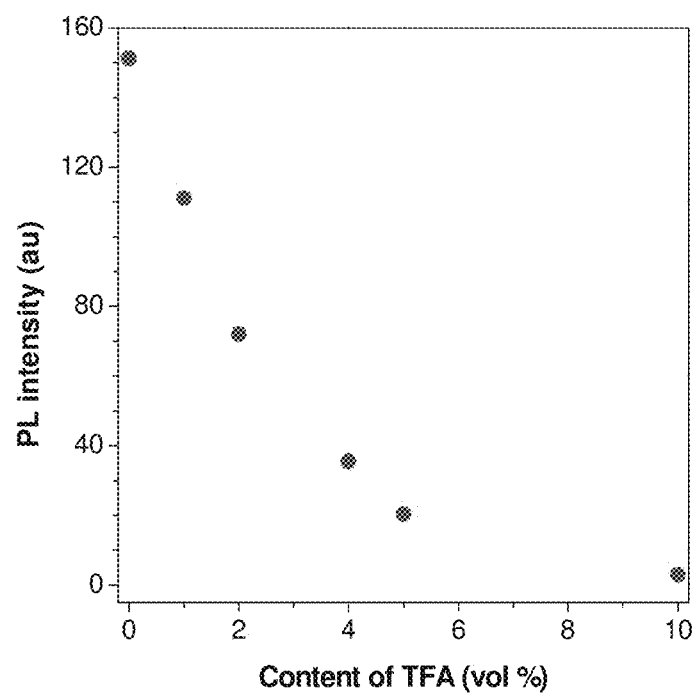
FIG. 26 shows PL intensities in THF/water mixtures of AIE-LysoY with different TFA fractions. Concentration=10 μM; $\lambda_{ex/em}$=390/565 nm.

In aprotic solvent, the intramolecular hydrogen bond exits, thus it demonstrates keto emission with a longer wavelength. It demonstrates enol emission with a shorter wavelength in protic solvent, due to the breakage of such intramolecular hydrogen bond (FIG. 25). External addition of organic acid can also break the intramolecular hydrogen bond and lead to decreased keto emission intensity. To demonstrate this, a strong organic acid, trifluoroacetic acid (TFA), with pKa of about −0.3, is added into the aggregate suspension (THF/water, 1:99) of AIE-LysoY. The emission of AIE-LysoY at 565 nm decreased dramatically when TFA fraction is increased from 1% to 5%. At a TFA fraction of 10%, AIE-LysoY becomes completely nonemissive (FIG.

26). This is because the central nitrogen is protonated with the addition of TFA, and ESIPT emission can no longer occur.

The scheme of synthesis of AIE-LysoY is as follows:

(9H-fluoren-9-ylidene) hydrazine (M1)

9H-fluoren-9-one (5.0 g, 27.75 mmol) was dissolved in absolute ethanol (70 ml), followed by addition of hydrazine (20 mL), and the mixture was refluxed for 12 h. Precipitates were filtrated under vacuum and washed with absolute ethanol three times, then dried under vacuum to give a yellow needle crystal (5.0 g, 93% yield).

4-((6-bromohexyl)oxy)-2-hydroxybenzaldehyde (M2)

2,4-Dihydroxybenzaldehyde (5.0 g, 36.2 mmol) and 1,6-dibromohexane (8.8 g, 36.2 mmol) were first dissolved in acetonitrile (50 ml), followed by addition of $K_2CO_3$ (6.0 g, 43.4 mmol), the mixture was stirred at 60° C. under the nitrogen for 36 hrs. After cooling to room temperature, the mixture was extracted by dichloromethane (40 mL) three times. The resultant solution was washed twice with dilute HCl solution and once with water. The combined dichloromethane fractions were dried over anhydrous $MgSO_4$ and concentrated under reduced pressure. The residue was further separated by column chromatography (silica, petroleum ether/ethyl acetate=8/1) to give a white solid (2.25 g, 20.6% yield). $^1$H NMR (400 MHz, $CDCl_3$) δ=11.48 (s, 1H), 9.71 (s, 1H), 7.41 (d, J=8.7 Hz, 1H), 6.52 (dd, J=8.7, 2.3 Hz, 1H), 6.41 (d, J=2.3 Hz, 1H), 4.01 (t, J=6.4 Hz, 2H), 3.43 (t, J=6.7 Hz, 2H), 1.89-1.79 (m, 4H), 1.54-1.48 (m, 4H).

(E)-2-(((9H-fluoren-9-ylidene)hydrazono)methyl)-5-((6-bromohexyl)oxy)phenol (FAS-Br)

4-((6-bromohexyl)oxy)-2-hydroxybenzaldehyde (M2, 2.0 g, 6.64 mmol) was dissolved in absolute ethanol (30 ml), followed by addition of (9H-fluoren-9-ylidene)hydrazine (M1, 1.37 g, 7.1 mmol), and the mixture was reacted at 60° C. for 12 hrs. Precipitates were filtrated under vacuum and washed with absolute ethanol three times, then dried under vacuum. The residue was further separated by column chromatography (silica, petroleum ether/dichloromethane=1/3) to give a yellow powder solid (2.54 g, 80% yield). $^1$H NMR (400 MHz, $CDCl_3$) δ=12.08 (s, 1H), 8.71 (s, 1H), 8.27 (d, J=7.6 Hz, 1H), 7.90 (d, J=7.5 Hz, 1H), 7.61 (dd, J=17.2, 7.4 Hz, 2H), 7.50-7.38 (m, 2H), 7.38-7.24 (m, 4H), 6.57 (m, 3H), 4.03 (t, J=6.4 Hz, 2H), 3.73 (t, J=4.6 Hz, 2H), 2.46 (m, 2H), 2.35 (m, 2H), 1.94-1.66 (m, 2H), 1.53-1.39 (m, 4H).

(E)-2-(((9H-fluoren-9-ylidene)hydrazono)methyl)-5-((6-morpholinohexyl)oxy) phenol (AIE-LysoY)

(E)-2-(((9H-fluoren-9-ylidene)hydrazono)methyl)-5-((6-bromohexyl)oxy)phenol (FAS-Br, 1.0 g, 2.1 mmol) was added into morpholine (8 ml), and the mixture was refluxed under nitrogen for 4 hrs, then the mixture was dried under vacuum and extracted with dichloromethane (4 mL) three times. The extracts were washed with brine, dried over anhydrous $MgSO_4$, and concentrated under reduced pressure. The residue was further separated by column chromatography (silica, methanol/dichloromethane=1/20) to give a yellow solid (0.96 g, 95% yield). $^1$H NMR (400 MHz, CDCl3) δ=12.06 (s, 1H), 8.72 (s, 1H), 8.25 (d, J=7.6 Hz, 1H), 7.90 (d, J=7.5 Hz, 1H), 7.64 (dd, J=17.2, 7.4 Hz, 2H), 7.50-7.38 (m, 2H), 7.38-7.24 (m, 4H), 6.53 (ddd, J=51.6, 28.0, 17.0 Hz, 3H), 4.03 (t, J=6.4 Hz, 2H), 3.73 (t, J=4.6 Hz, 4H), 2.46 (s, 4H), 2.35 (m, 2H), 1.90-1.76 (m, 2H), 1.52-1.39 (m, 4H). m/z (MALDI-TOF) 484.2593 [M$^+$]; calc. 483.2522.

Application

Figure 27:
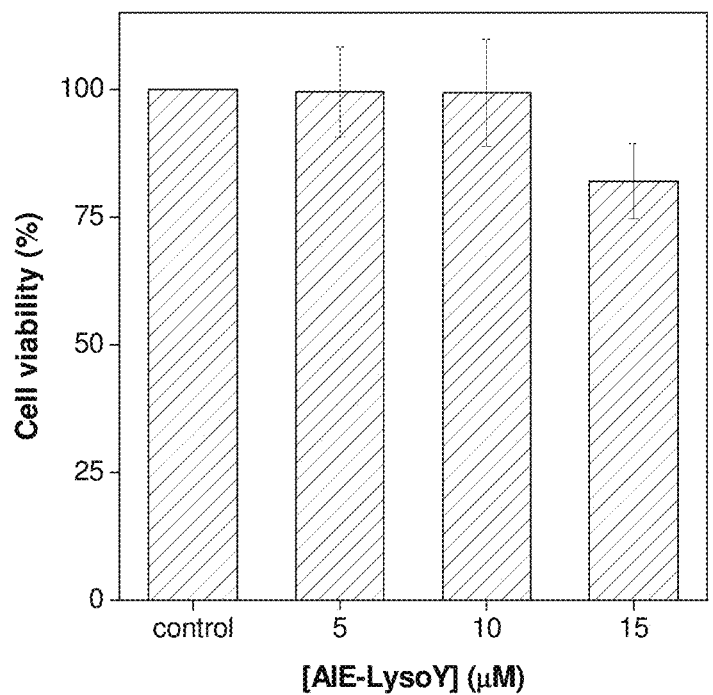
FIG. 27 shows cytotoxicity of AIE-LysoY on HeLa cells determined by MTT assay.

Before employing AIE-LysoY as a fluorescent visualizer of lysosome, a 3-(4,5-dimethyl-2-thiazolyl)-2,5-diphenyltetrazolium bromide (MTT) cell proliferation assay was first conducted to evaluate its cytotoxicity. After incubation with 15 μM of AIE-LysoY for 24 hrs, the viability of HeLa cell remains higher than 80% (FIG. 27), demonstrating that AIE-LysoY exerts little interference on cell growth. The good biocompatibility of AIE-LysoY enables its application as a fluorescent tracer to follow the autophagic process of lysosome.

Then, AIE-LysoY was applied to lysosome imaging and its lysosome-targeting performance was assessed by fluorescence microscope. HeLa cells were stained with 10 μM of AIE-LysoY for 10 min, followed by washing away the abundant molecules of AIE-LysoY and incubation with 50 nM of LTR for 30 min. AIE-LysoY selectively accumulates in the dot-shaped lysosomes and endows them with yellow emission, which can be clearly distinguished from the background. The fluorescence of AIE-LysoY overlaps perfectly with that of LTR, indicating the lysosome-targeting of AIE-LysoY.

Quantitative analysis of the degree of overlapping of these two fluorescence signals by Pearson's coefficient ($R_r$), which depicts the degree of linear dependence between two variables, gives an overlapping coefficient of 0.90. The high $R_r$ value proves that AIE-LysoY is a lysosome-selective probe. In addition, AIE-LysoY shows a higher contrast than LTR even after shorter incubation time, which can be ascribed to the bright emission and high selectivity of AIE-LysoY. Interestingly, if HeLa cells are stained with LTR in the first place and then AIE-LysoY, the latter still demonstrates higher contrast than the former. These results suggest that even if lysosome is preoccupied by LTR, AIE-LysoY can still be well internalized into lysosome due to its higher affinity toward lysosome. Additionally, AIE-LysoY also demonstrates advantageous attribute of variable staining time. Changing the staining time from 10 min to 60 min, the specificity to lysosome is retained, as well as the emission contrast.

Figure 28:
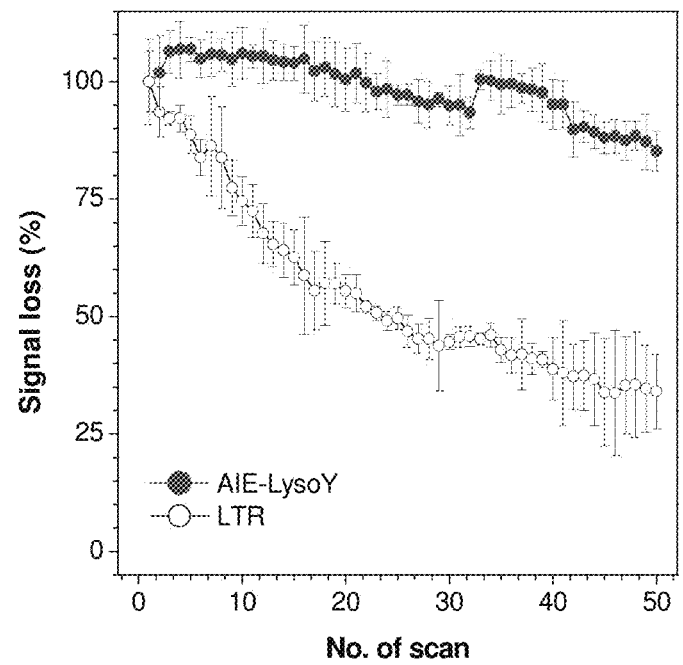
FIG. 28 shows signal loss (%) of fluorescent emission of AIE-LysoY (solid circle) and LTR (open circle) with increasing number of scans. $\lambda_{ex}$=405 nm (for AIE-LysoY) and 561 nm (for LTR); $\lambda_{em}$=468-696 nm (for AIE-LysoY) and 573-696 nm (for LTR); irradiation time: 7.75 s/scan.

Compared with LTR, the working concentration of AIE-LysoY is much higher. LTR is not more sensitive than AIE-LysoY. As mentioned previously, LTR can only be used at low concentrations to avoid the ACQ effect. At such a low working concentration, the fluorescent probes molecularly disperse in the organelle and can be easily photooxidized by continuous excitation light, resulting in the low photostability of these probes. In order to evaluate the photostability of AIE-LysoY, a confocal microscope (Zeiss laser scanning confocal microscope LSM7 DUO) was applied to continuously scan cells stained by AIE-LysoY. The photostability of LTR was also measured for comparison. The power of excitation light (405 nm for AIE-LysoY and 561 nm for LTR) were unified by using a power meter. After continuous scanning for 50 min with total irradiation time of ~6 min, the fluorescence signal from HeLa cells stained by AIE-LysoY almost remain unchanged, indicating excellent photostability (FIG. 28, solid circle line). In contrast, the fluorescence intensity from LTR dropped to lower than 50% of its initial value after only 25 scans (FIG. 28, hollow circle line). The slight fluctuation of fluorescence signal can be ascribed to the dynamic movement of lysosome in living cells. The excellent photostability of AIE-LysoY may stem from its nanoparticles nature in lysosome imaging, which can protect the chromophore inside the particles from being photooxidzied. In this way, the fluorescence of AIE-LysoR can pertain after a long-time irradiation. The good photostability of AIE-LysoY enables its potential in long-term following the biological processes of lysosome.

To design the lysosome-specific bioprobe, a molecular engineering approach was employed. The precursor of AIE-LysoY, FAS-Br, and two morpholine-functionalized AIE-gens, TPE-2Mor and Nred-mor were prepared and applied to cell imaging. The molecular structures of TPE-2mor and Nred-mor are shown below:

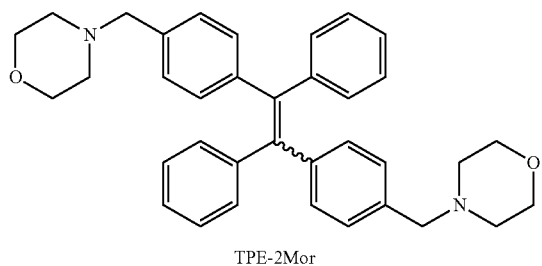

TPE-2Mor

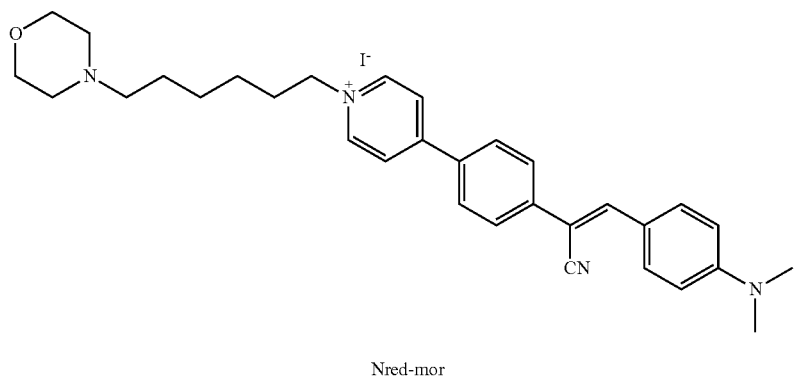

Nred-mor

FAS-Br lights up intracellular lipid droplets and the recticulum structures of mitochondria in HeLa cells rather than lysosomes, which suggests the necessity of morpholine for locating the acidic lysosomes. However, bearing a morpholine group does not guarantee lysosome selectivity. Both TPE-2Mor and Nred-mor contain morpholine groups, but neither can selectively light up lysosomes. TPE-2Mor stains all the hydrophobic regions, while Nred-mor selectively accumulates in the mitochondria. TPE-2Mor contains a hydrophobic TPE core and Nred-mor carries a charged pyridinium moiety. The hydrophobic interaction of TPE and the electrostatic interaction of positively charged pyridinium with other cellular organelles may compete with the driving force from morpholine and thus decrease or destroy the lysosome selectivity. Therefore, accurate lysosome-targeting should go with the manipulation of hydrophobicity and polarity cautiously.

Mammalian target of rapamycin (mTOR) has been identified as the suppressant of autophagy. Rapamycin, a lipophilic macrolide antibiotic, can bind to mTOR and enhance autophagy and is thus widely used for autophagy induction. The chemical structure of rapamycin is shown below:

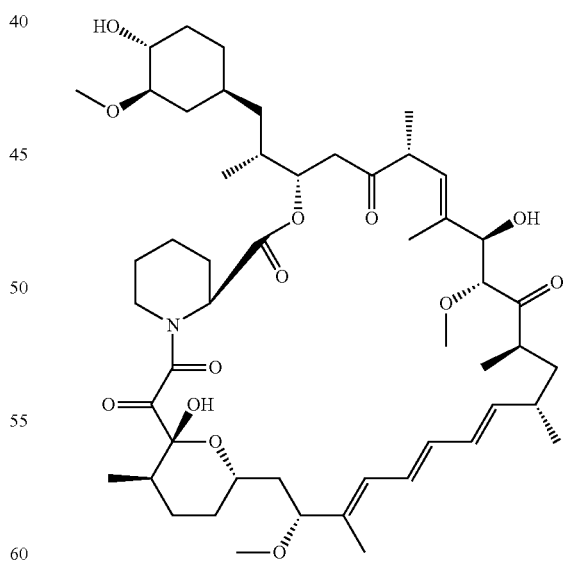

Treatment with rapamycin has been demonstrated to prolong the survival of prion protein infected mice by activating autophagy and prion protein degradation. During treatment with rapamycin, there is an increase in the number, size, and acidity of lysosomes. By employing AIE-LysoY with high lysosome targetability and excellent photostability, the autophagy process can be tracked in long term, which will provide more insight into the cellular activities. To demonstrate this feasibility, HeLa cells were stained by 10 μM of AIE-LysoY for 10 min and then treated with rapamycin for different periods of time, followed by observation under fluorescence microscope.

Lysosome can be clearly visualized under the fluorescence microscope. During the autophagy process, the amount of lysosome will be increased and the lysosome will fuse with autophagosome to form autolysosome. The amount of yellow spots, which corresponds to the lysosome number, are increased with prolonged rapamycin treatment. If the image is enlarged, lysosome can be visualized with excellent resolution and contrast. Notably, the newly formed lysosomes light up, even when the excessive AIE-LysoY was removed prior to rapamycin treatment. The result strengthened the occurrence of the fusion between the autophagic compartment and primitive lysosome during autophagy.

In addition, LTR provided similar fluorescence images and showed good overlapping with AIE-LysoY in rapamycin-treated HeLa cells. However, LTR should be co-incubated with rapamycin, otherwise its emission will be greatly diminished when excessive LTR is washed away beforehand. By virtue of its high selectivity towards lysosome and excellent photostability, AIE-LysoY is an excellent candidate as lysosome selective bioprobe for investigating the autophagy process.

Example 6

Lysosomal Imaging

The behavior of TPE-TMX in cellular settings was studied as compared to TMX. MCF-7 cells were incubated with 2 μM TPE-TMX and 50 nm TMX for 24 hrs, respectively. The cells were then washed and directly observed under the microscope without fixation. Surprisingly, TMX and TPE-TMX share similar intracellular distributions in MCF-7, where both drugs seem to localize around the nuclei of the cells. However, the exact intracellular location of TMX cannot be confirmed by fluorescent microscopy because its emission wavelength is not in the range of the visible spectrum. Therefore, a series of commercial fluorescent markers were used to image drug delivery of TMX. Noteworthily, LTR, a lysosome specific dye, can perfectly match with TMX, suggesting that TMX is possible to be localized on the lysosomes. On the other hand, TPE-TMX, without any aid of fluorescent dye, can be successfully monitored in the cells thanks to its intense blue emission. The controls display no emission under UV irradiation. This result demonstrates that the origin of the blue fluorescence comes from TPE-TMX but not auto-fluorescence from cells.

To further confirm the subcellular distribution of TPE-TMX, LTR was also used to co-stain MCF-7 cells with TPE-TMX. MCF-7 cells were first incubated with 2 μM TPE-TMX for 30 min, then with LTR for 15 min. the distribution of blue fluorescence from TPE-TMX co-localizes with red fluorescence from LTR, indicating that TPE-TMX selectively stains lysosomes in living cells. The Pearson correlation coefficient determines for these images showed excellent co-localization between LTR and TPE-TMX in cells (r=0.96). As expected, TPE-TMX is a specific fluorescent dye to visualize lysosomal organelle structures as well as monitor the drug release.

Anti-Tumor Specificity

Figure 33:
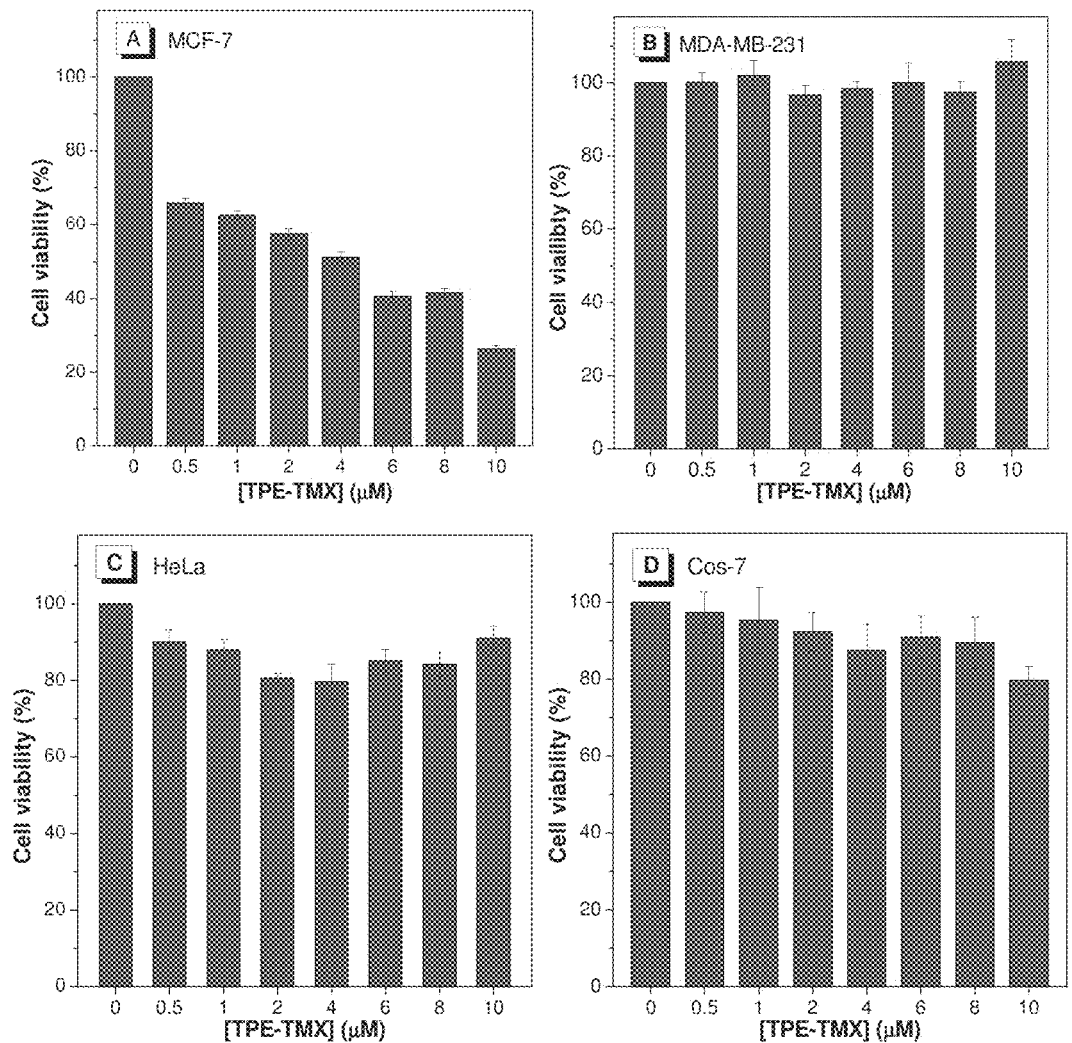
FIG. 33 shows cell viability of different cells incubated with different concentration of TPE-TMX.

For the rational molecular design of TPE-TMX, it is extremely critical that it can restore its therapeutic ability as TMX after the modification. To investigate its therapeutic performance, the cytotoxicity of TPE-TMX to a variety of cell lines was evaluated using a MTT assay (FIG. 33). The result shows that TPE-TMX has only the therapeutic response to ER+ breast cancer cells (MCF-7 cells), similar to TMX, but the cell viabilities of others, even ER independent breast cancer cells (MDA-MB-231 cells) are not dramatically altered up to 10 μM TPE-TMX. Therefore, TPE-TMX may form a complex with receptor that can manifest selective accumulation in MCF-7 cells and lead to cell death.

To examine this hypothesis, fluorescence microscopy of different cell lines treated with TPE-TMX was undertaken. It can be noticed that TPE-TMX was localized on lysosomes in all tested cell lines. Lysosome is an acidic enzyme enriched organelle responsible for digesting intracellular biomolecules, while TPE-TMX with a basic amino group is more favored to target the lysosomes in cells. Once the molecules are accumulated on the surface of lysosome, their intermolecular motions are restricted, which activates the AIE process and thus lights up the organelle. However, the fluorescence intensity of TPE-TMX was more prominent in MCF-7 cells compared to the others. Moreover, the data revealed that TPE-TMX induces the formation of vacuole, lysosomal swelling and cell death in MCF-7 cells, whereas no obvious morphological change has been observed in other cell lines.

Photostability

In order to determine the working mechanism of TPE-TMX to MCF-7 cells, probes with long-term tracking are highly pursued. To compare the photo-bleaching resistance between TPE-TMX and LTR, continuous scanning of the stained MCF-7 cells by UV irradiation was carried out and the PL intensity at each scan was recorded. These two sets of MCF-7 cells were first incubated in a medium for 24 hrs and then stained with TPE-TMX and LTR at 2 μM for 30 min, respectively. The excitation power from 405 nm and 561 nm channels of the microscope was unified as 0.1 mW. The initial fluorescence intensity for the dyes was normalized and the percentage of intensity loss was calculated. As shown in FIG. 34, no significant PL loss was observed in TPE-TMX after 50 scans in a total irradiation time of 3 min, while more than 55% signal loss was recorded for LTR. This result suggests that TPE-TMX presented here shows much higher photo-bleaching resistance than LTR.

Long-Term Tracing

In the case of lysosomal imaging using LTR, fluorescence of the stained cells is dramatically weakened with an increase in the number of passages. However, TPE-TMX behaves differently from its counterparts, and the fluorescent intensity of stained cells increases with increasing number of passages due to the formation of autolysosomes with AIE-active aggregates. Continuous monitoring of MCF-7 cells treated with TPE-TMX (2 μM) was shown to induce vacuoles, lysosome swelling, and loss of the cell population. The whole cells exclude nuclei are highly emissive after the treatment of TPE-TMX for 192 hrs, which is proposed as autophagy. This mechanism is thought to be a degradation system that is mediated by a unique organelle called the autophagosome and then fuses with lysosome to form an autolysosome. Once the autolysosomes are formed, the cells become dysfunctional and eventually cause cell death. Noticeably, the finding demonstrates the proposed mechanism is contradictory to the commonly accepted mechanism of TMX, in which the TMX-receptor complex can enter the nuclei of cells for antitumor activity. This is the first time that autophagy can be fluorescently monitored using a theranostic agent for breast cancer cells.

Example 7

Characterization: Steady-state fluorescence spectra were recorded on a Perkin Elmer LS 55 spectrometer. Fluorescent images were collected on Olympus BX 41 fluorescence microscope.

Cell Culture. HeLa cells were cultured in MEM containing 10% FBS and 1% antibiotics (100 units/mL penicillin and 100 g/mL streptomycin) in a 5% $CO_2$ humidity incubator at 37° C. Cell Imaging. Lung cancer cell A549 were cultured in DMEM containing 10% FBS and antibiotics (100 units/mL penicillin and 100 g/mL streptomycin) in a 5% $CO_2$ humidity incubator at 37° C. Two different kind of cells were grown overnight on a 35 mm petri dish with a cover slip. The live cells were incubated with 10 μM of TTE for 15/30 mins, TFE for 30' and fl-TFE for 30' and 5 h (the last two have been tested only in HeLa cells). In a typical experiment, 2 μL of a 10 mM stock solution of TTE in DMSO were diluted to 1 mL with cell culture medium, followed by further dilution to desired concentration. The cells were imaged under a fluorescent microscope (BX41 Microscope) using same excitation and emission filters: excitation filter=330-385 nm, dichroic mirror=420 nm, and emission filter=400 nm long pass.

AIE Study on TetraThienylEthene TTE and TetraFurylEthene TFE, Luminescent Features in fl-TTE and in fl-TFE.

TTE

Figure 36:
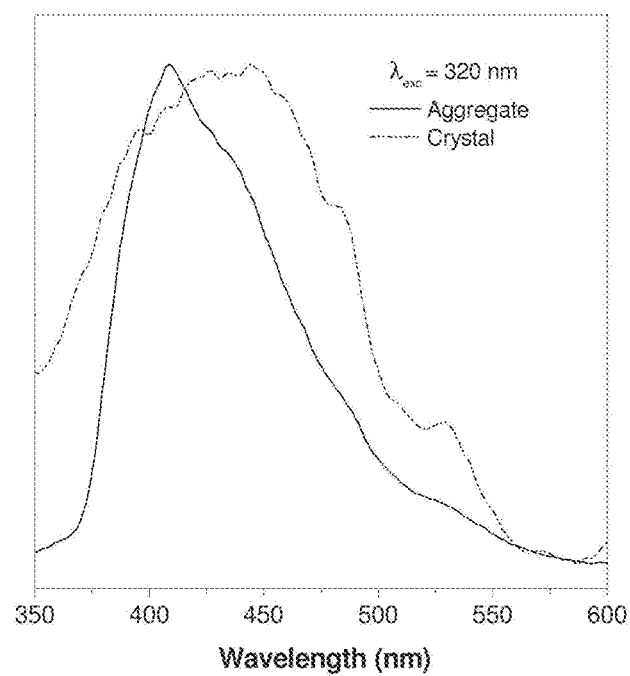
FIG. 36 shows the PL spectrum of TTE in aggregate and crystal state. Excitation at 320 nm.
Figure 39:
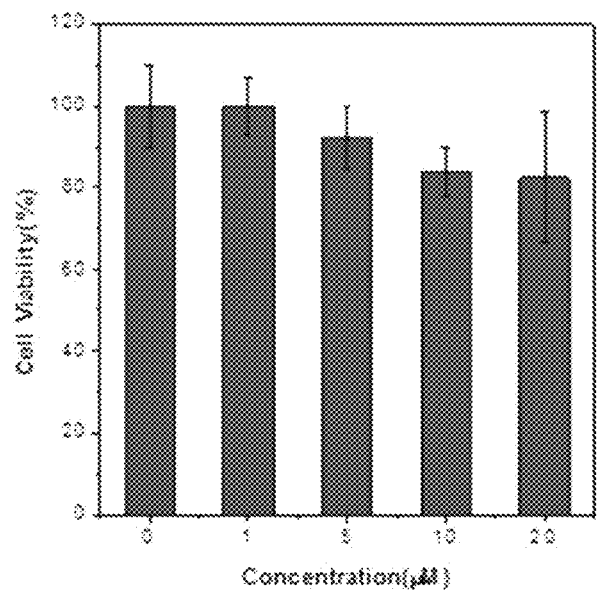
FIG. 39 shows cell viability tested by MTT assay: Hela cells were incubated with different concentrations of TTE in culture medium for 24 hours.
Figure 40:
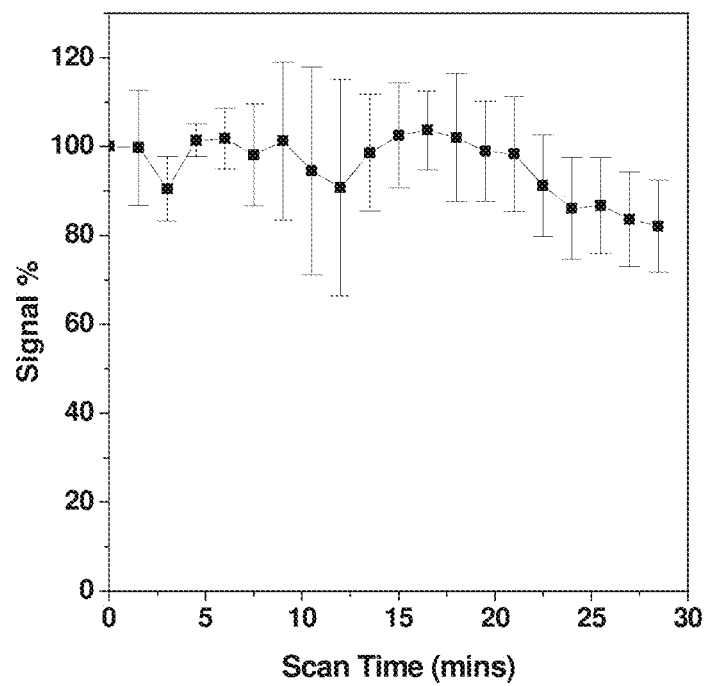
FIG. 40 shows photostability of TTE in HeLa cell.

AIE and clusteroluminogenic properties: TTE shows typical AIE features as shown in FIG. 35A-B. The THF solution of TTE was non-emissive while the aggregation state of 99% water fraction emits luminescence at 410 nm upon the UV excitation. As shown in FIG. 36 and in Table 1:

TABLE 1

Photophisycal data of the investigated molecules: TTE, sl-TTE and fl-TTE; and of TPE indicated as benchmark

| Luminogen | $\lambda_{ab}$/nm | $\Delta E$/eV | $\lambda_{em}$/nm Aggregate | Powder | Crystal | $\Delta\lambda^a$/nm | AIE or ACQ | $\alpha$AIE[b] | $\Phi_{F,A}$/% | $\tau$/ns |
|---|---|---|---|---|---|---|---|---|---|---|
| TPE | 360 | 3.45 | 462 | 447 | 450 | −12 | AIE | 344 | 23[c] | 1.29[c] |
| TTE | 413 | 3.01 | 409 | 413 | 444 | 35 | AIE | 20 | 2.6[c] | 0.47[c] |
| sl-TTE | 359 | 3.46 | 380[c], 389[c], 489[d] | | | / | AIE and ACQ | 1.47 | N.A. | N.A. |
| fl-TTE | 382 | 3.25 | 381[d]; 450[e] | | | / | ACQ | 0.1 | 0.1 | 0.94 |

The luminescence is red-shifted in crystal state. This is due to the clusteroluminogenic effect which reaches its maximum in the crystal state where S•••S interactions take place.

TFE

AIE and clusteroluminogenic properties: Like TTE, TFE is an AIEgen. It shows typical AIE features as shown in FIG. 42A-B. The THF solution of TFE was non-emissive while the aggregation state formed at 99% water fraction emits luminescence at 489 nm upon the UV excitation, as shown in Table 2:

TABLE 2

Summary of the optical properties of TPE, TFE, and fl-TFE

| Luminogen | $\lambda_{ab}$ (nm) | $\lambda_{em}$ (nm) Aggregate 99% fw | Powder | Crystal | $\Delta E$ (eV) | AIE or ACQ | $\alpha$AIE | $\Phi_{F,A}$/(%) | $\tau$ (ns) |
|---|---|---|---|---|---|---|---|---|---|
| TPE (benchmark) | 360 | 462 | 447 | 450 | 3.45 | AIE | 344 | 23[b] | 1.29[b] |
| TFE | 439 | 489 | 499 | 532 | 2.83 | AIE | 8.92 | 11[b] | 1.58[b] |
| fl-TFE | 363 | 524[a] | 465 | / | 3.42 | ACQ | 0.0001 | n.a. | n.a. |

[i]Abbreviation: $\lambda_{ab}$ = absorption maximum in THF; $\lambda_{em}$ = emission maximum in THF/water mixture (1:9 v/v), $\Delta E$, Energy gap calculated by UV-Vis spectrum, $\Phi_{F,A}$ = absolute fluorescent quantum yield measured by a calibrated integrating sphere;

[a]The value is referred to the aggregation condition, as specified in the table, the emission of fl-TFE in pure THF occurs at 361 nm.

[b]amorphous.

The luminescence is red-shifted in crystal state. This is due to the clusteroluminogenic effect, which reaches its maximum in the crystal state where O•••O interactions take place.

fl-TTE fl-TTE shows typical ACQ features as shown in FIG. 38A-B. The THF solution of fl-TTE was strongly emissive in solution, in which the emission occurs at 381 nm. Upon the increase of water fraction, the emission is quenched, but taking photos of the fl-TTE in powder under a 365 nm irradiation wavelength, emission light is perceivable. To decipher this phenomenon, crystal analysis is needed. Since this molecule, even if it is a locked form of TTE, still owns sulfur atoms, a possible S to S interaction might be involved.

fl-TFE fl-TFE shows typical ACQ features, as shown in FIG. 44A-B. The THF solution of fl-TFE was strongly emissive in solution, (FIG. 44A-B) in which the emission occurs at 361 nm. The ACQ behavior is recordable at this wavelength, however upon the increase of the water fraction, the emission is red-shifted and a green peak is catchable at 524 nm in 99% fw. fl-TFE shows green emission even in powder state, the PL value is around 465 nm, shown in Table 3:

TABLE 3

Summary of the optical properties of TPE, TFE, and fl-TFE

| Luminogen | $\lambda_{ab}$ (nm) | $\lambda_{em}$ (nm) Aggregate 99% fw | Powder | Crystal | $\Delta E$ (eV) | AIE or ACQ | $\alpha AIE$ | $\Phi_{F,A}$/(%) | $\tau$ (ns) |
|---|---|---|---|---|---|---|---|---|---|
| TPE (benchmark) | 360 | 462 | 447 | 450 | 3.45 | AIE | 344 | 23[b] | 1.29[b] |
| TFE | 439 | 489 | 499 | 532 | 2.83 | AIE | 8.92 | 11[b] | 1.58[b] |
| fl-TFE | 363 | 524[a] | 465 | / | 3.42 | ACQ | 0.0001 | n.a. | n.a. |

[i]Abbreviation: $\lambda_{ab}$ = absorption maximum in THF; $\lambda_{em}$ = emission maximum in THF/water mixture (1:9 v/v), $\Delta E$, Energy gap calculated by UV-Vis spectrum, $\Phi_{F,A}$ = absolute fluorescent quantum yield measured by a calibrated integrating sphere;
[a]The value is referred to the aggregation condition, as specified in the table, the emission of fl-TFE in pure THF occurs at 361 nm.
[b]amorphous.

Since fl-TFE owns O as a heteroatom, its emission ability in aggregation and solid state could be ascribed to the clusteroluminogenic effect. Further due to this, there is a red shift of the wavelength, since in aggregate state, the color is green.

AIE and Photochromic Properties of sl-TTE:

The sl-TTE shows both ACQ and AIE behavior as is shown in FIGS. 37A-B and in Table 4:

TABLE 4

Crystal Data of TTE and TPE
Dihedral Angle[1]

| Ring | TTE | TPE (benchmark) |
|---|---|---|
| I | 84.72 | 45.50 |
| II | 24.61 | 47.33 |
| III | / | 44.59 |
| IV | / | 56.37 |

[1]Angle between the plane of each ring and the double bond one.

It also shows solid state photochromic behavior, as its color is changed in 30" from white to light-pink after irradiating the powder by UV lamp. The process is reversible, as the color turns to white after irradiating the pink powder by visible light.

Cancer Cell Imaging for Hela Cell by Using TTE:

The HeLa cells were grown overnight on a 35 mm petri dish with a cover slip. The live cells were incubated with 10 μM of TTE for 30 mins, which are shown in FIG. 17A-B. The HeLa cells were incubated with 50 μM oleic acid for 6 hrs and then were co-stained by 10 μM TTE and 1 μg/mL for 15 mins. The good overlap between images of TTE and BODIPY indicated that TTE can selectively target lipid droplets.

Cancer Cell Imaging for Lung Cancer Cell A549 by Using TTE:

The A549 cells were grown overnight on a 35 mm petri dish with a cover slip. The live cells were incubated with 10 μM of TTE for 30 mins. The A549 cells were incubated with 10 μM TTE and 1 μg/mL for 15 mins. The good overlap between Images of TTE and BODIPY indicated that TTE can selectively target lipid droplets.

Synthesis of 4,5-Bis(thiophene-2-yl)thieno[3,2-e]benzo[b]thiophene (sl-TTE) and Tetrathieno[2,3-a:3',2'-c:2'',3''-f:3''',2'''-h]-naphthalene (fl-TTE)

In a typical run for photochemical reactions, 80 mg (0.217 mmol, 1 eq) of Tetrakis(2-thienyl)ethane (TTE) were dissolved in 200 mL of Toluene (solution color: yellow) and the solution was de-aerated under $N_2$ atmosphere for 30'. After this time, 116 mg (0.457 mmol, 2 eq) of $I_2$ were added to the solution (which turned its color from yellow to red) and it was de-aerated again for other 30'. Then 50 mL (714 mmol, d=0.83 g mL$^{-1}$) of 2-methyl oxirane (propylene oxide) were added in the reaction mixture and the solution was de-aerated for 30' more. The resulting mixture was irradiated with UV-light from a 500 W high pressure Hg vapor lamp placed in the immersion quartz well under $N_2$ flow.

The reaction was monitored by TLC (eluent: Hexane/DCM 8/2) and it was carried on till the consumption of the starting material and the appearance of the final product. The overall reaction time was 20'. The reaction product precipitated during the photolysis due to its insolubility in the reaction solvent. The crude was washed with DCM and Ethanol to remove the alcohol (1-idroxy, 2-Indo, 2-MethylEthane) byproduct of this reaction, which is soluble in this medium, contrarily to the reaction products which are insoluble both in DCM and in EtOH. By washing the residual crude with Hexane, it was possible to isolate the intermediate product (4,5-Bis(thiophene-2-yl)thieno[3,2-e]benzo[b]thiophene (sl-TTE). By recrystallizing once the remaining crude, from Ortho-Xylene it was obtained the final desired product Tetrathieno[2,3-a:3',2'-c:2'',3''-f:3''',2'''-h]-naphthalene (fl-TTE) (50 mg 64% yield) as pink microcrystalline powder.

(fl-TTE). $^1$H-NMR (400 MHz, $CS_2$+ Acetone d6): δ, ppm=8.09 (d, 1H, J=4.8 Hz), 7.94 (d, 1H, J=5.2 Hz), UV/Vis (THF), λ/nm: 338; ε, M$^{-1}$ cm$^{-1}$:18.6 E$^4$; optical energy gap: 3.67 eV; MS: 352.96 [M+]; HPLC (reverse phase, analytical column SB-C18, eluent: ACN:H$_2$O 9:1) retention time: 7.12'. The mass spectrum (MALDI) read exact mass of 352.9580 for fl-TTE.

(sl-TTE). $^1$H-NMR (400 MHz, CS$_2$+ Acetone d6): δ, ppm=7.99 (d, 1H, J=4.8 Hz), 7.86 (d, 1H, J=4.8 Hz), 7.54 (d, 1H, J=4.8 Hz), 7.25 (bs, 1H), 7.11 (bs, 1H), UV/Vis (THF), λ/nm: 320; ε, M$^{-1}$ cm$^{-1}$:7.73 E$^3$; optical energy gap: 3.88 eV; MS: 353.97 [M+]; HPLC (reverse phase, analytical column SB-C18, eluent: ACN:H2O 9:1) retention time: 3.94'. The mass spectrum (MALDI) read exact mass of 353.9685 for sl-TTE.

Synthesis of Tetrakis(2-furyl)ethene, TFE

In a four necked flask (100 mL) equipped with nitrogen inlet, thermometer and condenser, was introduced de-aerated, dry THF (17 mL). Then the solvent was cooled to −10° C. and TiCl$_4$ (0.31 mL, 2.8 mmol) was added under inert atmosphere. The temperature was raised to −7° C. and the reaction mixture became yellow. Then zinc (0.42 g, 6.0 mmol) was added in two portions, temperature raised up to −5° C. The reaction mixture was allowed to stir for 30 minutes between −7/−9° C. At the end of formation of Ti(0) the reaction mixture looked like a green suspension. A solution of di-2-furylketone (0.43 g, 2.7 mmol) in 3 mL of dry THF was added dropwise to the reaction mixture at 0° C. Then the reaction was allowed to reach room temperature within 1, 5 hrs and left stirring overnight.

The reaction was monitored by TLC (n-Hexane/AcOEt: 8/2) till the complete consumption of the ketone. Then the reaction mixture was poured into 20 mL of Et2O and treated with saturated NaHCO$_3$ solution till slightly basic pH. This mixture was allowed to stir for 10 minutes and then filtered through a Celite pad. The organic layer (orange) was separated from the aqueous phase. The aqueous phase was extracted repeatedly with DCM (dichloromethane) which seemed a better solvent than Et$_2$O. The organic phases were collected together and dried over Na$_2$SO$_4$. Sodium sulfate was filtered off and the solvent distilled off leaving 300 mg of crude. The crude was purified by column chromatography (Hexane/DCM: 1/1) affording 191 mg of desired product (49% yield).

m.p.=163-164° C., $^1$H-NMR (300 MHz, CDCl$_3$): δ, ppm=7.35 (d, 1H, J=1.6 Hz), 6.44 (dd, 1H, J=3.36 Hz, J=1.6 Hz), 6.30 (d, 1H, J=3.33 Hz), $^{13}$C-NMR (75 MHz, CDCl$_3$): δ, ppm=152.96 (Cq), 142.65 (Cp), 112.24 (Cp), 111.39 (Cp). Notes: It is important to store the product in the dark, under N$_2$ atmosphere, otherwise it becomes dark; in this case it is enough to purify it by filtration on silica pad using Hexane: DCM 8:2 as eluent.

Synthesis of Tetrafuro[2,3-a:3',2'-c:2'',3'''-f:3''',2'''-h]-naphthalene-(fl-TFE)

In a typical run for photochemical reactions, 110 mg (0.38 mmol, 1 eq) of Tetrakis(2-furyl)ethene (TFE) were dissolved in 200 mL of Toluene (solution color: yellow) and the solution was de-aerated under N$_2$ atmosphere for 30'. After this time, 193 mg (0.76 mmol, 2 eq) of I$_2$ were added to the solution (which turned its color from yellow to red) and it was de-aerated again for other 30'. Then 40 mL (572 mmol, d=0.83 g mL$^{-1}$) of 2-methyl oxirane (propylene oxide) were added in the reaction mixture and the solution was de-aerated for 30' more. The resulting mixture was irradiated with UV-light from a 500 W high pressure Hg vapor lamp placed in the immersion quartz well under N$_2$ flow.

The reaction was monitored by TLC (eluent: Hexane/DCM 8/2) and it was carried on till the consumption of the starting material and the appearance of the final product. The overall reaction time was 45'. The crude was washed with saturated aqueous solution of Sodium metabisulphite and extracted with DCM. The crude was washed with Ethanol to remove the alcohol (1-idroxy, 2-Indo, 2-MethylEthane) byproduct of this reaction. The residual crude has been recrystallizing once, from Ortho-Xylene so obtaining the final desired product Tetrafuro[2,3-a:3',2'-c:2'',3''1:3'',2''-h]-naphthalene (fl-TTE) (~22% yield) as yellow microcrystalline powder.

(fl-TFE). $^1$H-NMR (400 MHz, THF d$_8$): δ, ppm=8.09 (d, 1H, J=2.0 Hz), 7.32 (d, 1H, J=2.0 Hz), $^{13}$C-NMR (400 MHz, THF d$_8$): δ, ppm=106, 118, 146; UV/Vis (THF), λ/nm: 338; optical energy gap: 3.67 eV; MS: 288.04 [M+]; HPLC (reverse phase, analytical column SB-C18, eluent: ACN:H$_2$O 7:3) retention time: 5.40'. The mass spectrum (MALDI) read exact mass of 288.0429 (288.04226 predicted) for fl-TFE.

Example 8

Synthesis of IDA-TPE Characterization:

Steady-state fluorescence spectra were recorded on a Perkin Elmer LS 55 spectrometer. Fluorescent images were collected on Olympus BX 41 fluorescence microscope.

Cell Culture. HeLa cells were cultured in MEM containing 10% FBS and 1% antibiotics (100 units/mL penicillin and 100 g/mL streptomycin) in a 5% CO$_2$ humidity incubator at 37° C.

Cancer Cell Imaging for HeLa Cell by Using IDA-TPE:

The HeLa cells were grown overnight on a 35 mm petri dish with a cover slip. The live cells were incubated with 10 μM of IDA-TPE for 30 mins, which are shown in FIG. 45 The bright fluorescence showed that IDA-TPE can target HeLa cells. The cells were imaged under a fluorescent microscope (BX41 Microscope) using same excitation and emission filters: excitation filter=330-385 nm, dichroic mirror=420 nm, and emission filter=400 nm long pass.

The synthesis of IDA-TPE is shown below:

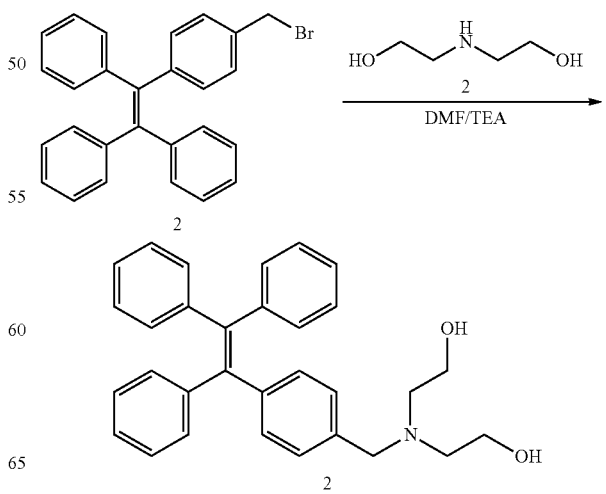

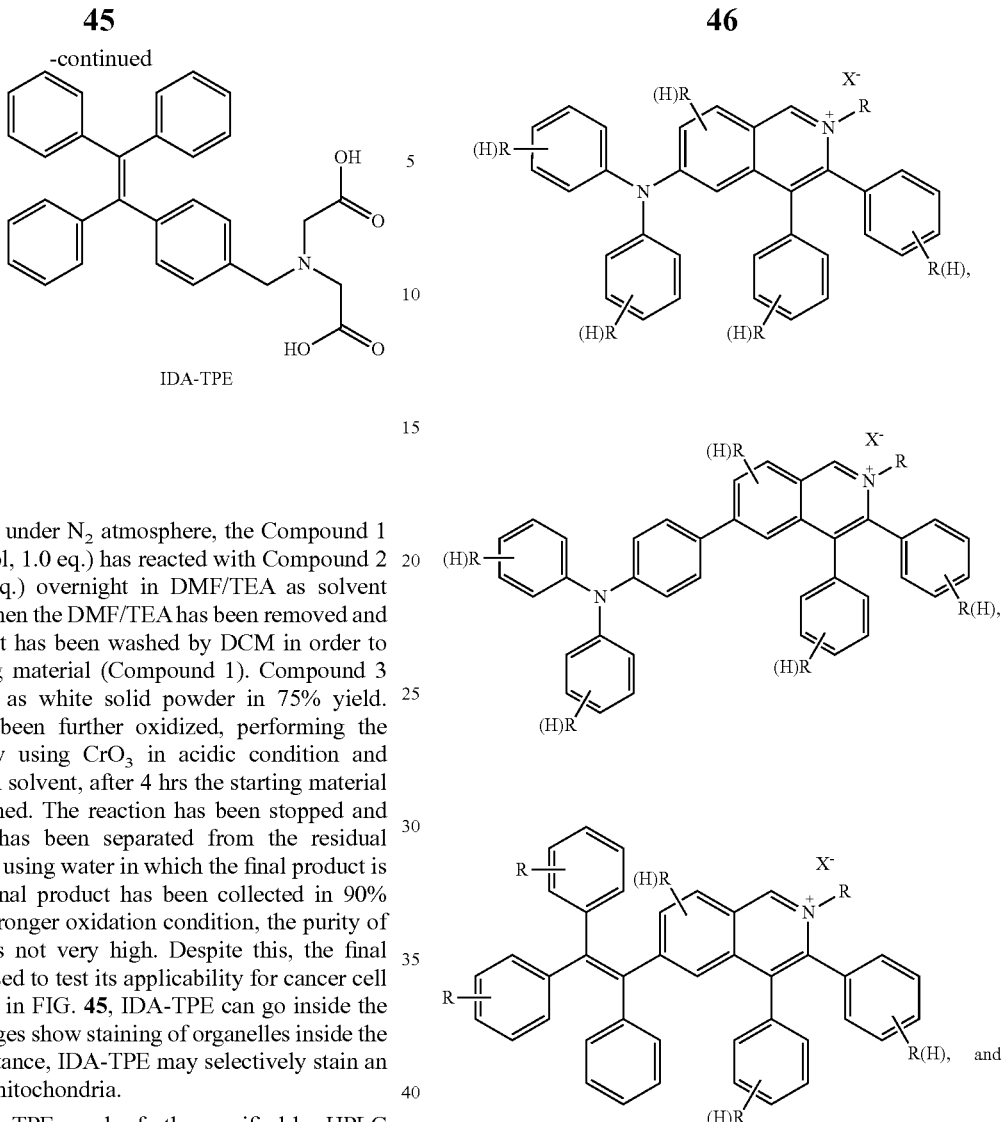

IDA-TPE

In a 2 neck-flask under $N_2$ atmosphere, the Compound 1 (200 mg, 0.47 mmol, 1.0 eq.) has reacted with Compound 2 (0.56 mmol, 1.2 eq.) overnight in DMF/TEA as solvent reaction mixture. Then the DMF/TEA has been removed and the residual product has been washed by DCM in order to remove the starting material (Compound 1). Compound 3 has been obtained as white solid powder in 75% yield. Compound 3 has been further oxidized, performing the Jones oxidation by using $CrO_3$ in acidic condition and Acetone as reaction solvent, after 4 hrs the starting material was almost consumed. The reaction has been stopped and the final product has been separated from the residual starting material by using water in which the final product is not soluble. The final product has been collected in 90% yield. Due to the stronger oxidation condition, the purity of the final product is not very high. Despite this, the final product has been used to test its applicability for cancer cell imaging. As shown in FIG. 45, IDA-TPE can go inside the cancer cell and images show staining of organelles inside the cancer cell. For instance, IDA-TPE may selectively stain an organelle such as mitochondria.

If desirable, IDA-TPE can be further purified by HPLC using the following condition: column, reverse phase $XDBC_{18}$ ACN:$H_2O$ 60:40.

Characterization: $^1$H-NMR main peaks in Acetone $d_6$ δ (ppm): 7.16, 7.32, 7.46 (m, 9H), 4.8 (s, 1H); MALDI-TOF found at 447.1362 [$M^{2-}$].

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A probe for cancer cell imaging and staining comprising AIE luminogens having a chemical structure selected from the group consisting of:

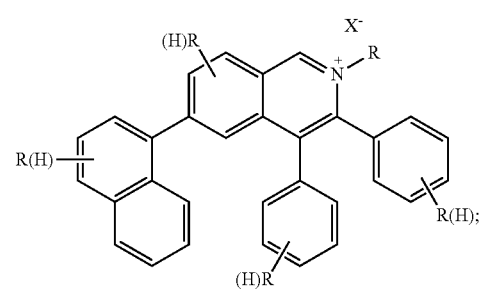

wherein the counteranion X− is selected from anions with single or more charges; and wherein each R is independently selected from the group consisting of alkyl, unsaturated alkyl, heteroalkyl, cycloalkyl, heterocycloalkyl, aryl, and heteroaryl, provided that R is not alkyl when R is a phenyl substituent.

2. The probe of claim 1, wherein the AIE luminogens are selected from the group consisting of:

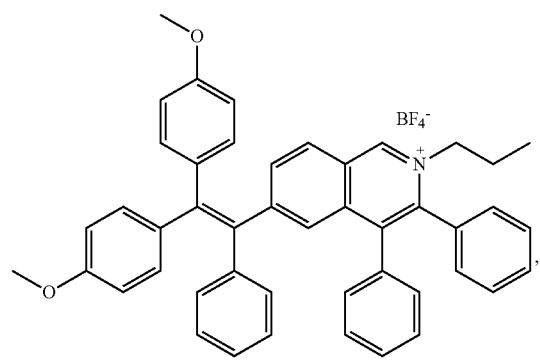

(TPE-1Q-2Q)

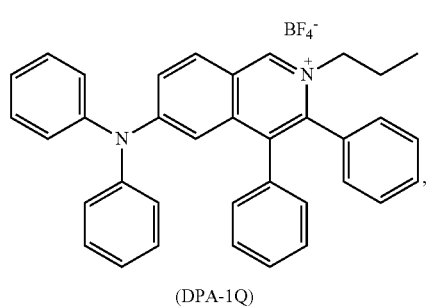

(DPA-1Q)

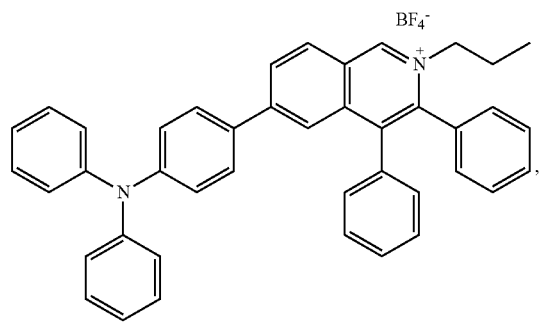

(TPA-1Q), and

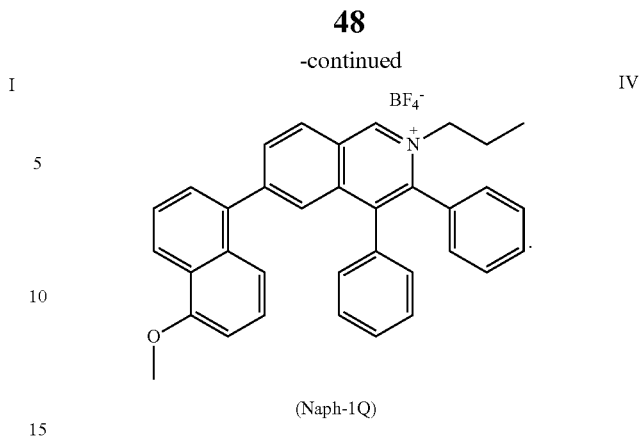

(Naph-1Q).

3. The probe of claim 1, wherein the probe exhibits mitochondria selectivity for staining.

4. The probe of claim 1, wherein the probe has two-photon absorption ability and can be excited by longer wavelengths.

5. The probe of claim 1, wherein the probe is used for mitochondria imaging, as the AIE luminogens have electrostatic interaction with mitochondria.

6. The probe of claim 1, wherein imaging is due to fluorescence emitted by probes uptaken by cells and accumulated in mitochondria.

7. The probe of claim 1, wherein the probe is used with an imaging sample comprising any kind of cells.

8. The probe of claim 7, wherein the imaging sample comprises any cancer cells.

9. The probe of claim 1, wherein the probe can distinguish normal cells from cancer cells by a difference in fluorescence intensity, wherein the cancer cells and the normal cells are stained separately or in a mixture.

10. The probe of claim 9, wherein the cancer cells have a higher fluorescence intensity and the normal cells have a lower fluorescence intensity, due to the cancer cells uptaking and accumulating more probes.

11. The probe of claim 1, wherein the probe is subject to light irradiation, which generates ROS.

* * * * *

UNITED STATES PATENT AND TRADEMARK OFFICE
CERTIFICATE OF CORRECTION

PATENT NO. : 10,935,552 B2  
APPLICATION NO. : 15/737187  
DATED : March 2, 2021  
INVENTOR(S) : Benzhong Tang et al.

Page 1 of 1

It is certified that error appears in the above-identified patent and that said Letters Patent is hereby corrected as shown below:

In the Specification

Column 15, first structure, please delete the label "(TPE-1Q-2Q)" and replace with "(TPE-1Q-2O)".

In the Claims

Claim 2, Column 47, first structure, please delete the label "(TPE-1Q-2Q)" and replace with "(TPE-1Q-2O)".

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*